US010000765B2

(12) United States Patent
Saika et al.

(10) Patent No.: US 10,000,765 B2
(45) Date of Patent: Jun. 19, 2018

(54) GENE ENCODING CYTOCHROME P450, AND USE THEREOF

(71) Applicants: NATIONAL INSTITUTE OF AGROBIOLOGICAL SCIENCES, Tsukuba, Ibariki (JP); KUMIAI CHEMICAL INDUSTRY CO., LTD, Tokyo (JP)

(72) Inventors: Hiroaki Saika, Ibaraki (JP); Fumio Taguchi, Ibaraki (JP); Kiyosumi Hori, Ibaraki (JP); Takashi Matsumoto, Ibaraki (JP); Tsuyoshi Tanaka, Ibaraki (JP); Junko Horita, Tokyo (JP); Koichiro Kaku, Tokyo (JP); Tsutomu Shimizu, Tokyo (JP)

(73) Assignees: NATIONAL INSITUTE OF AGROBIOLOGICAL SCIENCE, Tsukuba-Shi, Ibariki (JP); KUMIAI CHEMICAL INDUSTRY CO., LTD, Tokyo (JP)

(*) Notice: Subject to any disclaimer, the term of this patent is extended or adjusted under 35 U.S.C. 154(b) by 861 days.

(21) Appl. No.: 14/351,226

(22) PCT Filed: Oct. 12, 2012

(86) PCT No.: PCT/JP2012/076459
§ 371 (c)(1),
(2) Date: Apr. 11, 2014

(87) PCT Pub. No.: WO2013/054890
PCT Pub. Date: Apr. 18, 2013

(65) Prior Publication Data
US 2014/0274714 A1 Sep. 18, 2014

(30) Foreign Application Priority Data
Oct. 13, 2011 (JP) .................................. 2011-226174

(51) Int. Cl.
*C12N 15/82* (2006.01)
*C12N 9/04* (2006.01)
*C12N 9/02* (2006.01)
*G01N 33/50* (2006.01)

(52) U.S. Cl.
CPC ....... *C12N 15/8274* (2013.01); *C12N 9/0006* (2013.01); *C12N 9/0077* (2013.01); *G01N 33/5097* (2013.01)

(58) Field of Classification Search
CPC .............. C12N 9/0006; C12N 15/8274; C12N 9/0077; C12N 15/8278
See application file for complete search history.

(56) References Cited

U.S. PATENT DOCUMENTS

| 2007/0167328 A1* | 7/2007 | Endo ...................... A01N 43/54 504/104 |
| 2011/0214199 A1* | 9/2011 | Coffin ................. C12N 15/1079 800/275 |
| 2013/0042366 A1 | 2/2013 | Mankin et al. |

FOREIGN PATENT DOCUMENTS

| TW | 201129697 A | | 9/2011 | |
| WO | WO/2011/085221 | * | 7/2011 | ............... A01H 5/00 |
| WO | WO 2011/085221 | * | 7/2011 | ............... A01H 5/00 |

OTHER PUBLICATIONS

Imaishi, Hiromasa, and Suzuko Matumoto. "Isolation and functional characterization in yeast of CYP72A18, a rice cytochrome P450 that catalyzes (ω-1)-hydroxylation of the herbicide pelargonic acid." Pesticide biochemistry and physiology 88.1 (2007): 71-77.*
Werck-Reichhart, Danièle, Alain Hehn, and Luc Didierjean. "Cytochromes P450 for engineering herbicide tolerance." Trends in plant science 5.3 (2000): 116-123.*
UniProtKB/TrEMBL database entry A2WS96_ORYSI, published on Mar. 20, 2007, www.uniprot.org/uniprot/A2WS96.*
Nelson, David R., "Cytochrome P450 Nomenclature, 2004." Cytochrome P450 Protocols (2006): 1-10.*
Zhang, Lei, et al. "Identification of a cytochrome P450 hydroxylase, CYP81A6, as the candidate for the bentazon and sulfonylurea herbicide resistance gene, Bel, in rice." Molecular Breeding 19.1 (2007): 59-68.*
Saika, Hiroaki, et al. "A novel rice cytochrome P450 gene, CYP72A31, confers tolerance to acetolactate synthase-inhibiting herbicides in rice and Arabidopsis." Plant physiology 166.3 (2014): 1232-1240.*
Zhang, L., et al., 2007, Molecular Breeding 19:59-68.*
First Office Action dated Dec. 3, 2014, in Chinese Patent Application No. 201280050212.X, with English tranaslation.
Siminszky, B., "Plant cytochrome P450-mediated herbicide metabolism," Phytochem. Ref. (2006), vol. 5, pp. 445-458.
Office Action with Search Report dated Mar. 24, 2016, in Taiwan Patent Application No. 101137878.
"hypothetical protein Osl_02734 [*Oryza sativa* Indica Group]", EAY74842, EAY74842.1, [online], National Center for Biotechnology Information, published on Dec. 17, 2008, searched on Nov. 21, 2012, Internet, http://www.ncbi.nlm.nih.gov/protein/125526728.
"OslFCC002559 *Oryza sativa* Express Library *Oryza sativa* Indica Group genomic, genomic survey sequence", CL959279, [online], National Center for Biotechnology Information, published on Sep. 21, 2004, searched on Nov. 21, 2012, Internet, http://www.ncbi.nlm.nih.gov/nucgss/CL959279.

(Continued)

*Primary Examiner* — Lee A Visone
*Assistant Examiner* — Weihua Fan
(74) *Attorney, Agent, or Firm* — Birch, Stewart, Kolasch & Birch, LLP

(57) ABSTRACT

To identify a cytochrome P450 involved in the detoxification and metabolism of a specific growth inhibitor.
Provided is a gene encoding a cytochrome P450 classified into Indica rice-derived CYP72A31, comprising a polynucleotide encoding a protein comprising an amino acid sequence of SEQ ID NO: 2.

11 Claims, 36 Drawing Sheets
(32 of 36 Drawing Sheet(s) Filed in Color)

(56) References Cited

OTHER PUBLICATIONS

Imaishi et al., "Isolation and functional characterization in yeast of CYP72A18, a rice cytochrome P450 that catalyzes (ω-1)-hydroxylation of the herbicide pelargonic acid", Pesticide Biochemistry and Physiology, 2007, vol. 88, pp. 71-77.
International Search Report, issued in PCT/JP2012/076459, dated Dec. 4, 2012.
Nelson et al., "Comparative Genomics of Rice and *Arabidopsis*. Analysis of 727 Cytochrome P450 Genes and Pseudogenes from a Monocot and a Dicot", Plant Physiology, Jun. 2004, vol. 135, pp. 756-772.
Saika et al., "A novel cytochrome P450 CYP72A31 gene is involved in the tolerance to the herbicide, Bispyribac sodium in rice", Breeding research, Mar. 29, 2012, vol. 14, p. 91, #420.
Werck-Reichhart et al., "Cytochromes P450 for engineering herbicide tolerance", Trends in Plant Science, Mar. 2000, vol. 5, No. 3, 116-123.
Written Opinion of the International Search Authority, issued in PCT/JP2012/076459, dated Dec. 4, 2012.

\* cited by examiner

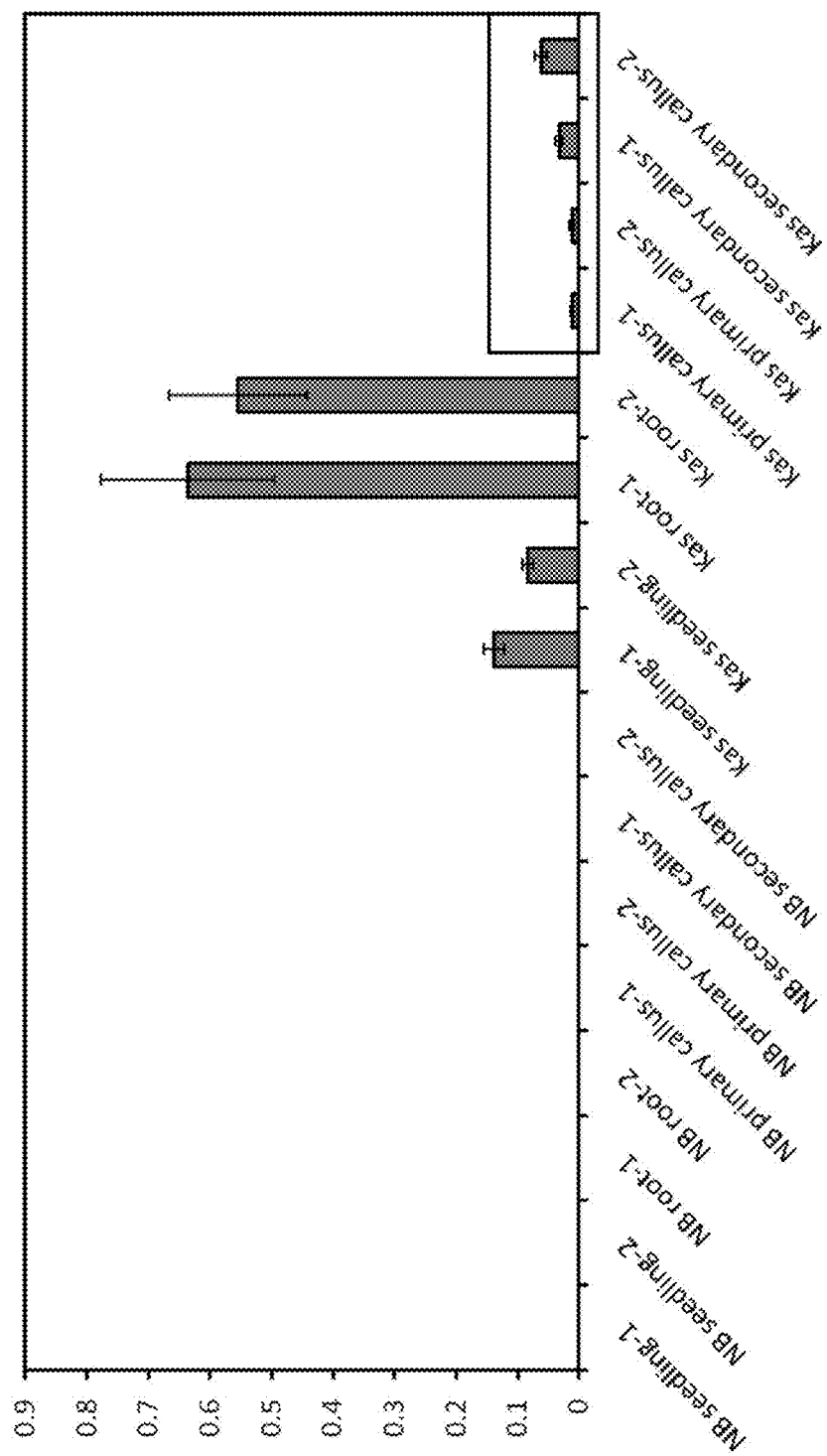

Bensulfuron-methyl

NT (nM) 1.3    4.1    12

37    110    330

K31-4-2

(nM) 1.3    4.1    12

37    110    330

Penoxsulam

NT (nM) 1.3    4.1    12

37    110    330

K31-4-2

(nM) 1.3    4.1    12

37    110    330

BS

NT (μM) 0   0.01 0.1  1   10

K31-4-6-2

(μM) 0   0.01 0.1  1   10

Pinoxaden

NT (μM) 0   0.01 0.1  1   10

K31-4-6-2

(μM) 0   0.01 0.1  1   10 pCAMBIA1390-KasCYP72A31
BS 0.1 µM pCAMBIA1390-KasCYP72A31
BS 0.25 µM pSTARA-sGFP
BS 0.25 µM

GENE ENCODING CYTOCHROME P450, AND USE THEREOF

TECHNICAL FIELD

The present invention relates to genes encoding a cytochrome P450 having a distinguishing activity and use thereof. The present invention relates more particularly to an expression vector having the gene, a transformant and transgenic plant having the expression vector, a method for producing a plant having resistance to a substance exerting a harmful effect on plant growth, and a method for controlling weeds harmful to a plant.

BACKGROUND ART

There exists a wide variety of substances such as a substance lethal to plants and a substance effective in slowing plant growth. Hereinafter, the substance lethal to plants and the substance effective in slowing plant growth are generally referred to as a substance having a harmful effect on plant growth or a growth inhibitor.

For example, use of agrochemicals, growth regulators, fertilizers, or materials, which have been used for agriculture and horticulture, may cause a harmful effect on plants treated with the above compounds. This phenomenon is generally called herbicide injury and/or fertilizer injury. In addition, it has been known that microbes, arthropods, animals such as nematodes, and even other plants may produce a growth inhibitor to exert a harmful effect.

In order to circumvent this harmful effect, plants have measures against such a growth inhibitor. Examples of the measures include rendering the above substance harmless by detoxifying and metabolizing the substance, reducing uptake and incorporation of the substance, and promoting export of the substance. Among the particularly important measures is an activation of a function of detoxifying and metabolizing the substance. Examples of a known molecular species involved in such detoxification and metabolism include a cytochrome P450 having a monooxygenase activity (Non Patent Literature 1). Meanwhile, 350 or more members of rice P450 and 240 or more members of *Arabidopsis* P450 have been identified (Non Patent Literature 2). Unfortunately, a whole picture of the mechanism of detoxifying and metabolizing a growth inhibitor by a cytochrome P450 remains unresolved.

Accordingly, some of the mechanism of detoxifying and metabolizing a growth inhibitor by a cytochrome P450 are tried to be revealed. This can facilitate, for example, giving a desired plant the resistance to the growth inhibitor. Also, if a cytochrome P450 gene involved in the detoxification and metabolism of a particular growth inhibitor is identified, it is possible to provide a method for transformation using the cytochrome P450 gene as a selection marker.

PRIOR ART DOCUMENTS

Non-Patent Documents

Non Patent Literature 1: Daniele Werck-Reichhart et al., Trends in Plant Science, 5, 3, 116-123 (2000)
Non Patent Literature 2: David R. Nelson et al., Plant Physiology, 135, 756-772 (2004)

SUMMARY OF INVENTION

Problem to be Solved by the Invention

As described above, however, it remains unclear what is the mechanism of detoxifying and metabolizing any of many growth inhibitors having a variety of different mechanisms of action involved with a cytochrome P450. Hence, it has been difficult, as described above, to give a desired plant the resistance to a growth inhibitor by using a cytochrome P450 gene and/or to implement a method for transformation using the cytochrome P450 gene as a selection marker.

Here, it is an object of the present invention to identify a cytochrome P450 involved in the detoxification and metabolism of a specific growth inhibitor and to use a gene encoding the cytochrome P450.

Means for Solving Problem

The present inventors have conducted intensive research to solve the above problem, and have successfully identified a cytochrome P450 gene involved in resistance to a plant growth inhibitor. Use of this cytochrome P450 gene has led to production of a plant having the resistance to the growth inhibitor and construction of a method for transformation using the cytochrome P450 gene as a selection marker gene. Then, the present inventors have completed the present invention.

That is, the present invention includes the following aspects.

(1) A gene encoding a cytochrome P450 classified into Indica rice-derived CYP72A31, comprising a polynucleotide set forth in any of the following (a) to (c):

(a) a polynucleotide encoding a protein comprising an amino acid sequence of SEQ ID NO: 2;

(b) a polynucleotide encoding a protein having one or more amino acid deletions, substitutions, or additions in the amino acid sequence of SEQ ID NO: 2, wherein the polynucleotide functions as a gene imparting resistance to a growth inhibitor; and (c) a polynucleotide hybridized, under a stringent condition, with a polynucleotide comprising a nucleotide sequence complementary to a nucleotide sequence of SEQ ID NO: 1, wherein the polynucleotide functions as a gene imparting resistance to a growth inhibitor.

(2) An expression vector, comprising the gene according to the above (1).

(3) The expression vector according to the above (2), further integrating any gene other than the gene according to the above (1).

(4) A transformant, comprising the expression vector according to the above (2) or (3).

(5) A transgenic plant, comprising the expression vector according to the above (2) or (3).

(6) The transgenic plant according to the above (5), wherein the plant is a plant body, a plant organ, a plant tissue, or a plant cultured cell.

(7) A method for producing a plant having resistance to a growth inhibitor, comprising culturing or cultivating the transgenic plant according to the above (5) or (6).

(8) A method for controlling weeds harmful to the transgenic plant according to the above (5) or (6), wherein a growth inhibitor treatment is performed in a field where the transgenic plant is cultivated.

(9) A method for transformation, comprising the steps of: introducing the expression vector according to the above (3) into a host sensitive to a growth inhibitor; and screening for a cell growing under the presence of the growth inhibitor us a transformant.

This description includes part or all of the contents as disclosed in the description and/or drawings of Japanese Patent Application No. 2011-226174, which is a priority document of the present application.

Effect of the Invention

According to the present invention, a plant exhibits resistance to a growth inhibitor by the use of a gene encoding a cytochrome P450 involved in the detoxification and metabolism of the plant growth inhibitor. In addition, use of a cytochrome P450 gene according to the present invention as a selection marker gene enables a novel transformation method to be constructed. Furthermore, a cytochrome P450 gene according to the present invention can be used as a resistance marker gene that is an indicator for resistance to a plant growth inhibitor.

BRIEF DESCRIPTION OF THE DRAWINGS

The patent or application file contains at least one color drawing. Copies of this patent or patent application publication with color drawing will be provided by the USPTO upon request and payment of the necessary fee.

FIG. 5A is a graph illustrating the results of analyzing the expression of CYP72A31 gene in Nipponbare and Kasalath calluses.

(K31-4-2) transformed with a Kasalath-derived CYP72A31 gene and non-transformed *Arabidopsis thaliana* (NT).

Figure 23:
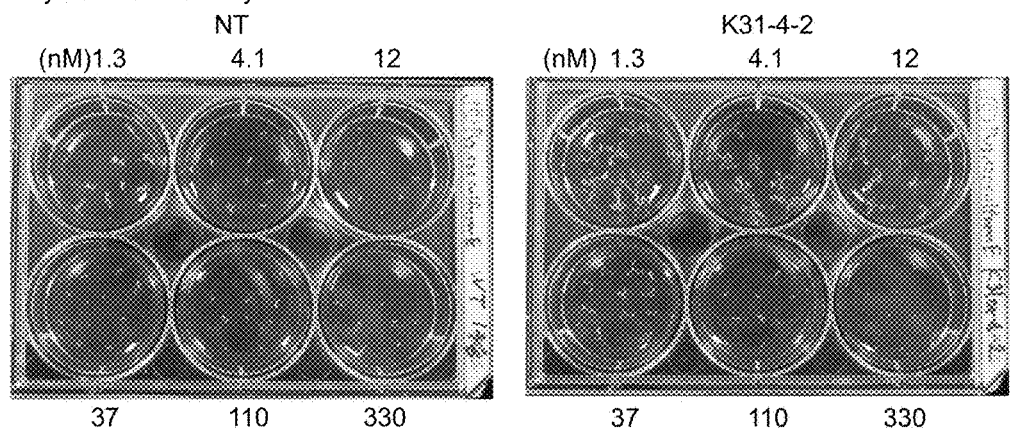
Figure 23:
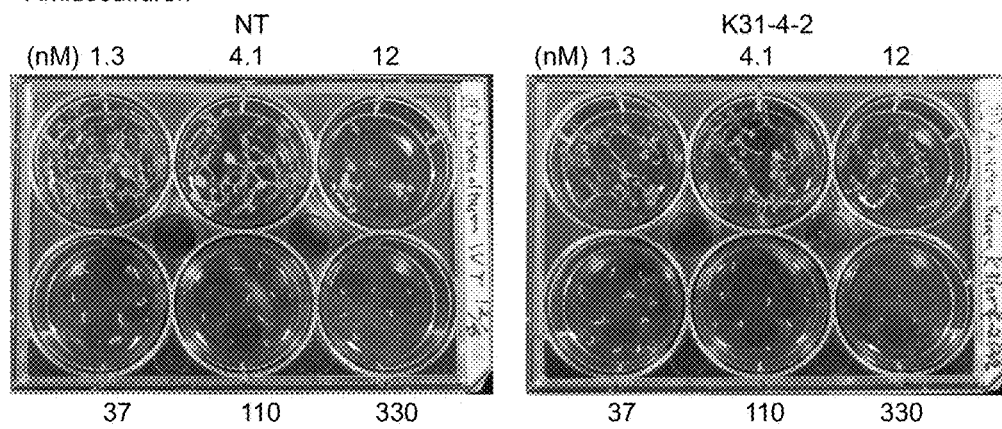
Figure 23:
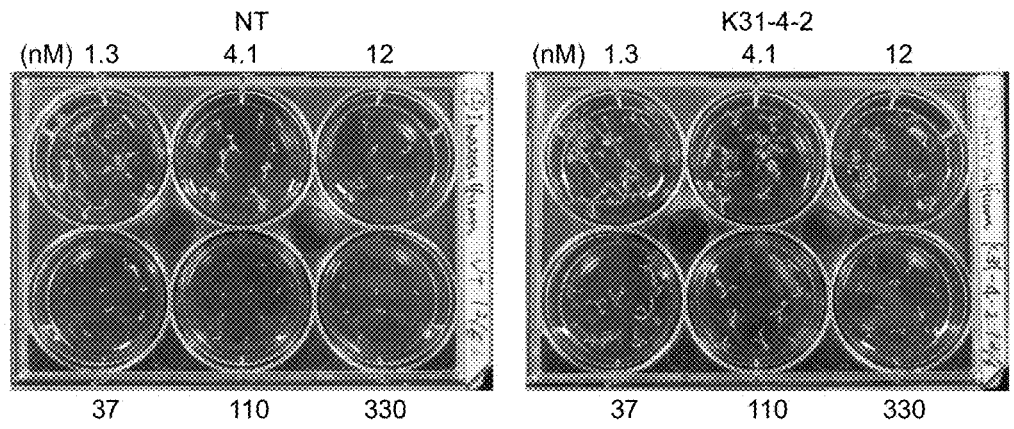

FIG. 23 is a photograph showing the results of a growth test using a pyrazosulfuron-ethyl-containing medium, an amidosulfuron-containing medium, or an imazosulfuron-containing medium on *Arabidopsis thaliana* (K31-4-2) transformed with a Kasalath-derived CYP72A31 gene and non-transformed *Arabidopsis thaliana* (NT).

Figure 24:
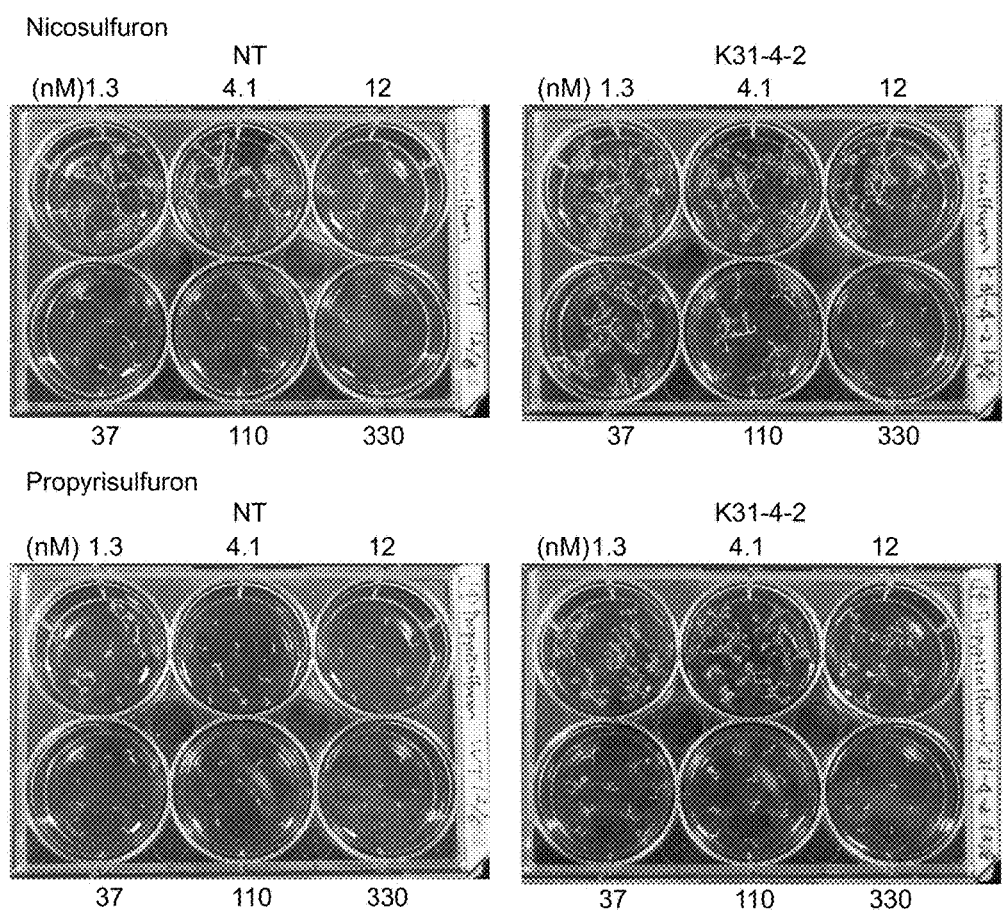

FIG. 24 is a photograph showing the results of a growth test using a nicosulfuron-containing medium, or a propyrisulfuron-containing medium on *Arabidopsis thaliana* (K31-4-2) transformed with a Kasalath-derived CYP72A31 gene and non-transformed *Arabidopsis thaliana* (NT).

Figure 25:
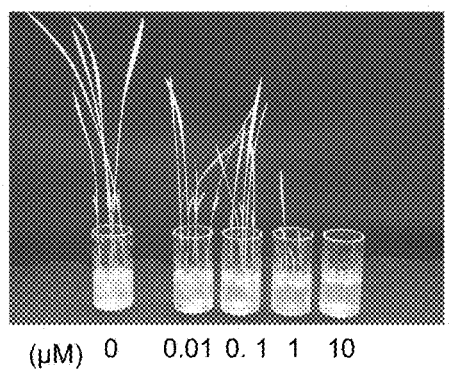
Figure 25:
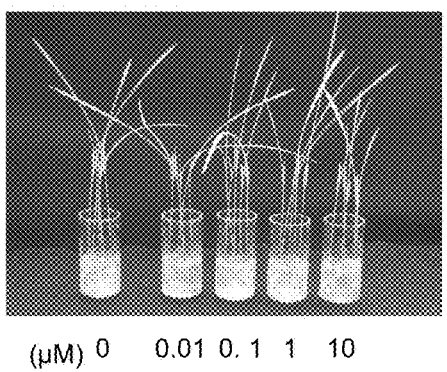
Figure 25:
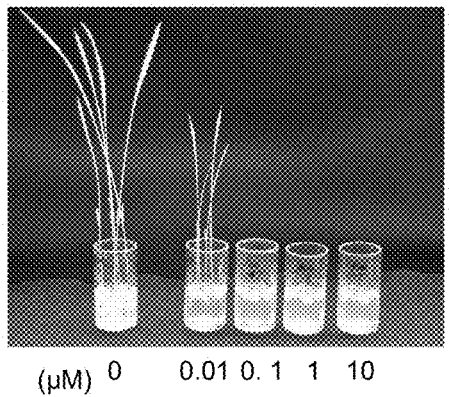
Figure 25:
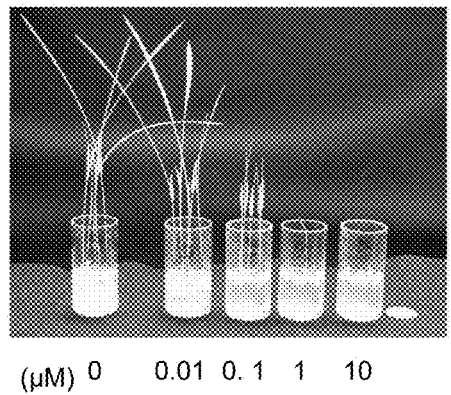

FIG. 25 is a photograph showing the results of a growth test using a BS-containing medium or a pinoxaden-containing medium on rice (K31-4-6-2) transformed with a Kasalath-derived CYP72A31 gene and non-transformed rice (NT).

Figure 26:
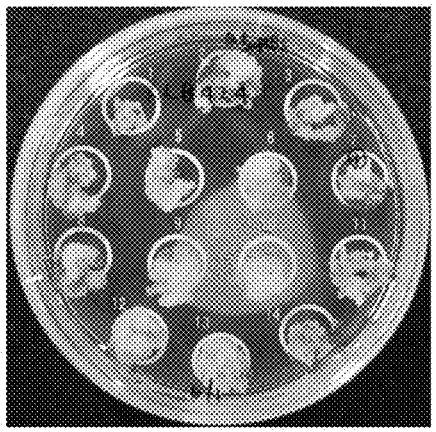
Figure 26:
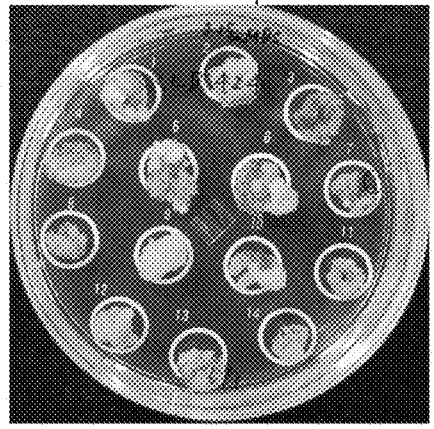
Figure 26:
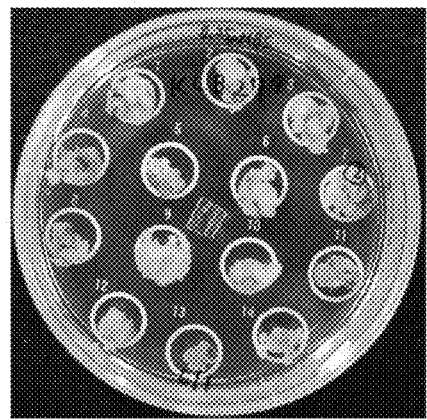

FIG. 26 is a photograph showing the results of a growth test using a BS-containing N6D medium on a rice callus with introduced pCAMBIA1390-KasCYP72A31 or pST-ARA-sGFP.

Figure 27:
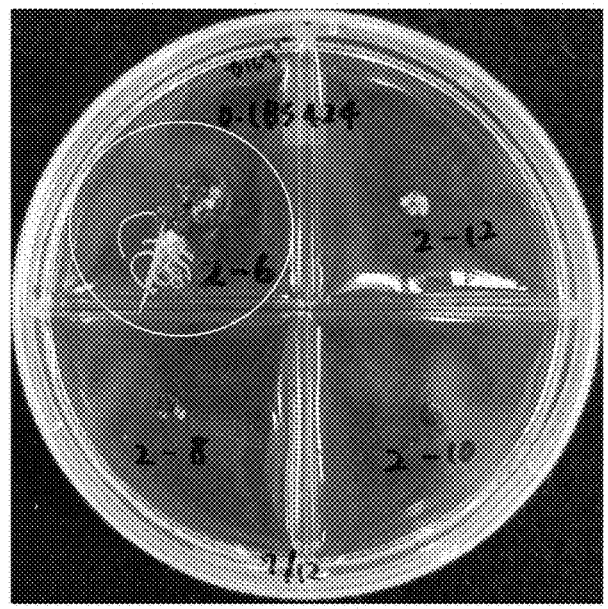

FIG. 27 is a photograph showing the results of a study in which a rice callus with introduced pCAMBIA1390-KasCYP72A31 is selected in BS, followed by redifferentiation.

EMBODIMENTS FOR CARRYING OUT THE INVENTION

The following details the present invention.
1. Cytochrome P450 Gene

A cytochrome P450 gene according to the present invention (hereinafter, simply referred to as a P450 gene) is involved in bispyribac sodium (BS) resistance that Indica rice possesses. This P450 gene is classified into CYP72A31, and has been known as a pseudogene having a 5'-terminal deletion in Nipponbare (a Japonica rice) whose genome sequence has been published. That is, this Japonica rice does not conserve a functional form of Indica rice-derived CYP72A31 identified according to the present invention. Note that this P450 gene classified into CYP72A31 encodes a protein having about 80% amino acid homology with proteins encoded by other cytochrome P450 genes including CYP72A32 and CYP72A33 genes. The cytochrome P450s encoded by these CYP72A32 and CYP72A33 genes fail to exhibit a mechanism of action imparting resistance to BS. Thus, a P450 gene according to the present invention is absent from the Japonica rice and can be identified as a gene responsible for BS resistance possessed by the Indica rice.

Meanwhile, a nucleotide sequence of Indica rice-derived CYP72A31 has been determined, and the DDBJ genomic survey sequence (GSS) database (in other divisions) and the SciFinder database have been searched based on this nucleotide sequence. Then, accession No. CL959279 with a perfect match has been retrieved. This accession No. CL959279, however, has been deposited in the GSS database as a part of the results of Indica rice genome analysis. In addition, the accession No. CL959279 has not been annotated, so that its function cannot be estimated. Also, when a blastp search is performed using, as a query sequence, an amino acid sequence deduced from the nucleotide sequence of Indica rice-derived CYP72A31, accession No. EAY74842 with a perfect match is retrieved. This accession No. EAY74842 has been predicted from an ORF as obtained from the above-described Indica rice genome analysis for registration. Further, the accession No. EAY74842 has an annotation that this peptide is presumed to function as a cytochrome P450. This annotation, however, does not verify that the peptide functions as a cytochrome P450 based on results of expression analysis.

The nucleotide sequence of the cytochrome P450 gene classified into Indica rice-derived CYP72A31 and the amino acid sequence of a protein encoded by the gene are set forth in SEQ ID NOs: 1 and 2, respectively. The cytochrome P450 gene classified into Indica rice-derived CYP72A31 is not limited to those specified by SEQ ID NOs: 1 and 2, and may include genes having a different nucleotide sequence or genes encoding a different amino acid sequence while having a paralog or homolog (i.e., a narrow term) relationship.

Also, the cytochrome P450 gene classified into Indica rice-derived CYP72A31 is not limited to those specified by SEQ ID NOs: 1 and 2, and may include, for example, genes encoding a protein having an amino acid sequence with 70% or higher, preferably 80% or higher, more preferably 90% or higher, and most preferably 95% or higher sequence similarity with the amino acid sequence set forth in SEQ ID NO: 2, the protein having a function of imparting resistance to a plant growth inhibitor by serving as a cytochrome P450. A BLASTN and/or BLASTX program having a BLAST algorithm can calculate a value for the sequence similarity (default settings). Note that the value for the sequence similarity can be calculated as follows: a total number of amino acid residues with a perfect match and amino acid residues with an analogous physicochemical function is calculated while performing a pairwise alignment analysis with paired amino acid sequences; and the value is determined as a ratio of the above total number to the number of all the amino acid residues compared.

Further, the cytochrome P450 gene classified into Indica rice-derived CYP72A31 is not limited to those specified by SEQ ID NOs: 1 and 2, and may include, for example, genes encoding a protein having one or several amino acid substitutions, deletions, insertions, or additions to the amino acid sequence set forth in SEQ ID NO: 2, the protein having a function of imparting resistance to a plant growth inhibitor by serving as a cytochrome P450. As used herein, the term several means, for example, 2 to 30, preferably 2 to 20, more preferably 2 to 10, and most preferably 2 to 5.

Furthermore, the cytochrome P450 gene classified into Indica rice-derived CYP72A31 is not limited to those specified by SEQ ID NOs: 1 and 2, and may include, for example, genes hybridized under stringent conditions with an entire or portion of a strand complementary to a DNA comprising the nucleotide sequence set forth in SEQ ID NO: 1, the genes encoding a protein having a function of imparting resistance to a plant growth inhibitor by serving as a cytochrome P450. As used herein, the term "stringent conditions" means conditions under which what is called a specific hybrid is formed and a non-specific hybrid is not formed. For example, the conditions can be appropriately determined with reference to Molecular Cloning: A Laboratory Manual (Third Edition). Specifically, the stringency can be determined depending on a temperature and a salt concentration of a solution during Southern hybridization and a temperature and a salt concentration of a solution during a washing step of the Southern hybridization. Examples of more specific stringent conditions are described as follows: the sodium concentration is from 25 to 500 mM and preferably from 25 to 300 mM; and the temperature is from 42 to 68 degree C. and preferably from 42 to 65 degree C. Further specifically, the conditions may include 5×SSC (83 mM NaCl, 83 mM sodium citrate) and a temperature of 42 degree C.

As described above, whether or not a gene comprising a nucleotide sequence different from that set forth in SEQ ID NO: 1 or a gene encoding an amino acid sequence different from that set forth in SEQ ID NO: 2 functions as a cytochrome P450 to encode a protein having a function of imparting resistance to a plant growth inhibitor can be verified as follows: the above gene is inserted into an expression vector between an *Agrobacterium tumefaciens*-derived Nos promoter and terminator; the expression vector is used to produce a transformed plant; and it is determined whether or not the transformed plant can grow under conditions in which a non-transformed plant is killed under the presence of a growth inhibitor. Note that bispyribac sodium can be used as a growth inhibitor, but the inhibitor is not particularly limited to bispyribac sodium.

While the specific details are described in Examples, the fact that the cytochrome P450 gene classified into Indica rice-derived CYP72A31 has a function of giving a plant the resistance to a growth inhibitor has been revealed by what is called a map-based cloning. The map-based cloning has been known as a method for examining a difference among similar organisms in sensitivity toward a biologically active substance and other substances. The map-based cloning is a method comprising: narrowing down a candidate chromosome region by using DNA markers based on a detailed gene map; and identifying a gene of interest. Specifically, the Nipponbare (Japonica rice) genome sequence has already been read. Accordingly, a Japonica rice and an Indica rice are crossed to generate varieties. Then, detailed mapping is performed. After that, chromosome segment substitution lines (CSSL) in which a portion is substituted by an Indica rice gene sequence while having a Japonica rice gene sequence as a platform are created. These lines are used to examine a difference in sensitivity toward a substance such as a biologically active substance. This method can specify which region of the chromosome contributes to the difference in the sensitivity to the biologically active substance, etc. Sensitivity toward a substance such as a biologically active substance can be tested by using a germination test and/or a growth test including, for example, a test using a gellan gum medium, a test using an agar medium, a test using a hydroponic culture, and a test using a pot.

Meanwhile, examples of the chromosome segment substitution lines include Koshihikari/Kasalath chromosome segment substitution lines (National Institute of Agrobiological Sciences, Genome Resource Center, http://www.rgrc.dna.affrc.go.jp/jp/ineKKCSSL39.html) and Koshihikari/NonaBokra chromosome portion substitution lines (the above institute, http://www.rgrc.dna.affrc.go.jp/jp/ineKNCSSSL44.html).

2. Expression Vectors

An expression vector according to the present invention can be constructed by ligating (inserting) a cytochrome P450 gene according to the present invention into a suitable vector. The vector for inserting a cytochrome P450 gene according to the present invention thereinto is not particularly limited if the vector can replicate in a host. Examples of the vector include a plasmid, a shuttle vector, and a helper plasmid.

Examples of the plasmid DNA include *Escherichia coli*-derived plasmids (e.g., pBR322, pBR325, pUC118, pUC19, pUC18, pUC19, pBluescript), *Bacillus subtilis*-derived plasmids (e.g., pUB110, pTP5), and yeast-derived plasmids (e.g., YEp13, YCp50). Examples of a phage DNA include λ phages (e.g., Charon4A, Charon21A, EMBL3, EMBL4, λgt10, λgt11, λZAP). In addition, animal viruses such as a retrovirus or a vaccinia virus, or insect virus vectors such as a baculovirus can be used.

In order to insert a cytochrome P450 gene according to the present invention into a vector, a method can be employed, the method comprising: purifying a DNA fragment containing a cytochrome P450 gene; digesting the purified DNA fragment with a suitable restriction enzyme(s); inserting the resulting DNA fragment into a restriction enzyme site or multicloning site of a vector DNA; and ligating the vector.

In an embodiment of the present invention, any gene can be expressed. Accordingly, any additional gene can be inserted into the above expression vector. A technique for inserting any gene is similar to a method for inserting into a vector a cytochrome P450 gene according to the present invention.

Herbicide resistance can be examined after a cytochrome P450 gene according to the present invention is ligated between an *Agrobacterium tumefaciens*-derived Nos promoter and terminator and this construct is introduced into a plant. Note that examples of the promoter can include, in addition to the Nos promoter, a cauliflower mosaic virus 35S promoter (CaMV35S), various actin gene promoters, various ubiquitin gene promoters, a nopaline synthase gene promoter, a tobacco PR1a gene promoter, a tomato ribulose-1,5-diphosphate carboxylase-oxidase small subunit gene promoter, a napin gene promoter, and an oleosin gene promoter. Among them, the cauliflower mosaic virus 35S promoter, actin gene promoters, or ubiquitin gene promoters can be more preferably used.

In such a manner, various vectors can be used in an embodiment of the present invention. In addition, any gene of interest can be linked in a sense or antisense orientation with respect to a cytochrome P450 gene according to the present invention. These genes can be inserted into a vector such as pBI101 (Clontech Laboratories, Inc.) called a binary vector.

3. Producing Transformants

A transformant according to the present invention can be produced by introducing into a host the above-described expression vector according to the present invention. As used herein, examples of the host include, but are not particularly limited to, those capable of expressing a cytochrome P450 gene according to the present invention. Preferred is a plant. When an expression vector according to the present invention is introduced into a host, expression of a cytochrome P450 gene according to the present invention renders resistance to a growth inhibitor. In order to verify whether or not the above-described expression vector according to the present invention has been successfully introduced into a host, the resistance to the growth inhibitor can be used as an indicator for evaluation. That is, a cytochrome P450 gene according to the present invention can be utilized as a selection marker at the time of introducing another gene.

As used herein, plant of transformation subject means any of a whole plant body, a plant organ (e.g., a leaf, petal, stem, root, seed), a plant tissue (e.g., an epidermis, phloem, parenchyma, xylem, vascular bundle), and a plant cultured cell. Examples of the plant that is used for transformation include, but are not limited to, plants (see the following) belonging to a Brassicaceae family, a Poaceae family, a Solanaceae family, a Leguminosae family, or the like.

Brassicaceae family: *Arabidopsis* (*Arabidopsis thaliana*)
Solanaceae family: tobacco (*Nicotiana tabacum*)
Poaceae family: corn (*Zea mays*), rice (*Oryza sativa*)

Leguminosae family: soybean (*Glycine max*)

The above expression vector can be introduced into a plant by using a typical transformation method such as, for example, electroporation, an *Agrobacterium* method, a particle gun method, or a PEG method.

When the electroporation is used, for example, a gene can be introduced into a host by using an electroporator having a pulse controller under conditions at a voltage of 500 to 1600 V, at 25 to 1000 µF, and for 20 to 30 msec.

In addition, when the particle gun method is used, a plant body, a plant organ, or a plant tissue may be used as it is. These materials may be used after preparation of their sections. Also, a protoplast may be prepared and used. Samples as so prepared can be processed by using a gene-introducing device (e.g., PDS-1000/He manufactured by Bio-Rad Laboratories, Inc.). The process conditions differ depending on a plant and its sample. The process, however, is typically performed at a pressure of about 1000 to 1800 psi and at a distance of about 5 to 6 cm.

Also, a cytochrome P450 gene according to the present invention can be introduced into a plant body by using a plant virus as a vector. Examples of the available plant virus include a cauliflower mosaic virus. Specifically, first, a virus genome is inserted into, for example, an *Escherichia coli*-derived vector to prepare a recombinant cell. Then, a cytochrome P450 gene according to the present invention is inserted into the virus genome. The virus genome as so modified is excised from the recombinant cell by using a restriction enzyme. After that, the virus genome can be inoculated with a host plant to introduce into the host plant the cytochrome P450 gene according to the present invention.

In a method using an *Agrobacterium* Ti plasmid, when a plant is infected with bacteria belonging to the genus *Agrobacterium*, a portion of a plasmid DNA of the bacteria is transferred to a plant genome. This characteristic is used to introduce into a host plant a cytochrome P450 gene according to the present invention. A plant is infected with *Agrobacterium tumefaciens* among bacteria belonging to the genus *Agrobacterium* to form a tumor called a crown gall. Also, a plant is infected with *Agrobacterium rhizogenes* to produce hairy roots. These phenomena occur because a region called a T-DNA (Transferred DNA) region on a plasmid called a Ti plasmid or Ri plasmid present in each bacterium is transferred to a plant during its infection and is integrated into a plant genome.

A DNA to be integrated into a plant genome can be inserted into the T-DNA region of the Ti or Ri plasmid. If so, the DNA of interest can be incorporated into the plant genome during the infection of *Agrobacterium* bacteria into a host plant.

As a result of the transformation, the resulting tumor tissue, shoot, or hairy root, for example, can be used, as it is, for a cell culture, tissue culture, or organ culture. In addition, a conventionally known plant tissue culture technique can be used to regenerate a plant body, for example, by administering a suitable concentration of a plant hormone (e.g., auxin, cytokinin, gibberellin, abscisic acid, ethylene, brassinolide).

In one hand, a transformant containing a cytochrome P450 gene according to the present invention is used to screen for a novel plant growth inhibitor. Specifically, a growth-inhibitor candidate substance is made to contact the transformant containing a cytochrome P450 gene according to the present invention. In addition, the same growth-inhibitor candidate substance is made to contact a cell (preferred is a host cell on which the above transformant has been established) not containing the cytochrome P450 gene. Then, a candidate substance is selected which causes the above transformant to proliferate and causes the cell not containing the cytochrome P450 gene to be killed. Accordingly, it can be concluded that the selected candidate substance constitutes a growth inhibitor that is detoxified and metabolized by the cytochrome P450 gene.

The screened growth inhibitor does not have toxicity against a plant with a cytochrome P450 gene according to the present invention, but does have toxicity against a plant without the cytochrome P450 gene. Accordingly, the screened growth inhibitor can be used as an herbicide when a plant with a cytochrome P450 gene according to the present invention is selectively grown.

Meanwhile, an expression vector according to the present invention can be introduced not only into the above host plant, but also into a bacterium, e.g., *Escherichia* such as *Escherichia coli*. *Bacillus* such as *Bacillus subtilis*, *Pseudomonas* such as *Pseudomonas putida*, yeast, e.g., *Saccharomyces cerevisiae, Schizosaccharomyces pombe*, an animal cell, e.g., COS cells, CHO cells, or an insect cell, e.g., Sf9, to produce a transformant. When bacteria such as *Escherichia coli* and yeast are used as a host, it is preferable that an expression vector according to the present invention can self-replicate in the bacteria as well as include a cytochrome P450 gene according to the present invention, a ribosome binding sequence, a gene of interest, and a terminator sequence. Also, the vector may include a gene that regulates the cytochrome P450 gene.

A method for introducing a recombinant vector into a bacterium is not particularly limited if the method is a method for introducing a DNA into a bacterium. Examples of the method include a method using a calcium ion, electroporation, and the like.

When the yeast is used as a host, for example, *Saccharomyces cerevisiae, Schizosaccharomyces pombe*, or other yeast may be employed. A method for introducing a recombinant vector into yeast is not particularly limited if the method is a method for introducing a DNA into yeast. Examples of the method include electroporation, a spheroplast method, a lithium acetate method, and the like.

When the animal cell is used as a host, a monkey cell COS-7, a Vero cell, a Chinese hamster ovary cell (CHO cell), a mouse L cell, or another animal cell may be employed. Examples of a method for introducing a recombinant vector into an animal cell include electroporation, a calcium phosphate method, lipofection, and the like.

When the insect cell is used as a host, Sf9 or another insect cell may be employed. Examples of a method for introducing a recombinant vector into an insect cell include a calcium phosphate method, lipofection, electroporation, and the like.

Whether or not a gene is integrated into a host can be examined by a PCR method, Southern hybridization, Northern hybridization, or the like. For example, a DNA is prepared from a transformant, and DNA-specific primers are designed to carry out a PCR. The PCR is performed using conditions similar to those used for preparation of the above plasmid. Then, an amplification product is subjected to agarose gel electrophoresis, polyacrylamide gel electrophoresis, capillary electrophoresis, or the like. After that, the amplification product is stained with, for example, ethidium bromide or a SYBR Green solution and is detected as a single band. This can verify that a cell has been transformed. In addition, a primer beforehand labeled with, for example, a fluorescent dye can be used to carry out a PCR to detect its amplification product. Further, the amplification product may be immobilized on a solid phase such as a microplate, and fluorescence or an enzymatic reaction, for example, may be used to examine the amplification product. This procedure may be adopted.

4. Producing Plants

As used herein, the above transformed plant cell, for example, can be used to regenerate a transformed plant body. Examples of an employed regeneration method include a method comprising; transferring a callus-like transformed cell into a medium having a modified type and concentration of a hormone to culture the cell; causing the cell to form an adventitious embryo; and producing an intact plant body. Examples of the medium used include an LS medium and an MS medium.

A "method for producing a plant body" according to the present invention includes the steps of: introducing into a host cell a plant expression vector into which a cytochrome P450 gene according to the present invention has been inserted to produce a transformed plant cell; regenerating a transformed plant body from the transformed plant cell; collecting a plant seed from the resulting transformed plant body; and producing a plant body from the plant seed.

In order to obtain a plant seed from a transformed plant body, for example, the transformed plant body is picked up from a rooting medium; the plant body is transferred to a pot with a water-containing soil; the plant body is grown under a constant temperature; a flower is made to bloom; and at last, seeds are formed. Also, in order to produce a plant body from a seed, for example, seeds formed on the transformed plant body are made to mature; then, the resulting seeds are isolated and seeded in a water-containing soil; and the seeds are grown under a constant temperature and illumination to produce a plant body. A plant as so produced exhibits resistance to a growth inhibitor such as an herbicide because of its expression of a cytochrome P450 gene according to the present invention. As used herein, the phrase "exhibits resistance to a growth inhibitor" has the same meaning as that the resistance to a growth inhibitor is exhibited with a statistical difference compared to that before introduction of the cytochrome P450 gene. The resistance to a growth inhibitor can be determined based on, for example, a mortality rate of a plant body and/or a growth inhibition rate of leaves, stems, and roots in contact with the above growth inhibitor having a predetermined concentration.

5. Method for Controlling Harmful Weeds

A cytochrome P450 gene according to the present invention is introduced into a plant, and a transgenic plant is produced according to the above method. By doing so, a plant can be produced which has resistance to a growth inhibitor. Thus, for example, this transgenic plant can be created for a useful plant; when the transgenic plant is cultivated in a field, the entire field is treated with, for example, a weed-killing substance such as an herbicide; and only weeds can be controlled without causing herbicide injury on the transgenic plant.

6. Growth Inhibitor

As used herein, the term growth inhibitor refers to, but is not particularly limited to, a substance having an inhibitory effect on plant growth. As used herein particularly, the growth inhibitor means those involved in detoxification and metabolism mediated through a cytochrome P450 encoded by a cytochrome P450 gene according to the present invention. For example, a preferable growth inhibitor is a substance having a significantly higher inhibitory effect on a plant (e.g., a Japonica rice) without an intrinsic cytochrome P450 gene according to the present invention than that on an Indica rice with the intrinsic cytochrome P450 gene.

Specific examples of the growth inhibitor include agrochemicals, e.g., an herbicide, a plant growth regulator, a microbicide, a pesticide, a miticide, a nematicide, a rodenticide, agriculture and horticulture materials, e.g., a fertilizer, a plant activator, a microbe-derived substance harmful to a plant, an animal e.g., an arthropod, a nematode, -derived substance harmful to a plant, an allelopathy-causing plant-derived substance harmful to a plant, and other substances, included in the soil, water, or air, that are harmful to a plant.

Examples of the herbicide contained in the growth inhibitor include bispyribac sodium (BS). The BS is a chief component of any of Grass short, a product name (a registered trademark), and Nominee ("Nominee (in Japanese)" and Nominee are registered trademarks), and has an herbicide activity. The Grass short has been used as an anti-weed agent for ridges between paddy fields and a non-agricultural land. In contrast, the Nominee has been used as an herbicide for paddy fields where an Indica rice variety is cultivated. The Nominee, however, causes herbicide injury on a Japonica rice variety. Hence, the Nominee is used exclusively in ridges between paddy fields.

The BS targets an acetolactate synthase ((ALS), EC 2.2.1.6, also referred to as an acetohydroxy acid synthase (AHAS)), and inhibits this enzyme to lead to a plant's death. The Japonica rice and Indica rice varieties vary in 4 amino acids within their amino acid sequences of the ALS protein of a target enzyme. This variation is different from an amino acid substitution involved in resistance to an ALS inhibitor. Thus, this difference is not responsible for the reason why the Indica rice variety has a higher resistance to BS (Aldo Merotto et al., J. Agric. Food Chem., 57, 4, 1389-1398 (2009)).

In contrast, regarding the BS detoxification and metabolism in a Japonica rice variety, it has been known that a methoxy group on a pyrimidine ring of BS is oxidized and converted into a hydroxyl group to inactivate its enzyme inhibitory activity (Matsushita et al., the proceedings of the 19th Conference of Pesticide Science Society of Japan, C-115, 127 (1994)). While BS is a pyrimidinyl-salicylic-acid-based ALS inhibitor, CYP81A6 has been known as a cytochrome P450 which metabolizes a sulfonylurea-based ALS-inhibitory herbicide (JP Patent Publication (Kohyo) No. 2008-546419A). Unfortunately, it remains unclear which portion of the sulfonylurea-based ALS-inhibitory herbicide the CYP81A6 oxidizes and inactivates. Also, the CYP81A6 gene is reportedly present in each of the Indica rice variety and Nipponbare rice variety (CIB-DDBJ, NCBI, ENA/EBI Accession No. DQ341412 (an Indica rice variety), AK104825 (a Japonica rice variety)). It cannot be concluded that the BS resistance in the Indica rice variety is caused by a cytochrome P450 gene classified into the CYP81A6.

Thus, the below-described Examples conclusively demonstrates that the BS resistance in the Indica rice variety is caused by a cytochrome P450 gene classified into Indica rice-derived CYP72A31. In addition, the cytochrome P450 gene classified into Indica rice-derived CYP72A31 can be said to be involved in decomposition and metabolism of not only BS but also various herbicides.

Specific examples of the herbicide can include, but are not limited to, 2,3,6-TBA, 2,4-D (including salts with amine, diethylamine, triethanolamine, isopropylamine, sodium, or lithium), 2,4-DB, 2,4-PA, ACN, AE-F-150944 (code number), CAT, DBN, DCBN, DCMU, DCPA, DNOC (including salts with amine or sodium), DPA, EPTC, IPC, MCPA, MCPA.isopropylamine salts, MCPA.ethyl, MCPA.sodium, MCPA.thioethyl, MCPB, MCPP, MDBA, MDBA.isopropylamine salts, MIBA.sodium salts, PAC, SAP, S-metolachlor, SYP-298 (code number), SYP-300 (code number), TCA (including salts with sodium, calcium, or ammonia), TCTP, ioxynil, ioxynil-octanoate, aclonifen, acrolein, azafenidin, acifluorfen-sodium, azimsulfuron, asulam, acetochlor, atrazine, anilofos, amicarbazone, amidosulfuron, amitrole, aminopyralid, amiprofs-methyl, ametryn, alachlor, alloxydim, ancymidol, isouron, isoxachlortole, isoxaflutole, isoxaben, isoproturon, ipfencarbazone, imazaquin, imazapic (including salts with amine), imazapyr (including salts with isopropylamine), imazamethabenz-methyl, imazamox (including salts with an amine salt), imazethapyr (including salts with an amine salt), imazosulfuron, indaziflam, indanofan, esprocarb, ethametsulfuron-methyl, ethalfluralin, ethidimuron, ethoxysulfuron, ethoxyfen-ethyl, ethofumesate, etobenzanid, endothal-disodium, oxadiazon, oxadiargyl, oxaziclomefone, oxasulfuron, oxyfluorfen, oryzalin, orthosulfamuron, orbencarb, cafenstrole, carfentrazone-ethyl, karbutilate, carbetamide, quizalofop-P-ethyl, quizalofop-P-tefuryl, quizalofop-ethyl, quinoclamine, quinclorac, quinmerac, cumyluron, glyphosate (including salts with sodium, potassium, amine, propylamine, isopropylamine, dimethylamine, or trimesium), glufosinate (including salts with amine or sodium), clethodim, clodinafop-propargyl, clopyralid, clomazone, chlomethoxyfen, clomeprop, cloransulammethyl, chloramben, chloridazon, chlorimuron-ethyl, chlorsulfuron, chlorthal-dimethyl, chlorthiamid, chlorphthalim, chlorflurenol (including lower alkyl ester), chlorpropham, chlorbromuron, chlormequat, chloroxuron, chlorotoluron, saflufenacil, cyanazine, diuron, dicamba (including salts with amine, diethylamine, isopropylamine, diglycolamine, sodium, or lithium), cycloate, cycloxydim, diclosulam, cyclosulfamuron, dichlobenil, diclofop-methyl, dichlorprop, dichlorprop-P, diquat-dibromide, dithiopyr, siduron, dinitramine, cinidon-ethyl, cinosulfuron, dinoterb, cyhalofop-butyl, diphenamid, difenzoquat, diflufenican, diflufenzopyr, diflumetorim, simazine, dimethachlor, dimethametryn, dimethenamid, simetryn, dimepiperate, dimefuron, cinmethylin, sulcotrione, sulfentrazone, sulfosulfuron, sulfometuron-methyl, sethoxydim, terbacil, diaimuron, dalapon, thiazopyr, thiencarbazone, tiocarbazil, thiobencarb, thidiazimin, thidiazuron, thifensulfuron-methyl, n-decanol, desmedipham, desmetryne, tetrapion, thenylchlor, tebutam, tebuthiuron, tepraloxydim, tefuryltrione, terbuthylazine, terbutryn, terbumeton, tembotrione, topramezone, tralkoxydim, triaziflam, triasulfuron, ti-allate, trietazine, triclopyr-butotyl, tritosulfuron, triflusulfuron-methyl, trifluralin, trifloxysulfuron-sodium, tribenuron-methyl, naptalam (including salts with sodium), naproanilide, napropamide, nicosulfuron, neburon, norflurazon, vernolate, paraquatdichloride, haloxyfop-methyl, haloxyfop-P-methyl, halosulfuron-methyl, bilanafos-sodium, picloram, picolinafen, bicyclopyrone, bispyribac-sodium, pinoxaden, bifenox, piperophos, pyraclonil, pyrasulfotole, pyrazoxyfen, pyrazosulfuron-ethyl, pyrazolynate, pyraflufen-ethyl, pyridafol, pyrithiobac-sodium, pyridate, pyriftalid, pyributicarb, pyribenzoxim, pyrimisulfan, pyriminobac-methyl, pyroxasulfone, pyroxsulam, fenuron, fenoxasulfone, fenoxaprop-P-ethyl, fenoxaprop-ethyl, fenclorim, fenthiaprop-ethyl, fentrazamide, phenmedipham, foramsulfuron, butachlor, butafenacil, butamifos, butylate, butralin, butroxydim, flazasulfuron, flamprop-methyl, flamprop-methyl, flamprop-ethyl, flamprop-isopropyl, flamprop-M-isopropyl, primisulfuron-methyl, fluazifop-butyl, fluazifop-P-butyl, fluazolate, fluometuron, fluoroglycofen-ethyl, flucarbazone-sodium, flucetosulfuron, fluthiacet-methyl, flupyrsulfuron-methyl-sodium, flufenacet, flufenpyr-ethyl, flupropanate-sodium, flupoxam, flumioxazin, flumiclorac-pentyl, flumetsulam, fluridone, flurtamone, flurprimidol, fluroxypyr, flurochloridone, pretilachlor, prodiamine, prosulfuron, prosulfocarb, propaquizafop, propachlor, propazine, propanil, propyzamide, propisochlor, propyrisulfuron, propham, profluazol, propoxycarbazone-sodium, profoxydim, bromacil, prometryn, prometon, bromoxyni (including esters with butyric acid, octanoic acid, or heptanoic acid), bromobutide, florasulam, hexazinone, benefin, pethoxamid, benazolin, penoxsulam, beflubutamid, pebulate, bencarbazone, benzfendizone, bensulide, bensulfuron-methyl, benzobicyclon, benzofenap, bentazone (including salts with sodium), pentanochlor, benthiocarb, pendimethalin, pentoxazone, benfluralin, benfuresate, fosamine-ammonium, fomesafen, forchlorfenuron, maleichydrazide, mecoprop-potassium, mecoprop-P, mesosulfuron-methyl, mesotrione, metazachlor, methabenzthiazuron, metazosulfuron, metamitron, metamifop, methyldymron, metoxuron, metosulam, metsulfuron-methyl, metobromuron, metobenzuron, metolachlor, metribuzin, mepiquat-chloride, mefenacet, monolinuron, molinate, iodosulfulon-methyl-sodium, lactofen, linuron, rimsulfuron, lenacil, and the like.

Specific examples of the plant growth regulator can include, but are not limited to, α-naphthaleneacetamide, 1-methylcyclopropene, 2,6-diisopropylnaphthalene, 4-CPA, aviglycine, abscisic acid, ancymidol, inabenfide, indole acetic acid, indole butyric acid, uniconazole-P, ethychlozate, ethephon, oxine-sulfate, carvone, calcium formate, cloxyfonac-sodium, cloxyfonac-potassium, cloprop, chlormequat, choline, cytokinins, cyanamide, cyclanilide, dichlorprop, dikegulac, gibberellin, dimethipin, sintofen, daminodide, n-decyl alcohol, 1-triacontanol, trinexapac-ethyl, paclobutrazol, paraffin, pyraflufen-ethyl, butralin, flumetralin, flurprimidol, flurenol, prohydrojasmon, prohexadione-calcium, (6-)benzylaminopurine, pendimethalin, forchlorfenuron, maleic hydrazide, mepiquat-chloride, mefluidide, wax, MCPA.thioethyl, MCPB, 4-CPA, calcium chloride, calcium sulfate, calcium peroxide, extract from chlorella, extract from mixed herbal medicine, and the like.

Specific examples of the microbicide can include, but are not limited to, BAG-010 (code number), BAF-045 (code number), copper dioctanoate, DBEDC, SYP-Z-048 (code number), TPTA, TPTC, TPTH, acibenzolar-S-methyl, azoxystrobin, amisulbrom, aldimorph, isotianil, isopyrazam, isoprothiolane, ipconazole, iprodione, iprovalicarb, iprobenfos, imazalil, iminoctadine-albesilate, iminoctadine-triacetate, imibenconazole, echlomezole, edifenphos, ethaboxam, edifenphos, ethoxyquin, etridiazole, enestroburin, epoxiconazole, oxadixyl, oxazinylazole, oxycarboxin, oxytetracycline, oxpoconazole-fumarate, oxolinic acid, octhilinone, ofurace, orysastrobin, o-phenylphenol, kasugamycin, captafol, carpropamid, carbendazim, carboxin, quinoxyfen, chinomethionat, captan, quintozene, guaxatine, kresoximmethyl, chloroneb, chlorothalonil, cyazofamid, diethofencarb, diclocymet, dichlofluanid, diclomezine, dicloran, dithianon, diniconazole, zineb, dinocap, diphenyl, diphenylamine, difenoconazole, difenzoquat metilsulfate, cyflufenamid, diflumetorim, cyproconazole, cyprodinil, simeconazole, dimethomorph, cymoxanil, dimoxystrobin, ziram, silthiofam, streptomycin, spiroxamine, sedaxane, zoxamide, dazomet, thiadiazin, tiadinil, thiabendazole, thiram, thiophanate-methyl, thifluzamide, tecnazene, tecloftalam, tetraconazole, debacarb, tebuconazole, tebufloquin, dodine, dodemorph, triadimenol, triadimefon, triazoxide, tricyclazole, triticonazole, tridemorph, triflumizole, trifloxystrobin, triforine, tolylfluanid, tolclofos-methyl, tolnifanide, nabam, nitrothal-isopropyl, nuarimol, validamycin, valifenalate, bixafen, picoxystrobin, bitertanol, hydroxyisoxazole, piperalin, hymexazol, pyraclostrobin, pyrazophos, pyriofenone, pyrifenox, pyributicarb, pyribencarb, pyrimethanil, pyroquilon, vinclozolin, ferbam, famoxadone, phenazine oxide, fenamidone, fenarimol, fenoxanil, ferimzone, fenbuconazole, fenfurum, fenpropidin, fenpropimorph, fenhexamid, folpet, phthalide, bupirimate, fuberidazole, blasticidin-S, furametpyr, furalaxyl, fluazinam, fluoxastrobin, fluopicolide, fluopyram, fluoroimide, fluquinconazole, fludioxonil, flusilazole, flusulfamide, flutianil, flutolanil, flutriafol, flumorph, proquinazid, prochloraz, procymidone, prothioconazole, bronopol, propamocarb-hydrochloride, propiconazole, propineb, probenazole, bromuconazole, hexaconazole, benalaxyl, benalaxyl-M, benomyl, pefurazoate, penconazole, pencycuron, benthiavalicarb-isopropyl, penthiopyrad, penflufen, boscalid, fosetyl-alminium, polyoxin, polycarbamate, mancopper, mandipropamid, mancozeb, maneb, myclobutanil, mildiomycin, methasulfocarb, metam, metalaxyl, metalaxyl-M, metconazole, metominostrobin, metrafenone, mepanipyrim, mepronil, oxyquinoline sufate, silver, Bordeaux mixture, copper compounds, e.g., copper oxychloride, cuprous oxide, copper hydroxide, copper sulfate, oxine-copper, and copper (nonylphenyl)sulphonate, sulfur compounds, potassium bicarbonate, sodium bicarbonate, fatty acid glyceride, extract from *Lentinula edodes* mycelium, and the like.

Specific examples of the pesticide, miticide, or nematicide can include, but are not limited to, 1,3-dichloropropene, BPMC, BPPS, BRP, CL900167 (code number), cryolite, CVMP, CYAP, D-D, DCIP, DDVP, DEP, DMTP, DNOC, ECP, EPN, MEP, MIPC, MPP, NAC, Ammonium N-methyldithiocarbamate (NCS), NI-30) (code number), NNI-0101, PAP, PHC, RU15525 (code number), thiazosulfen, XMC, ZXI-8901 (code number), acrinathrin, azamethiphos, azinphos-ethyl, azinphos-methyl, acequinocylacetamiprid, acetamiprid, acetoprol, acephate, azocyclotin, abamectin, amitraz, alanycarb, aldicarb, alpha-cypermethrin, allethrin, isocarbophos, isoxathion, isofenphos-methyl, isoprocarb, imicyafos, imidacloprid, imiprothrin, indoxacarb, esfenvalerate, ethiofencarb, ethion, ethiprole, disulfoton, etoxazole, etofenprox, ethoprophos, emamectin, endosulfan, empenthrin, oxamyl, oxydemeton-methyl, omethoate, sodium oleate, metam-sodium, cadusafos, kadethrin, karnjin, cartap, carbaryl, carbosulfan, carbofuran, gamma-cyhalothrin, xylylcarb, quinalphos, kinoprene, chinomethionat, coumaphos, clothianidin, clofentezine, chromafenozide, chlorethoxyfos, chlorantraniliprole, chlordane, chloropierin, chlorpyrifos, chlorpyrifos-methyl, chlorfenapyr, clofentezine, chlorfenvinphos, chlorfluazuron, chromafenozide, chlormephos, cyenopyrafen, cyazypyr, cyanophos, diafenthiuron, cyantraniliprole, dienochlor, cyenopyrafen, dicrotophos, dichlofenthion, cycloprothrin, dicofol, dicyclanil, disulfoton, dinotefuran, dinobuton, cyhalothrin, cyphenothrin, cyfluthrin, diflubenzuron, cyflumetofen, diflovidazin, cyhexatin, cypermethrin, dimethylvinphos, dimethoate, silafluofen, cyromazine, spinosad, spinetoram, spirodiclofen, spirotetramat, spiromesifen, sulcofuron-sodium, sulfluramid, sulprofos, sulfoxaflor, sulfotep, zeta-cypermethrin, diazinon, tau-fluvalinate, thiacloprid, thiamethoxam, thiodicarb, thiocyclam, thiosultap, thiofanox, thiometon, tetrachlorvinphos, tetradifontetramethrin, tetramethrin, tebupirimfos, tebufenozide, tebufenpyrad, tefluthrin, teflubenzuron, demeton-S-methyl, temephos, rotenone, deltamethrin, terbufos, tralomethrin, transfluthrin, triazamate, triazophos, trichlorfon, triflumuron, trimethacarb, tolfenpyrad, naled, nicotine, nitenpyram, nemadectin, novaluron, noviflumuron, hydroprene, vamidothion, parathion, parathion-methyl, halfenprox, halofenozide, bioallethrin, bioresmethrin, bistrifluoron, hydramethylnon, bifenazate, bifenthrin, pymetrozine, pyraclofos, pyridaphenthion, pyridaben, pyridalyl, pyrifluquinazon, pyriproxyfen, pirimicarb, pyrimidifen, pirimiphos-methyl, pyrethrins, famphur, fipronil, fenazaquin, fenamiphos, phenisobromolate, fenitrothion, fenoxycarb, fenothiocarb, phenothrin, fenobucarb, fenthion, phenthoate, fenvalerate, fenpyroximate, fenbutatinoxide, fenpropathrin, butocarboxim, butoxycarboxim, buprofezin, furathiocarb, prallethrin, fluacrypyrim, flucycloxuron, flucythrinate, flusulfamide, fluvalinate, flupyrazofos, flufenerim, flufenoxuron, flubendiamide, flumethrin, flurimufen, prothiofos, flonicamid, propaphospropargiteprofenofos, propoxur, propetamphos, propoxur, bromopropylate, beta-cypermethrin, beta-cyfluthrin, hexaflumuron, hexythiazox, heptenophos, permethrin, bensultap, endosulfan, benzoximate, bendiocarb, benfuracarb, phoxim, phosalone, fosthiazate, phosphamidon, phosmet, formetanate, phorate, petroleumoils, malathion, milbemectinmecarbam, mecarbam, mesulfenfos, methomyl, metaldehyde, metaflumizon, methamidophos, metham-potassium, metham-ammonium, methiocarb, methidathion, methylisothiocyanate, methoxychlor, methoxyfenozide, methothrin, metofluthrin, methoprene, metholcarb, mevinphos, monocrotophos, lambda-cyhalothrin, chlorantraniliprole, lufenuron, resmethrin, lepmectin, rotenone, propylene glycol monolaurate, nicotine sulfate, levamisol, ethylene oxide, fenbutatin oxide, fatty acid glyceride, morantel tartrate, canola oil, starch, soybean lecithin, *Bacillus thuringiensis*-derived crystalline proteins, and the like.

Examples of the fertilizer can include, but are not limited to, nitrogenous fertilizers, phosphatic fertilizers, potassium fertilizers, organic fertilizers, calcareous fertilizers, magnesium fertilizers, manganese fertilizers, boracic fertilizes, chemical fertilizers, mixed fertilizers, and the like.

Specific examples of the microbe-derived substance harmful to a plant can include, but are not limited to, pathogenic bacteria-derived tropolone and the like.

Specific examples of the plant-derived substance harmful to a plant can include, but are not limited to, a cis-dehydromatricaria ester that is released from roots of *Solidago altissima* and the like.

All these substances are publicly known and/or commercially available. Otherwise, a process for producing each substance is described in a published literature.

EXAMPLES

The following details the present invention with reference to Examples. The technical scope of the present invention, however, is not limited to the following Examples.

Example 1

Screening for Bispyribac-Sodium-Resistant Variety SL202 Backcrossed Between Koshihikari/Kasalath First, 39 varieties of Koshihikari/Kasalath chromosome segment substitution lines (CSSL, obtained from the Rice Genome Resource Center, National Institute of Agrobiological Sciences, Ebitani et al., Breed. Sci., 55, 65-73 (2005)) as produced by backcrossing Koshihikari/Kasalath were used to perform a test for bispyribac sodium (BS) sensitivity. The BS sensitivity was examined by a growth test using a 1 µM-BS-containing gellan gum medium.

Figure 1:
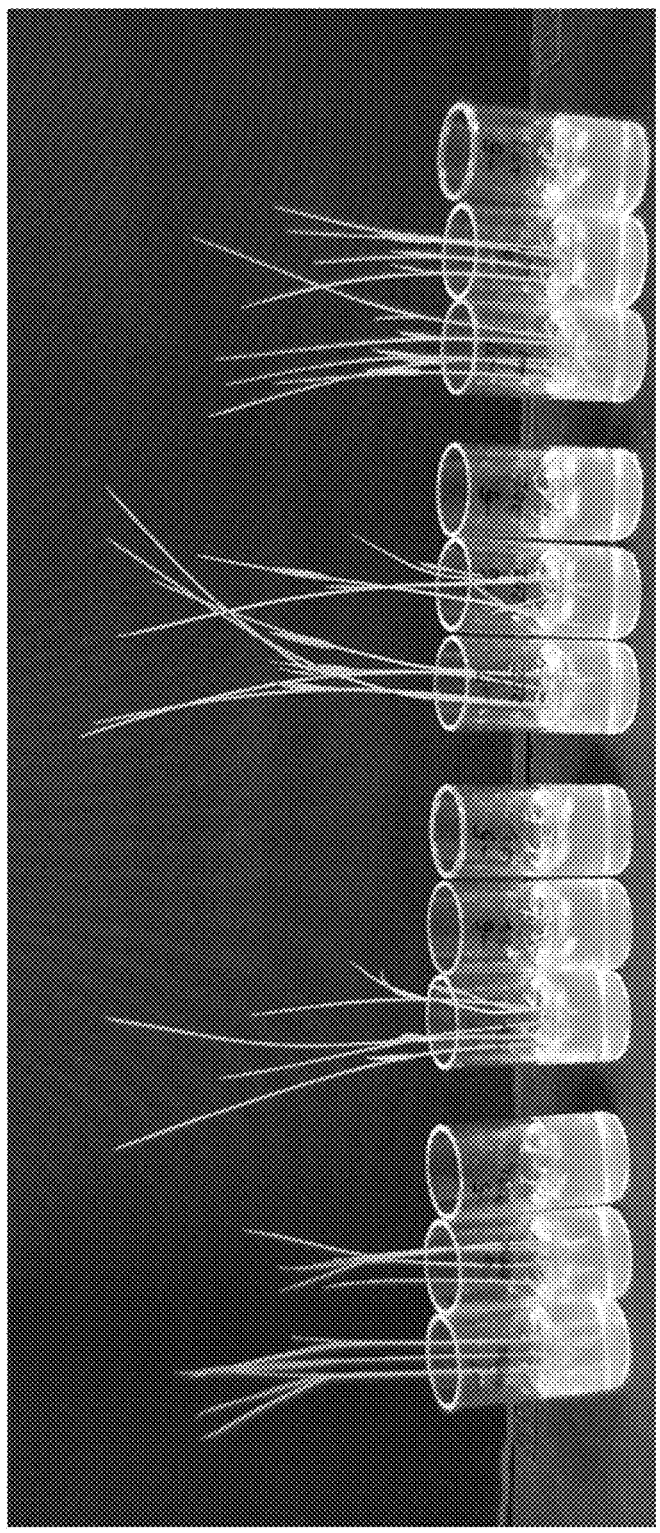
FIG. 1 is a photograph showing the results of growing Koshihikari, Kasalath, and Koshihikari/Kasalath chromosome segment substitution lines in a BS-containing medium.

Next, 1.6 g of Hoagland's mix (Sigma-Aldrich Corporation) and 3 g of Gelrite (Wako Pure Chemical Industries, Ltd.) were suspended in 1 L of distilled water. Then, the mixture was dissolved and heated in a microwave. After that, the mixture was cooled to 50 to 60 degree C., and BS was added at a final concentration of 1 µM. This mixture was dispensed into 30-mL tubular bottles at 15 mL to prepare a gellan gum medium. Next, CSSL rice paddies were soaked in 0.5% sodium hypochlorite for about 20 minutes, and were then washed well with water. These paddies were soaked in distilled water, and kept at 27 degree C. for 3 to 5 days for germination. Germinating seeds were softly planted in sprout-side up on the gellan gum medium. These samples, together with a beaker filled with distilled water, were placed in a transparent case, which was then covered with a clear-plastic wrap. These samples were grown at 27 degree C. under fluorescent light illumination (14 hours of a light period and 10 hours of a dark period) for 7 to 9 days. Of seeds from 39 varieties used, varieties SL201 and SL202 whose portion of Koshihikari chromosome 1 had been replaced by an equivalent portion of Kasalath chromosome 1 exhibited an equivalent degree of resistance to BS to that of Kasalath (FIG. 1).

Example 2

Screening F2 Offspring as Obtained by Backcrossing Between SL202 and Koshihikari for BS-Resistant Plants and Data Mining Regarding Bispyribac-Sodium-Resistant Cytochrome P450 Gene While varieties SL201 and SL202 were bispyribac sodium resistant, the variety SL202 was used in the following experiments. First, 190 offspring of F2 offspring as obtained by backcrossing between SL202 and Koshihikari were examined for their BS sensitivity. The procedure was carried out according to a BS sensitivity test using the gellan gum as described in Example 1.

Figure 2:
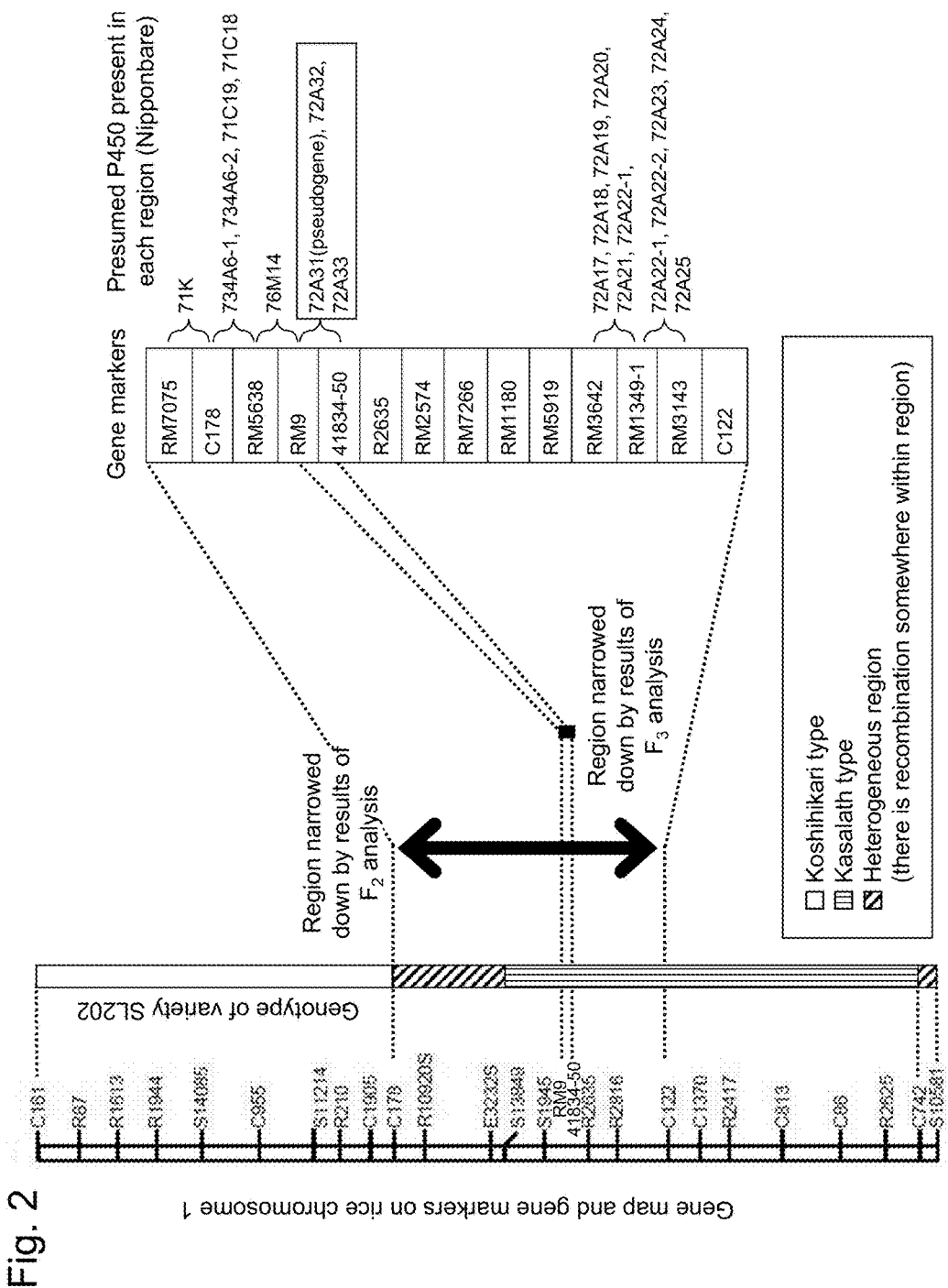
FIG. 2 illustrates the results of investigating a gene responsible for BS resistance by using chromosomal location mapping.
Figure 3:
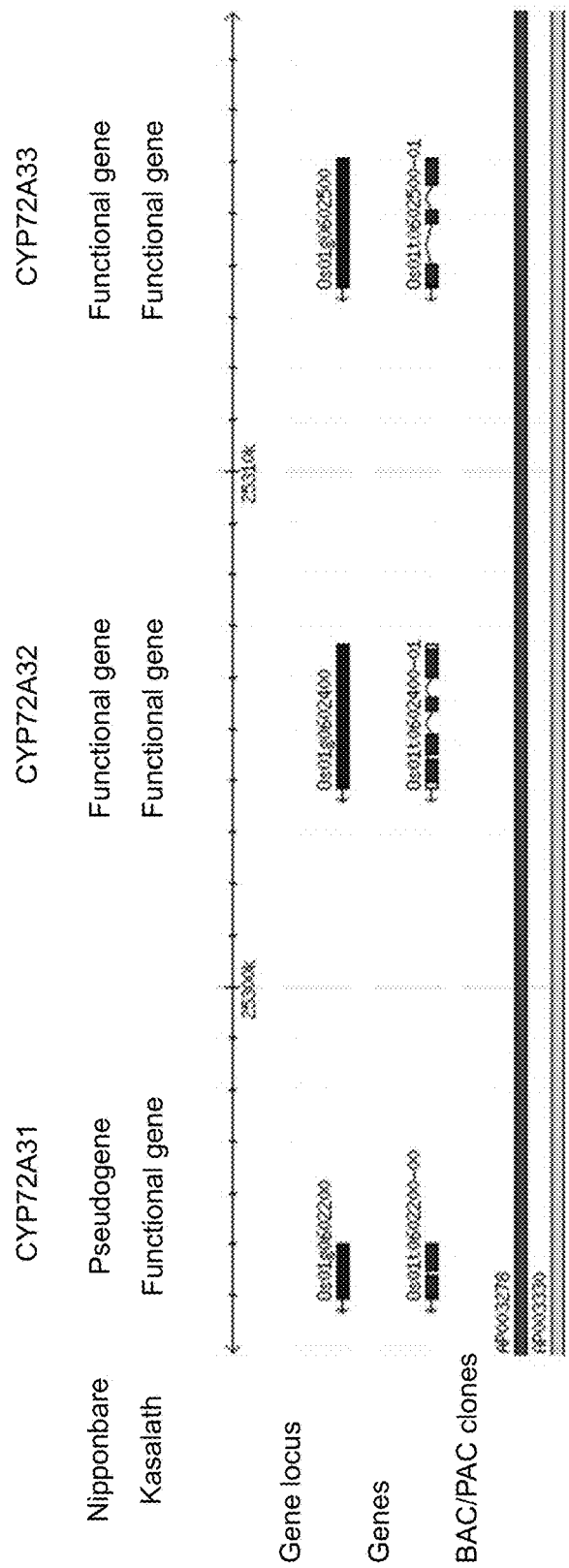
FIG. 3 is a diagram featuring three P450 members positioned between markers RM9 to 41834-50 on chromosome 1.

The results indicated that 138 offspring of 190 offspring tested were BS-resistant. This demonstrated that a gene involved with the BS resistance was located on a single gene locus and was dominantly inherited. Subsequently, 80 offspring exhibiting the BS resistance were used to examine whether a genotype of marker portions (R2635, C122, R2417, C86) on chromosome 1 was a Koshihikari or Kasalath type. Then, the R2635 was homozygous for a Kasalath-type allele or heterozygous between Kasalath- and Koshihikari-type alleles. In contrast, the markers C122, R2417, and C86 were homozygous for a Koshihikari-type allele, homozygous for a Kasalath-type allele, and heterozygous between Kasalath- and Koshihikari-type alleles. A region from C161 to C178, a marker for the variety SL202, was a Koshihikari type, and the other regions were either a Kasalath-type allele or a region containing both Kasalath- and Koshihikari-type alleles. Thus, a BS-resistant gene seemed to be positioned in a gene region between the markers C178 and C122 on chromosome 1 of the variety SL202. Further, the next generation (F3 generation) offspring were produced by breeding plants whose gene region between C178 and C122 was considered to have a heterozygous genotype containing Kasalath- and Koshihikari-type alleles. The offspring were used to examine the BS sensitivity according to a BS sensitivity test using the gellan gum as described in Example 1. Of 925 offspring examined, 418 offspring exhibited the BS resistance. Among them, BS-resistant 258 offspring were used to investigate whether the genotype of the marker portions (RM7075, C178, RM5638, RM9, 41834-50, R2635, RM2574, RM17266, RM1180, RM5919, RM3642, RM1349-1, RM3143, C122) on chromosome 1 is a Koshihikari or Kasalath type. The results demonstrated that the markers RM9 and 41834-50 were homozygous for a Kasalath-type allele or heterozygous between Kasalath- and Koshihikari-type alleles, and there was no offspring homozygous for the Koshihikari-type allele. Hence, the responsible gene seemed to be present between the markers RM9 and 41834-50 on chromosome 1 within about 372-kb distance (FIG. 2). Published genome information (The Rice Annotation Project Database (RAP-BD), http://rapdb.dna.affrc.go.jp/) regarding Nipponbare suggested that this region contains three P450 genes (Os01g0602200, Os01g0602400, Os01g0602500) (FIG. 3).

Figure 4:
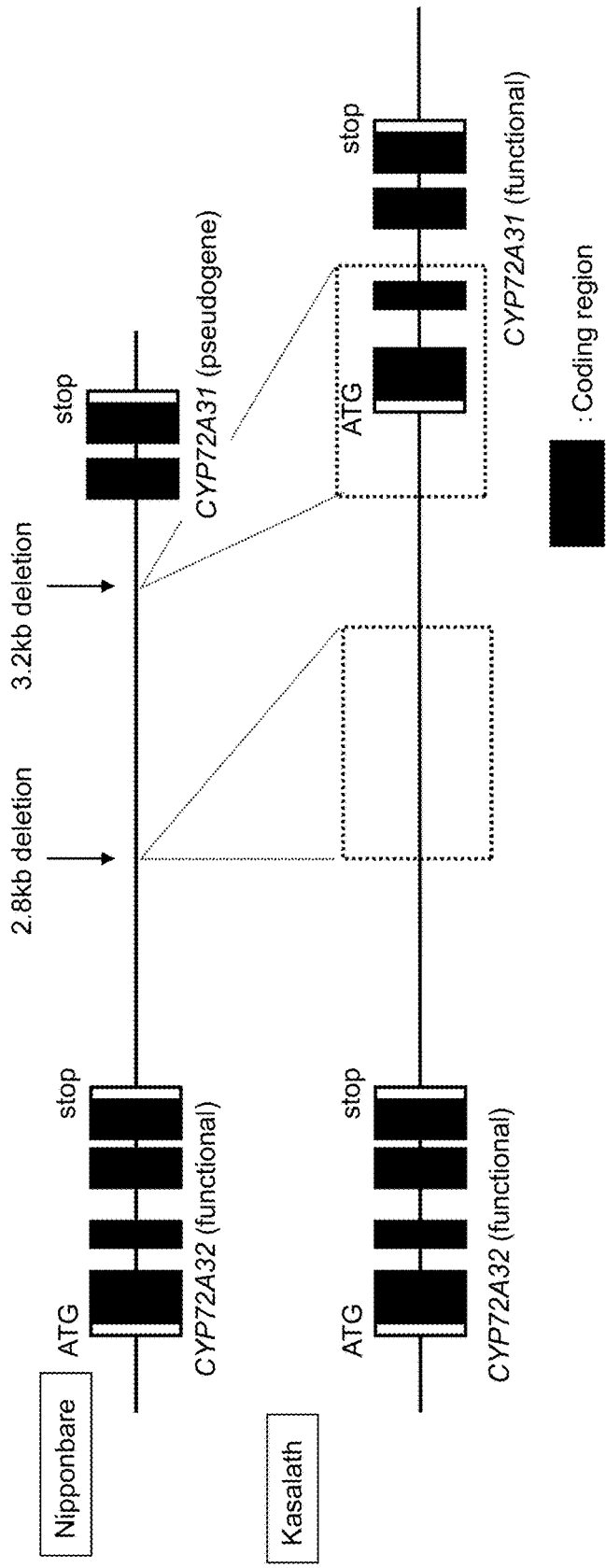
FIG. 4 illustrates the results of comparison between Kasalath and Nipponbare CYP72A31 genes.

The P450 annotation information (a Cytochrome P450 homepage, http://drnelson.uthsc.edu/rice.html) indicated that these three genes are CYP72A31 (pseudogene), CYP72A32, and CYP72A33. These genes were compared and analyzed between Nipponbare and Kasalath varieties. It was found that the CYP72A3 gene of Kasalath contains an entire ORF from its start codon to stop codon and is presumed to be functional. In contrast, that of the Nipponbare variety was found to be a pseudogene in which the CYP72A31 gene has an about 3.2-kb deletion encompassing the first and second exons (FIG. 4). Note that CYP72A32 and CYP72A33 of both the Nipponbare and Kasalath varieties encode functional genes. The above results strongly suggested the possible involvement of the CYP72A31 gene in the BS resistance.

Example 3

Expression Analysis on CYP72A31, 72A32, and 72A33 Genes

First, unhulled seeds from Nipponbare (NB) and Kasalath (Kas) were sterilized. Next, the seeds were planted in an MSHF medium (Toki et al., Plant J., 47, 969 (2006)), and cultivated at 30 degree C. under constant lighting conditions. At Day 7, leaves and stems (seedling) and roots were sampled, rapidly froze in liquid nitrogen, and stored at −80 degree C. In addition, unhulled seeds from Nipponbare (NB) and Kasalath (Kas) were sterilized. Next, the seeds were planted in an N6D medium (Toki et al., Plant J., 47, 969 (2006)), and cultured at 33 degree C. under lighting conditions for 10 hours and at 30 degree C. under dark conditions for 14 hours. Calluses at the culture Day 7 or 21 (primary calluses at Day 7 and secondary calluses at Day 21) were sampled, rapidly froze in liquid nitrogen, and stored at −80 degree C. These calluses were used to perform expression analysis on CYP72A31, CYP72A32, and CYP72A33 genes.

Total RNA was extracted from each sample by using an RNeasy Plant mini kit (QIAGEN, Inc., Piscataway, N.J., USA). cDNA was amplified by using a reverse transcriptase ReverTra Ace (TOYOBO CO., LTD., Osaka, Japan). Twenty µL of a reaction mixture containing 1 µg of the total RNA, 2 µL of 10 pmol/µL Oligo(dT)20 primer (a kit component), 4 µL of 5×RT Buffer (a ReverTra Ace component), 1 µL of a dNTP mixture (10 mM each, a kit component), 1 µL of 10 U/µL RNase Inhibitor (a kit component), and 1 µL of the ReverTra Ace (a kit component) was prepared. Next, a reverse transcription reaction was carried out at 42 degree C. for 20 minutes. Then, the mixture was heated at 99 degree C. for 5 minutes to stop the reaction. Finally, the mixture was stored at 4 degree C.

A cDNA solution after the reaction was diluted 10 times, and used for a real-time PCR. For the real-time PCR, a reaction mixture was prepared using a Power SYBR Green PCR Master Mix (Life Technologies Corporation, Foster City, Calif., USA). Its transcription product was quantified using an ABI7300 Real-Tune PCR machine (Applied Biosystems, Inc.). Twenty μL of a reaction mixture containing 5 μL of the cDNA solution, 1 μL of each of 1 μM primers, and 10 μL of a Power SYBR Green PCR Master Mix was prepared. The mixture was heated at 95 degree C. for 10 minutes. Then, a reaction cycle consisting of 15 seconds at 95 degree C. and 1 minute at 60 degree C. was repeated 40 cycles. The level of the transcription product of each gene was compensated with an expression level of the OsActin1 gene. The CYP72A31 gene was amplified by using the following primers: a forward primer: 5'-GAAGAACAAAC-CTGACTACGAAGGCT-3' (SEQ ID NO: 3); and a reverse primer: 5'-CTCCATCTCTTTGTATGTTTTCCGACCAAT-3' (SEQ ID NO: 4). The CYP72A32 gene was amplified by using the following primers: a forward primer: 5'-AGGAC-TATTTGGGAAGAACAAACCTGAG-3' (SEQ ID NO: 5); and a reverse primer: 5'-TTCATCTCCTTGTATGTTCTC-CGCTTAAG-3' (SEQ II) NO: 6). The CYP72A33 gene was amplified by using the following primers: a forward primer: 5'-GGAAGAATAAACCAGACTATGATGGCC-3' (SEQ ID NO: 7); and a reverse primer: 5'-CTCCATCTCCTTGTAT-GTTTCGAGTAAG-3' (SEQ ID NO: 8). In addition, the OsActin1 gene was amplified by using the following primers: a forward primer: 5'-AGGCCAATCGTGAGAAGAT-GACCCA-3' (SEQ ID NO: 9); and a reverse primer: 5'-GT-GTGGCTGACACCATCACCAGAG-3' (SEQ ID NO: 10).

Figure 5B:
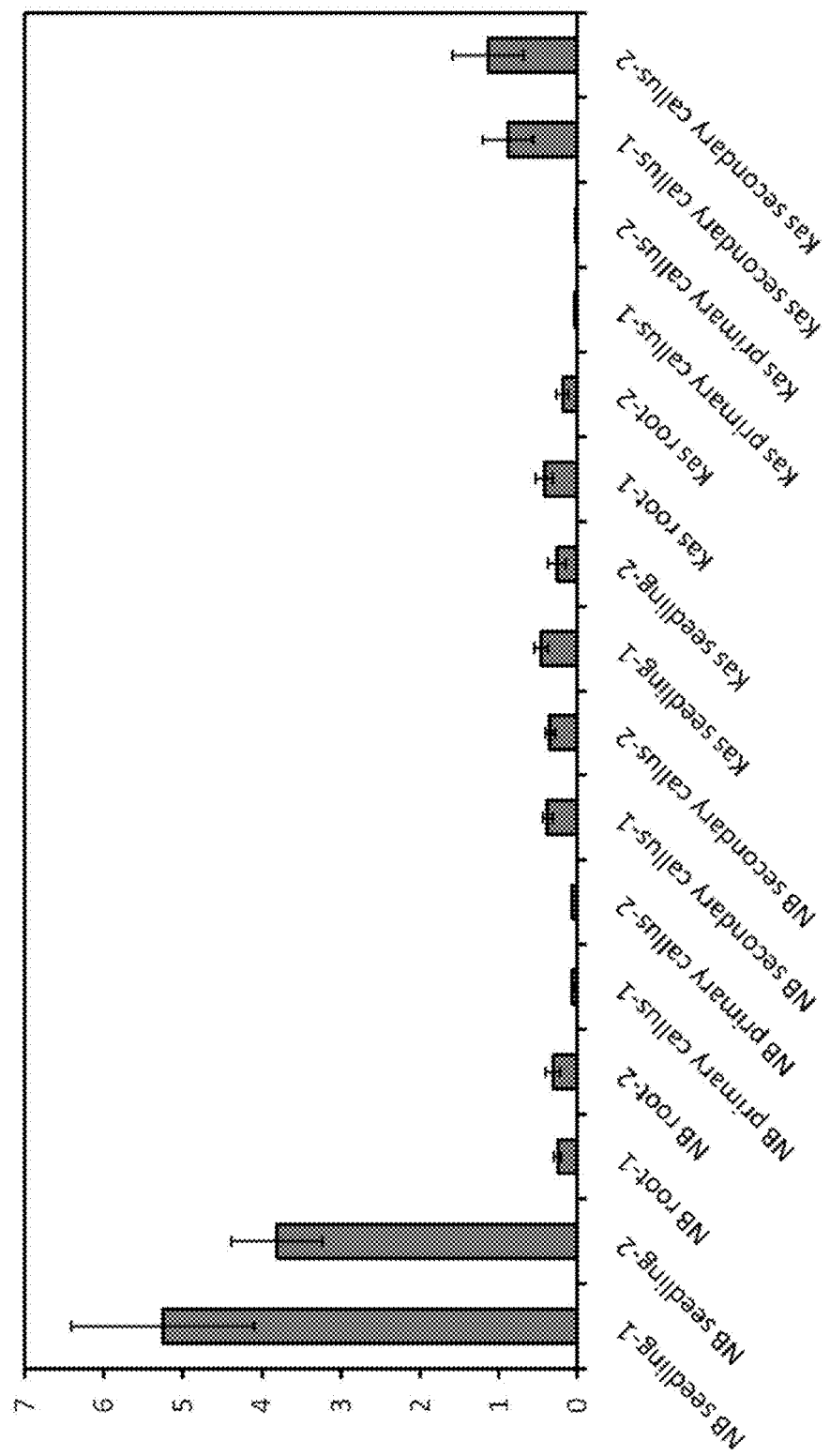
FIG. 5B is a graph illustrating the results of analyzing the expression of CYP72A32 gene in Nipponbare and Kasalath calluses.
Figure 5C:
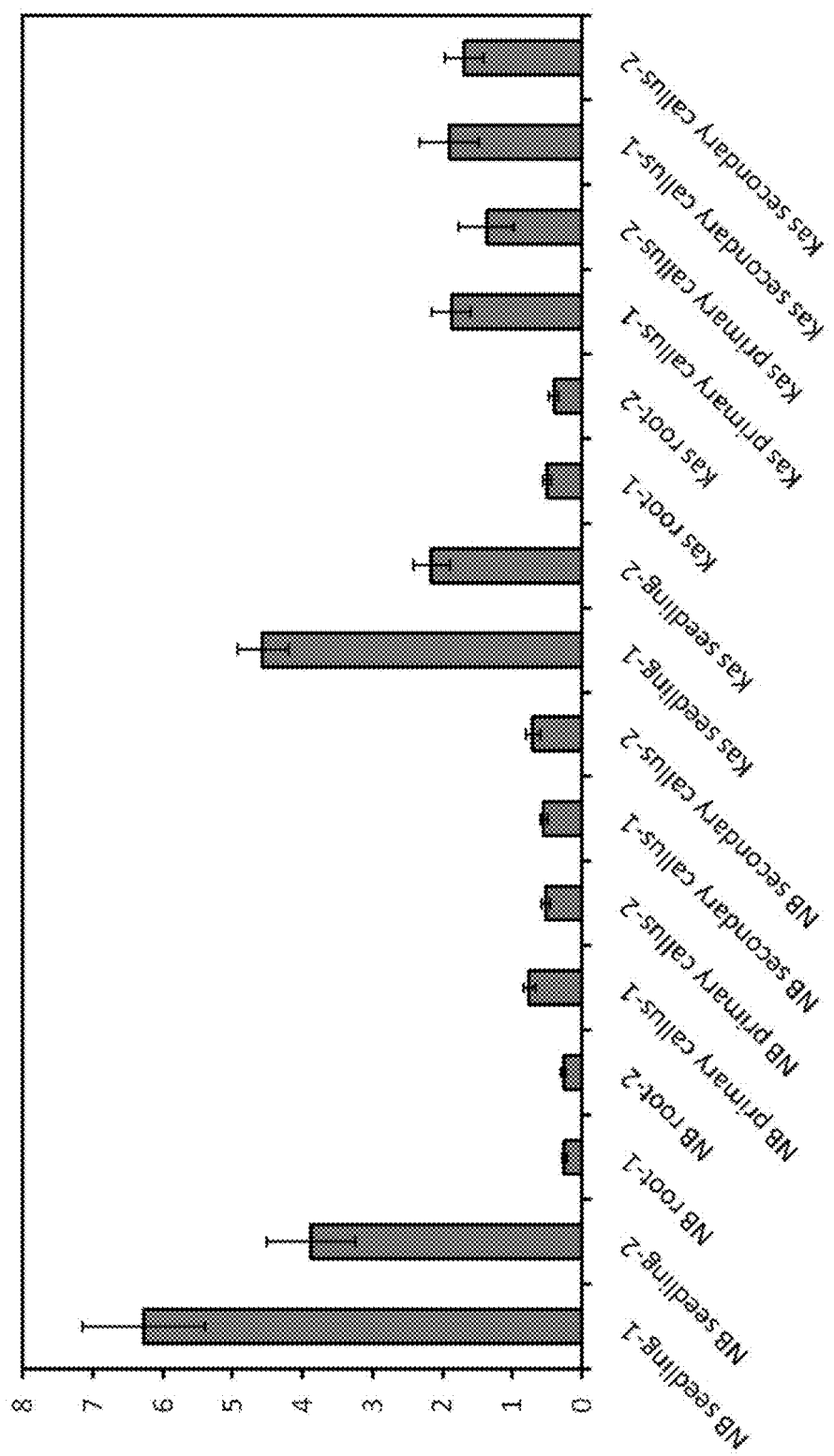
FIG. 5C is a graph illustrating the results of analyzing the expression of CYP72A33 gene in Nipponbare and Kasalath calluses.
Figure 8:
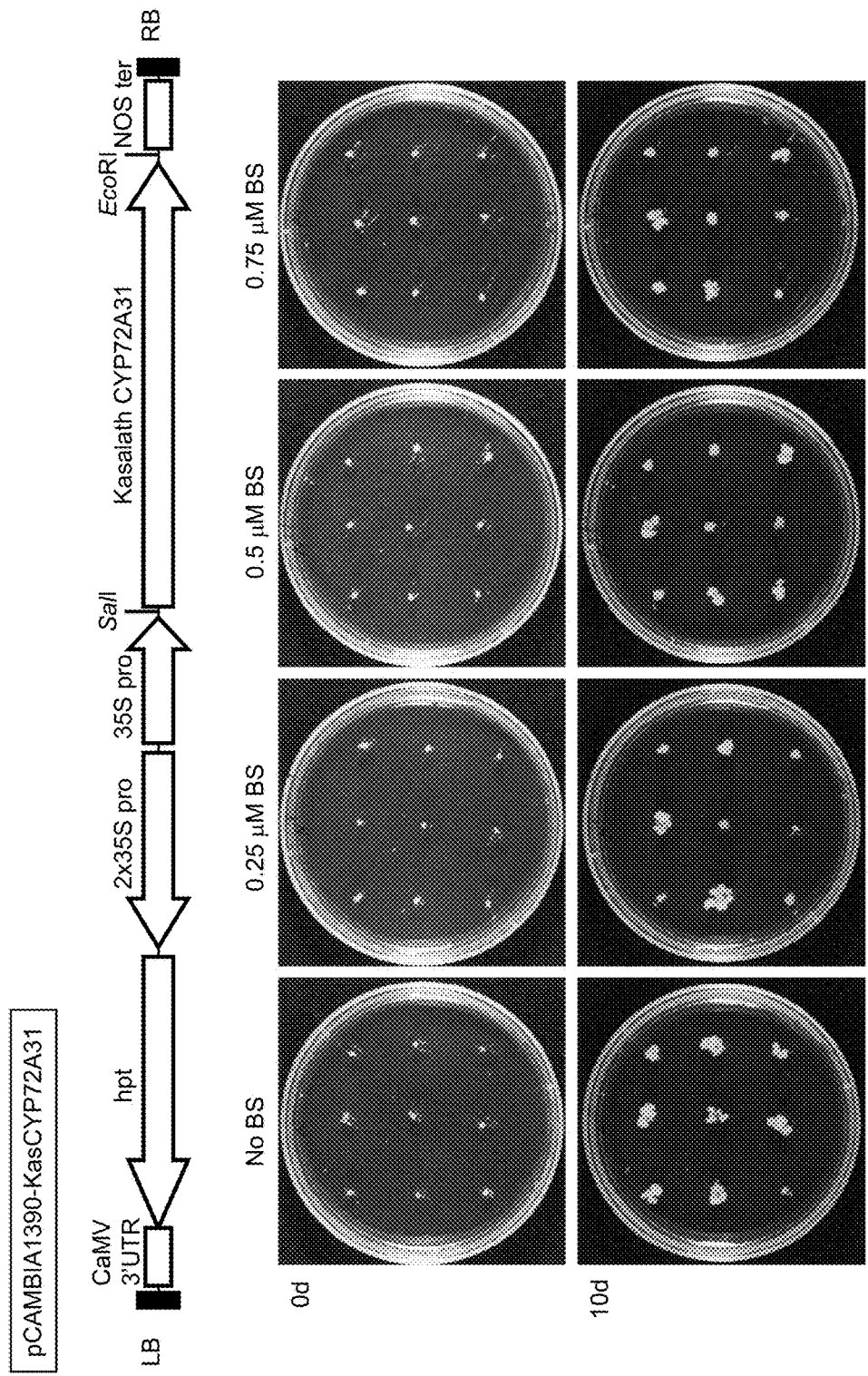
FIG. 8 includes photographs illustrating a growth inhibition by BS when a Kasalath-derived-CYP72A31 overexpression construct has been introduced into Nipponbare.

FIGS. 5A-5C illustrate the results. FIGS. 5A-5C demonstrate that in Nipponbare, the CYP72A31 gene is a pseudogene so that its gene expression was undetected. FIGS. 5A-5C also demonstrate that in Kasalath calluses, the CYP72A31 gene had a reduced expression level. This is consistent with a phenomenon that Kasalath calluses do not exhibit the BS resistance (see the below-described FIG. 8). Also, it was found that the CYP72A31 gene had a higher expression level in roots than in leaves and stems.

In contrast, there was an expression pattern that the CYP72A32 gene had an increased expression level in leaves and stems of Nipponbare. There appeared no substantial difference in an expression pattern of the CYP72A33 gene between Nipponbare and Kasalath.

Example 4

Figure 6:
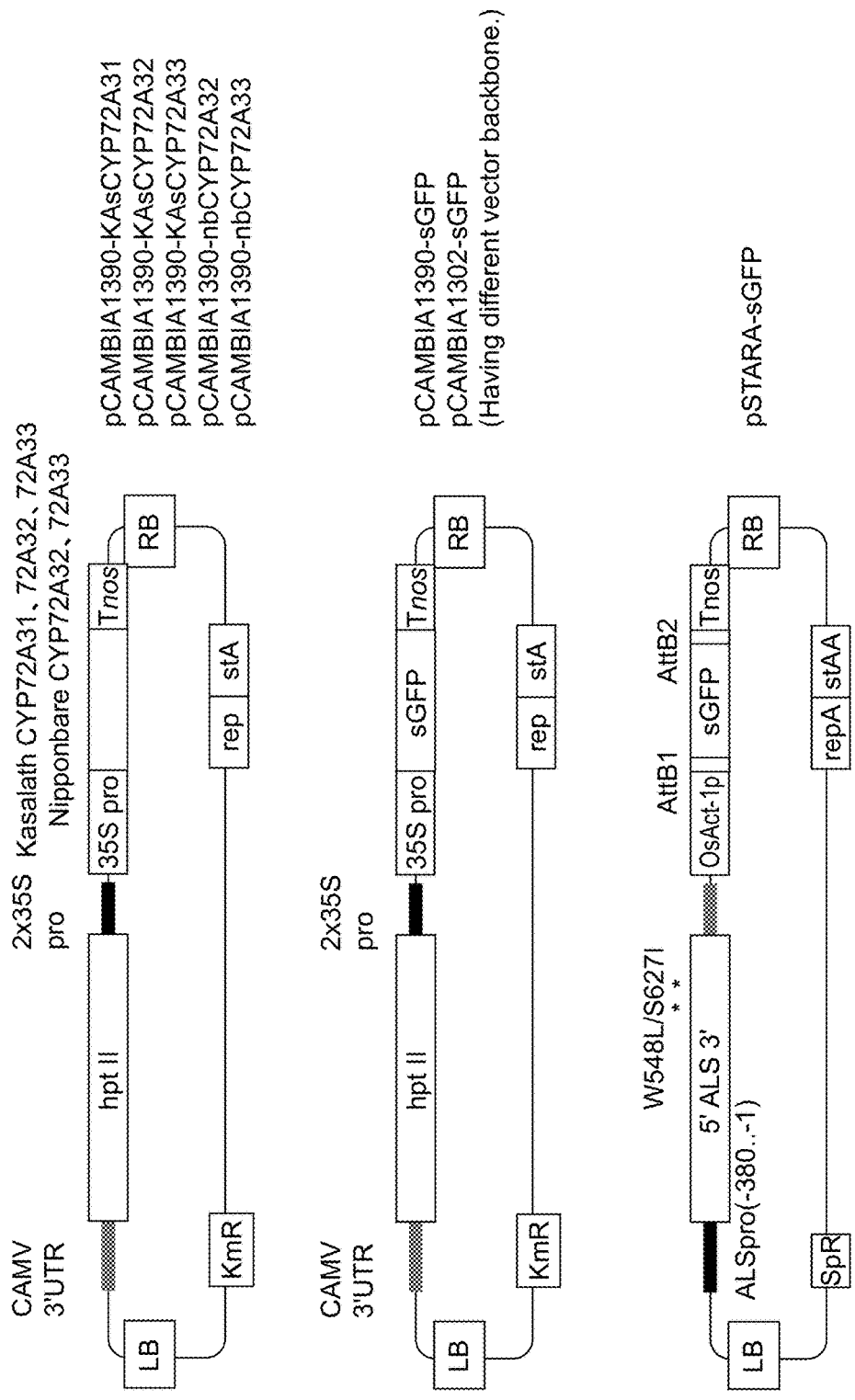
FIG. 6 outlines a configuration schematically illustrating 8 vector plasmids used for creating a transformed rice.

Introduction of HptII::35Spro::Kasalath CYP72A31::Tnos Vector Plasmid (pCAMBIA1390-KasCYP72A31), HptII::35Spro::Kasalath CYP72A32::Tnos Vector Plasmid (pCAMBIA1390-KasCYP72A32), HptII::35Spro::Kasalath CYP72A33::Tnos Vector Plasmid (pCAMBIA1390-KasCYP72A33), HptII::35Spro::Nipponbare CYP72A32::Tnos Vector Plasmid (pCAMBIA1390-nbCYP72A32), HptII::35 Spro::Nipponbare CYP72A33::Tnos Vector Plasmid (pCAMBIA1390-nbCYP72A33), HptII::35Spro::sGFP::Tnos Vector Plasmid (pCAMBIA1390-sGFP and pCAM-BIA1302-sGFP), or OsALS (W548L/S627I)::Os-Act-1pro::sGFP::Tnos Vector Plasmid (pSTARA-sGFP) into Agrobacterium tumefaciens EHA105 Strain Each of the above 8 vector plasmids (50 ng, FIG. 6) was added to 40 μl of Agrobacterium competent cells (an EHA105 strain) which were thawed on ice for electroporation, and gently mixed. The competent cell mixture was transferred to an ice-cold cuvette. Then, electroporation was performed with a Gene Pulser Xcell (Bio Rad Laboratories, Inc.) under conditions at 25 μF, 2.4 kV, and 200Ω. After that, 1 ml of a YM liquid medium (1 L of the medium contained 0.4 g of yeast extract (manufactured by Difco Laboratories, Inc.), 10 g of mannitol, 0.1 g of NaCl, 0.1 g of MgSO$_4$, and 0.5 g of K$_2$HPO$_4$-3H$_2$O; a pH was adjusted at 7.0) was added to the cuvette and mixed. Following that, all the amounts were transferred to a 1.5-ml Eppendorf tube, and the mixture was cultured while shaking at 27 degree C. and 250 rpm for 3 hours. After the culturing, about 50 μl of the culture was plated on a YM agar medium (containing 12.5 ppm rifampicin, 25 ppm chloramphenicol, and 50 ppm kanamycin (for vector plasmids except pSTARA-sGFP) or containing 12.5 ppm rifampicin, 25 ppm chloramphenicol, and 50 ppm spectinomycin), and further cultured at 27 degree C. for 2 to 3 days. Colonies were inoculated in a YM liquid medium (containing 12.5 ppm rifampicin, 25 ppm chloramphenicol, and 50 ppm kanamycin (for vector plasmids except pSTARA-sGFP) or containing 12.5 ppm rifampicin, 25 ppm chloramphenicol, and 50 ppm spectinomycin), and cultured while shaking at 27 degree C. for 2 to 3 days. Their glycerol stocks were prepared, and then stored at −85 degree C.

Example 5

Producing Transformed Rice

Rice seeds (Oryza sativa, cv. Nipponbare or Oryza sativa, cv. Kasalath) that were sterilized with sodium hypochlorite were used to transform Agrobacterium bacteria (Toki et al., Plant J., 47, 969 (2006)).

<Agrobacterium Preculture>

At 3 days before transformation, Agrobacterium bacteria (an Agrobacterium tumefaciens EHA105 strain) as prepared in Example 4 were plated on an AB solid medium (containing 12.5 ppm rifampicin, 25 ppm chloramphenicol, and 50 ppm kanamycin (for vector plasmids except pSTARA-sGFP) or containing 12.5 ppm rifampicin, 25 ppm chloramphenicol, and 50 ppm spectinomycin for vector plasmids), and cultured at 24 degree C. under dark conditions for 3 days.

<Infection and Coculture with Agrobacterium Bacteria>

First, 40 ml of an AAM medium was poured into a 50-ml Falcon tube, and acetosyringone was added at 40 mg/l. Precultured Agrobacterium bacteria were scraped using the tip of a 200-μl tip, dissolved into the above-described AAM medium, and shaken for 30 minutes under dark conditions. Shoot and endosperm portions were removed from a scutellum-derived callus that had been cultured in an N6D medium for 5 days. Then, the resulting callus was placed in an Agrobacterium bacteria-containing AAM medium, and shaken for 1.5 minutes. The AAM medium supernatant was poured into a beaker, and a residual AAM medium on the rice seed was wiped with a sterilized Kimtowel (product name; manufactured by NIPPON PAPER CRECIA Co., LTD.). The callus was placed in a 2N6-AS medium (containing 40 mg/l acetosyringone), and cocultured at 24 degree C. under dark conditions for 3 days.

<Removal of Agrobacterium Bacteria and Selection>

The cocultured callus was transferred to a 50 ml-Falcon tube, and washed 7 to 8 times with sterile water containing 500 mg/l carbenicillin to remove a residual washing solution as much as possible. When the water became clear after washing, the callus was placed in sterile water for 10 minutes. After washed 10 times with 500 ml of sterile water, the callus was placed on a sterilized piece of Kimwipe to remove the residual water. Then, the callus was transplanted onto an N6D medium (containing 50 ppm hygromycin (for vectors except pSTARA-sGFP vector) or 0.25 µM bispyribac sodium (for the pSTARA-sGFP vector), and 400 mg/l carbenicillin). After 2 weeks of culturing at 34 degree C. under lighting conditions, the callus was plated again and subjected to additional 2-week culturing.

<Redifferentiation of Transformants>

After selective culturing, the callus was transplanted onto a rice redifferentiation medium RE-III (containing 50 ppm hygromycin or 0.25 µM bispyribac sodium), cultured at 27 degree C. under 16L/8D conditions, and led to redifferentiate. The callus was plated after 2 weeks. At additional about 2 to 3 weeks, a redifferentiated, transformed rice ($T_0$) was obtained. Once a differentiated shoot and/or root had appeared, the rice was transplanted onto a hormone-free (HF) medium (containing 50 ppm hygromycin or 0.25 µM bispyribac sodium). Table 1 shows each medium component.

TABLE 1

The amount of each component is designated as mg/L. The amount of a component denoted by the symbol * is designated as g/L.

|  | N6D | 2N6-AS | AAM |
|---|---|---|---|
| INORGANIC SALTS | | | |
| Macroelement | | | |
| $KNO_3$ | 2830 | 2830 | |
| $NH_4Cl$ | | | |
| $NH_4NO_3$ | | | |
| $(NH_4)_2SO_4$ | 463 | 463 | |
| $MgSO_4 \cdot 7H_2O$ | 185 | 185 | 250 |
| $CaCl_2 \cdot 2H_2O$ | 166 | 166 | 150 |
| $NaH_2PO_4 \cdot 2H_2O$ | | | 150 |
| $K_2HPO_4$ | | | |
| $KH_2PO_4$ | 400 | 400 | |
| KCl | | | 3000 |
| Microelement | | | |
| EDTA•2Na | 37.3 | 37.3 | |
| $FeSO_4 \cdot 7H_2O$ | 27.8 | 27.8 | |
| Fe-EDTA | | | 40 |
| $MnSO_4 \cdot 4-6H_2O$ | 4.4 | 4.4 | 10 |
| $ZnSO_4 \cdot 7H_2O$ | 1.5 | 1.5 | 2 |
| $CuSO_4 \cdot 5H_2O$ | | | 0.025 |
| $CoCl_2 \cdot 6H_2O$ | | | 0.025 |
| KI | 0.8 | 0.8 | 0.75 |
| $H_3BO_3$ | 1.6 | 1.6 | 3 |
| $Na_2MoO_4 \cdot 2H_2O$ | | | 0.25 |
| VITAMINS | | | |
| Myo-inositol | 100 | 100 | 100 |
| Nicotinic acid | 0.5 | 0.5 | 1 |
| Pyridoxine HCl | 0.5 | 0.5 | 1 |
| Thiamine HCl | | | 10 |
| PHYTOHORMONES | | | |
| 2,4-D | 2 | 2 | |
| Acetosyringone | | 20 | |
| NAA | | | |
| Kinetin | | | |
| AMINO ACIDS | | | |
| Casamino acids | 300 | 300 | 500 |
| Glycine | 2 | 2 | 7.5 |
| L-Arginine | | | 176.7 |
| L-Proline | 2878 | | |
| L-Glutamine | | | 900 |
| L-Aspartic acid | | | 300 |
| CARBON SOURCE | | | |
| Sucrose (g/L)* | 30 | 30 | 68.5 |
| Sorbitol (g/L)* | | | |
| Glucose (g/L)* | | 10 | 36 |
| GELLING AGENTS | | | |
| Gelrite (g/L)* | 4 | 4 | |
| Bacto agar (g/L)* | | | |
| pH | 5.8 | 5.2 | 5.2 |

TABLE 1-continued

The amount of each component is designated as mg/L. The amount of a component denoted by the symbol * is designated as g/L.

|  | RE-III | HF | AB |
|---|---|---|---|
| INORGANIC SALTS | | | |
| Macroelement | | | |
| $KNO_3$ | 1900 | 1900 | |
| $NH_4Cl$ | | | 1000 |
| $NH_4NO_3$ | 1650 | 1650 | |
| $(NH_4)_2SO_4$ | | | |
| $MgSO_4 \cdot 7H_2O$ | 370 | 370 | 296 |
| $CaCl_2 \cdot 2H_2O$ | 440 | 440 | 10 |
| $NaH_2PO_4 \cdot 2H_2O$ | | | 1300 |
| $K_2HPO_4$ | | | 3000 |
| $KH_2PO_4$ | 170 | 170 | |
| KCl | | | 150 |
| Microelement | | | |
| EDTA•2Na | 37.3 | 37.3 | |
| $FeSO_4 \cdot 7H_2O$ | 27.8 | 27.8 | 2.5 |
| Fe-EDTA | | | |
| $MnSO_4 \cdot 4-6H_2O$ | 22.3 | 22.3 | |
| $ZnSO_4 \cdot 7H_2O$ | 8.6 | 8.6 | |
| $CuSO_4 \cdot 5H_2O$ | 0.025 | 0.025 | |
| $CoCl_2 \cdot 6H_2O$ | 0.025 | 0.025 | |
| KI | 0.83 | 0.83 | |
| $H_3BO_3$ | 6.2 | 6.2 | |
| $Na_2MoO_4 \cdot 2H_2O$ | 0.25 | 0.25 | |
| VITAMINS | | | |
| Myo-inositol | 100 | 100 | |
| Nicotinic acid | 0.5 | 0.5 | |
| Pyridosine HCl | 0.5 | 0.5 | |
| Thiamine HCl | 0.1 | 0.1 | |
| PHYTOHORMONES | | | |
| 2,4-D | | | |
| Acetosyringone | | | |
| NAA | 0.02 | | |
| Kinetin | 2 | | |
| AMINO ACIDS | | | |
| Casamino acids | 2000 | | |
| Glycine | 2 | 2 | |
| L-Arginine | | | |
| L-Proline | | | |
| L-Glutamine | | | |
| L-Aspartic acid | | | |
| CARBON SOURCE | | | |
| Sucrose (g/L)* | 30 | 30 | |
| Sorbitol (g/L)* | 30 | | |
| Glucose (g/L)* | | | 5 |
| GELLING AGENTS | | | |
| Gelrite (g/L)* | 4 | 4 | |
| Bacto agar (g/L)* | | | 15 |
| pH | 5.8 | 5.8 | 7.2 |

<Cultivation of Transformants and T1 Seed Sampling>

A plant which had enough rooting in a hormone-free (HF) medium was transplanted into a vinyl pot with a diameter of 8 cm. After the plant was grown in a containment green house (at 25 to 30 degree C. under 16L/8D conditions), T1 seeds were harvested.

Example 6

Callus Growth Test on BS-Containing Medium by Using Rice Callus (Nipponbare. Kasalath) Transformed with HptII::35Spro::Kasalath CYP72A31::Tnos Vector Plasmid (pCAMBIA1390-KasCYP72A31) or HptII::35Spro::sGFP::Tnos Vector Plasmid (pCAMBIA1390-sGFP)

According to Example 5, an HptII::35Spro::Kasalath CYP72A31::Tnos vector plasmid (pCAMBIA1390-KasCYP72A31, a kasCYP72A31 overexpression construct) or, as a control, an HptII::35Spro::sGFP::Tnos vector plasmid (pCAMBIA1390-sGFP, an sGFP overexpression construct) was introduced into a rice variety (cultivars: Nipponbare and Kasalath) by using an *Agrobacterium* method. Transformed calluses selected with 50 ppm hygromycin were isolated, and transplanted onto a bispyribac-sodium (BS)-containing medium to examine callus growth.

Figure 7:
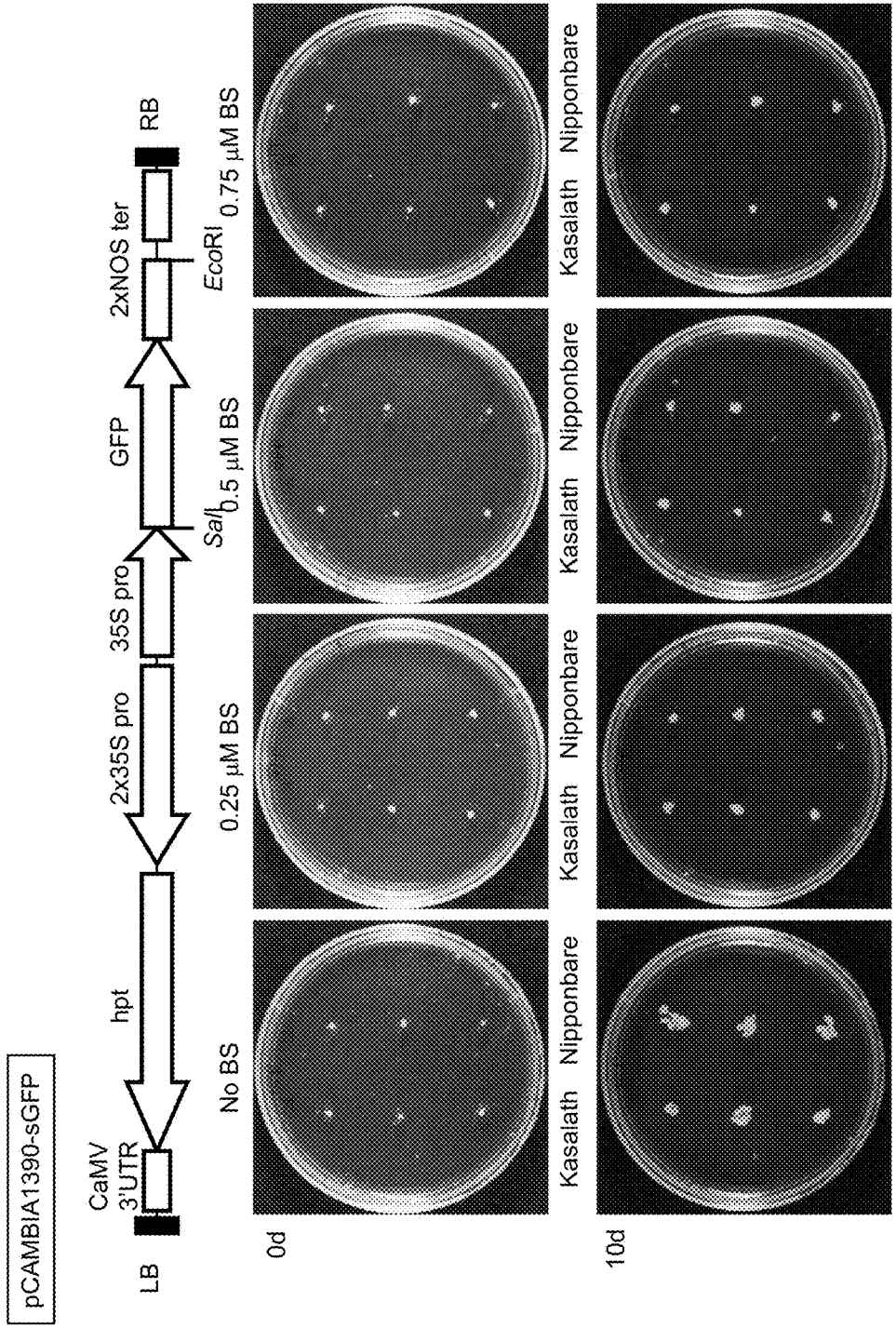
FIG. 7 includes photographs illustrating a growth inhibition by BS when a GFP overexpression construct has been introduced into Nipponbare and Kasalath.
Figure 9:
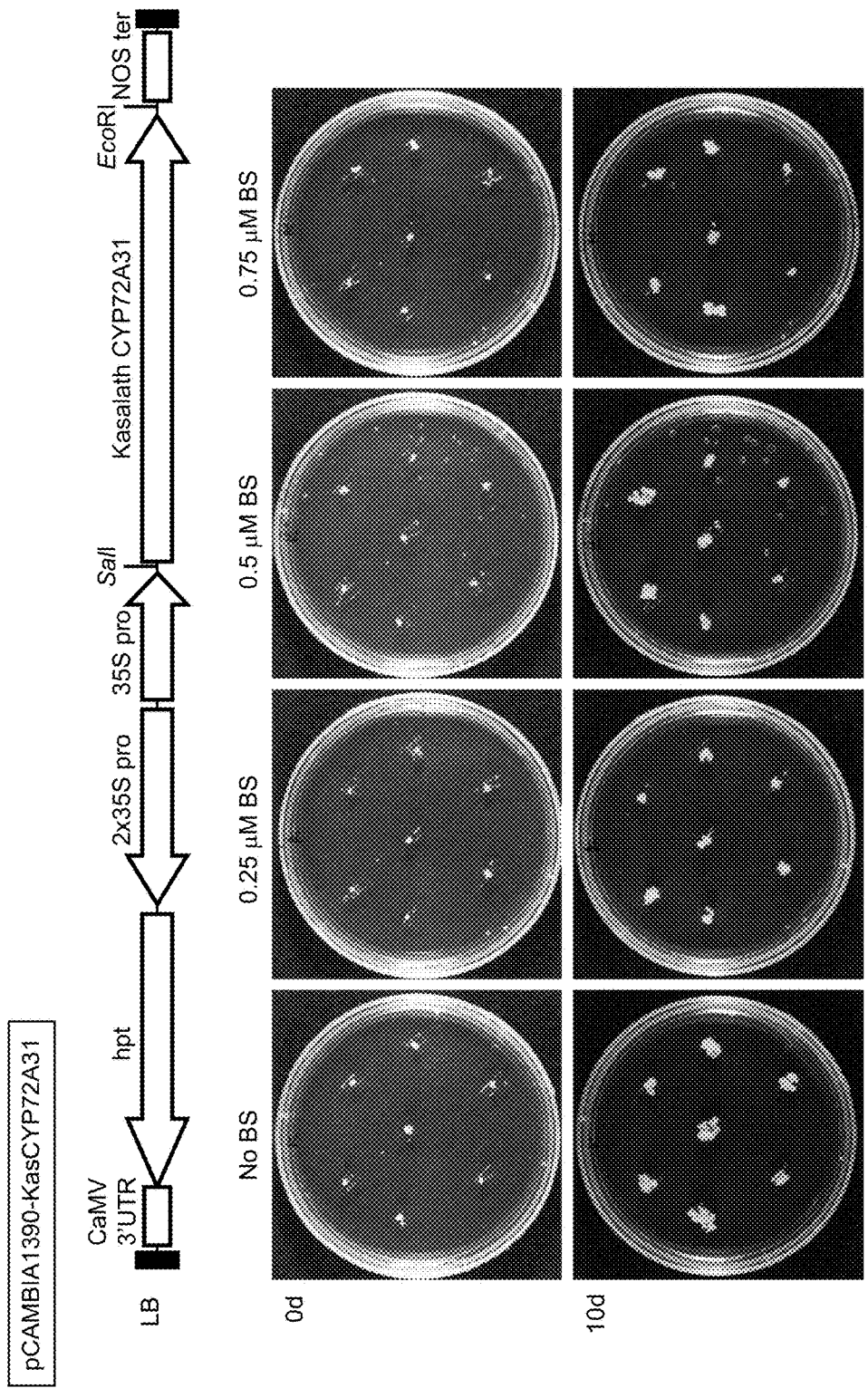
FIG. 9 includes photographs illustrating a growth inhibition by BS when a Kasalath-derived-CYP72A31 overexpression construct has been introduced into Kasalath.

A GFP overexpression construct was introduced into Nipponbare and Kasalath calluses. At that time, any of the varieties were planted on a medium containing 0.25, 0.5, or 0.75 μM BS, which inhibited their growth (FIG. 7). In contrast, a CYP72A31 overexpression construct was introduced into Nipponbare and Kasalath calluses, and the calluses were likewise planted on a medium containing 0.25, 0.5, or 0.75 μM BS. At that time, the calluses of both Nipponbare and Kasalath, like calluses planted on a BS-free medium, were demonstrated to grow (FIG. 8: Nipponbare: FIG. 9: Kasalath). In addition, FIG. 7 indicated that non-recombinant Kasalath calluses did not exhibit BS resistance. This is because the Kasalath calluses had a reduced expression level of the CYP72A31 gene (see FIG. 5A).

Example 7

Callus Growth Test on BS-Containing Medium by Using Rice Callus (Nipponbare, Kasalath) Transformed with HptII::35Spro::Kasalath CYP72A32:: Tnos Vector Plasmid (pCAMBIA1390-KasCYP72A32), HptII::35Spro::Kasalath CYP72A33::Tnos Vector Plasmid (pCAMBIA1390-KasCYP72A33), HptII::35Spro::Nipponbare CYP72A32::Tnos Vector Plasmid (pCAMBIA1390-nbCYP72A32), or HptII::35Spro::Nipponbare CYP72A33::Tnos Vector Plasmid (pCAMBIA1390-nbCYP72A33)

According to Example 5, an HptII::35Spro::Kasalath CYP72A32::Tnos vector plasmid (pCAMBIA1390-KasCYP72A32, a kasCYP72A32 overexpression construct), an HptII::35 Spro::Kasalath CYP72A33::Tnos vector plasmid (pCAMBIA1390-KasCYP72A33, a kasCYP72A33 overexpression construct), an HptII::35Spro::Nipponbare CYP72A32::Tnos vector plasmid (pCAMBIA1390-nbCYP72A32, an nbCYP72A32 overexpression construct), or an HptII::35Spro::Nipponbare CYP72A33::Tnos vector plasmid (pCAMBIA1390-nbCYP72A33, an nbCYP72A33 overexpression construct) was introduced into a rice variety (a cultivar: Nipponbare) by using an *Agrobacterium* method. Transformed calluses selected with 50 ppm hygromycin were isolated, and transplanted onto a bispyribac-sodium (BS)-containing medium to examine callus growth.

Figure 10:
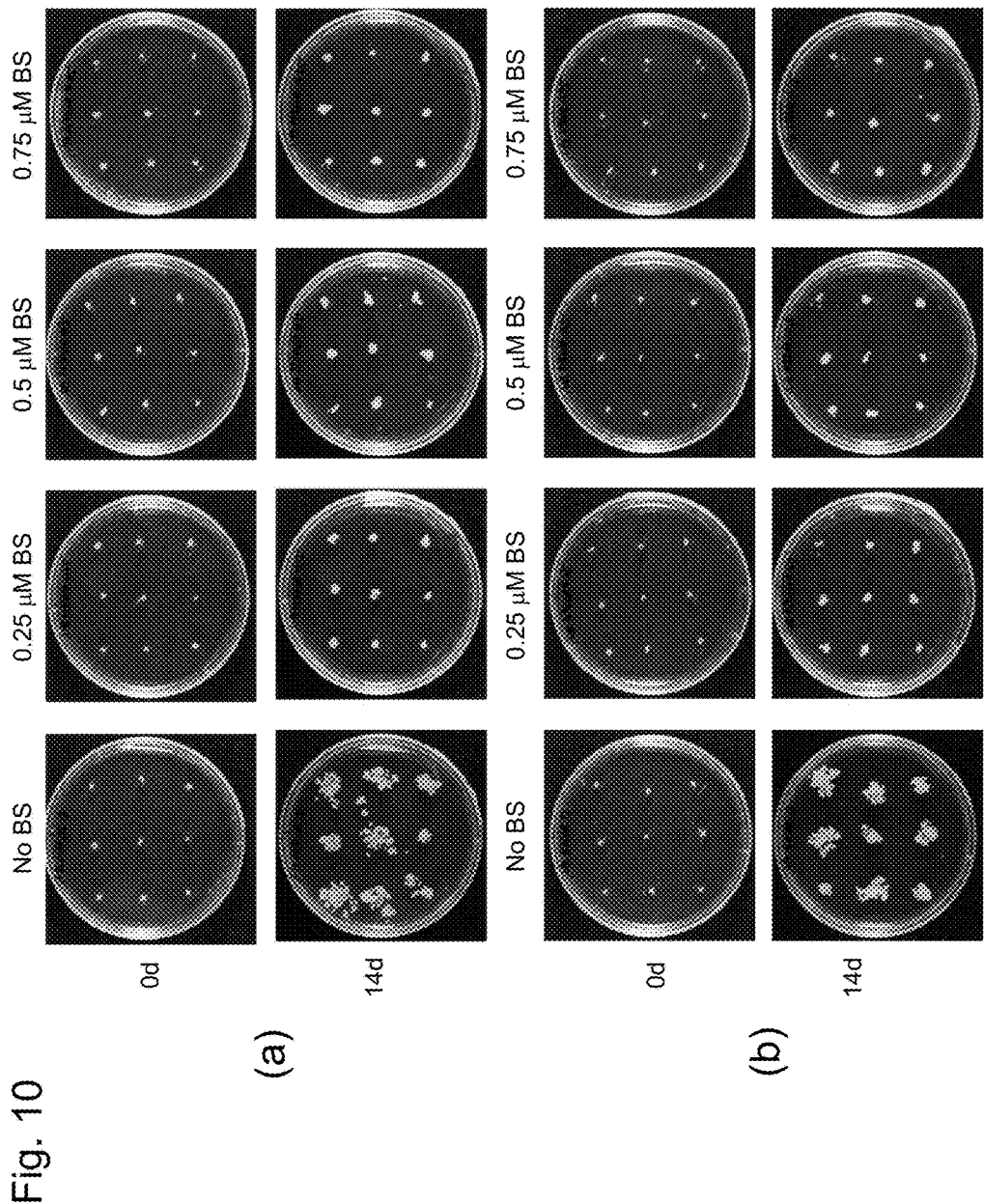
FIG. 10(a) is photographs showing the results of overexpression of Nipponbare-derived CYP72A32.
FIG. 10(b) is photographs showing the results of overexpression of Kasalath-derived CYP72A32.
Figure 11:
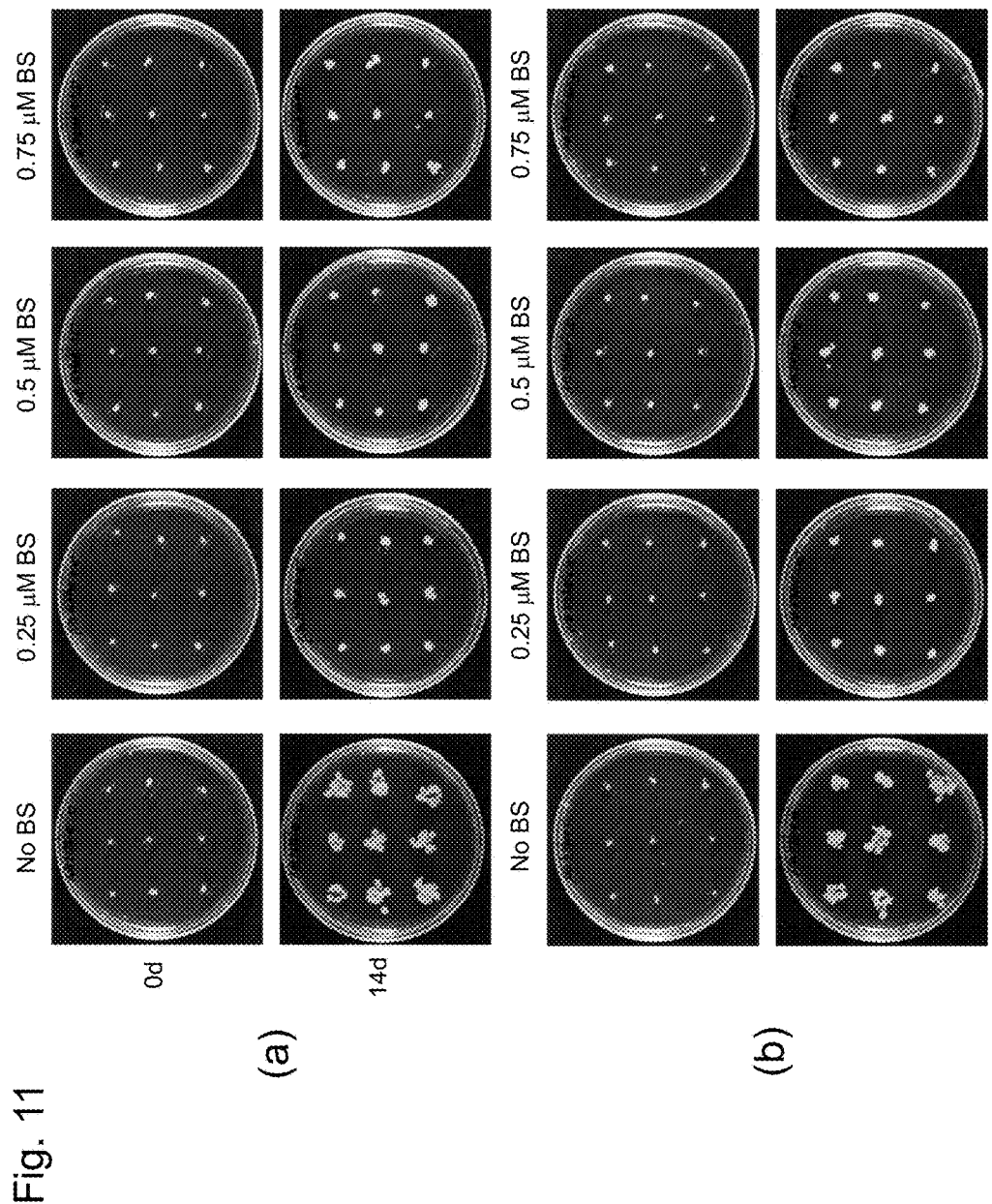
FIG. 11(a) is photographs showing the results of overexpression of Nipponbare-derived CYP72A33.
FIG. 11(b) is photographs showing the results of overexpression of Kasalath-derived CYP72A33.

FIGS. 10(*a*) and (*b*) show the results as obtained by overexpressing the Nipponbare-derived CYP72A32 and the results as obtained by overexpressing the Kasalath-derived CYP72A32, respectively. In addition, FIGS. 11(A) and (*b*) show the results as obtained by overexpressing the Nipponbare-derived CYP72A33 and the results as obtained by overexpressing the Kasalath-derived CYP72A33, respectively. FIGS. 10 and 11 demonstrated that when any of the Kasalath-derived and Nipponbare-derived CYP72A32 and CYP72A33 was overexpressed, Nipponbare calluses were not grown on the BS-containing medium.

Example 8

Figure 12:
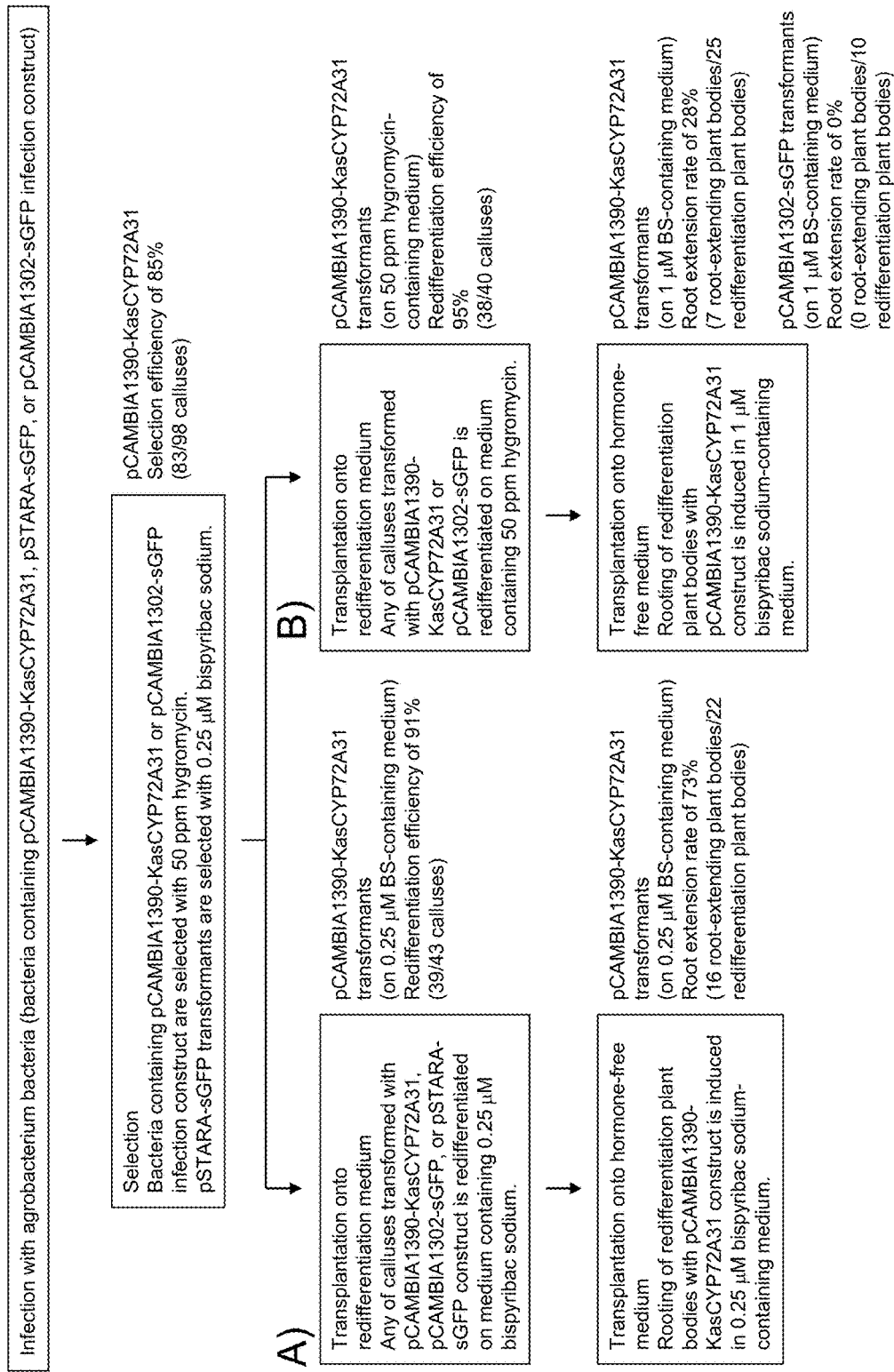
FIG. 12 is a flow chart illustrating a method for transformation as performed in Examples 8 and 9.
Figure 13:
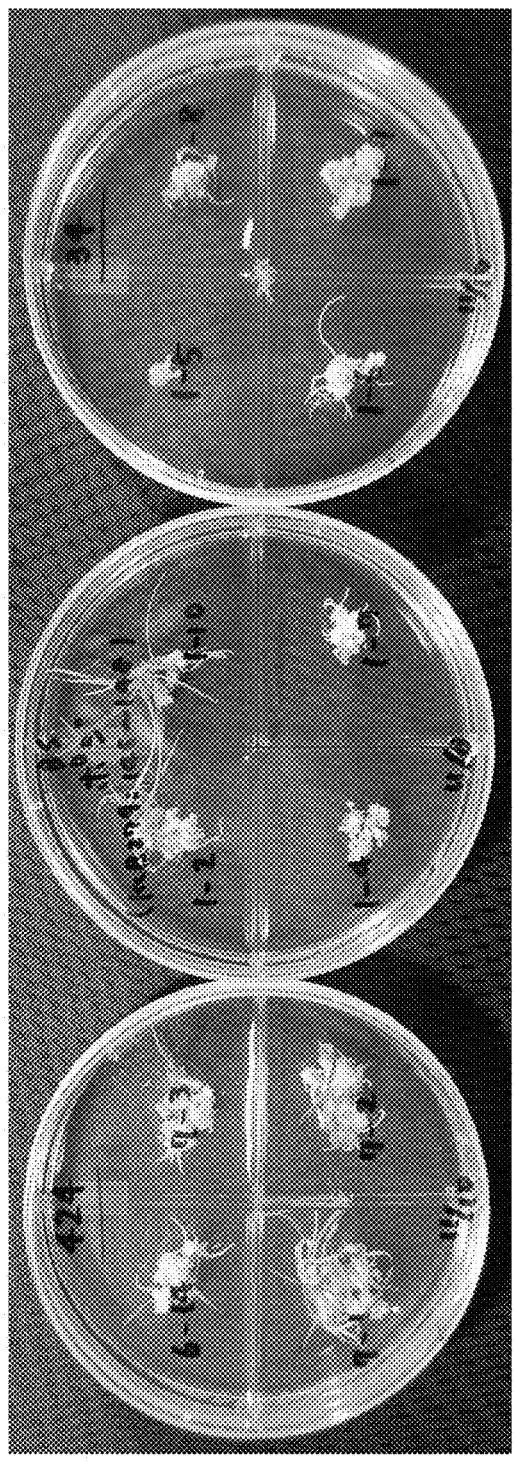
FIG. 13 is a photograph taken at the time when transformed rice variants have been grown in a BS-containing redifferentiation medium.
Figure 14:
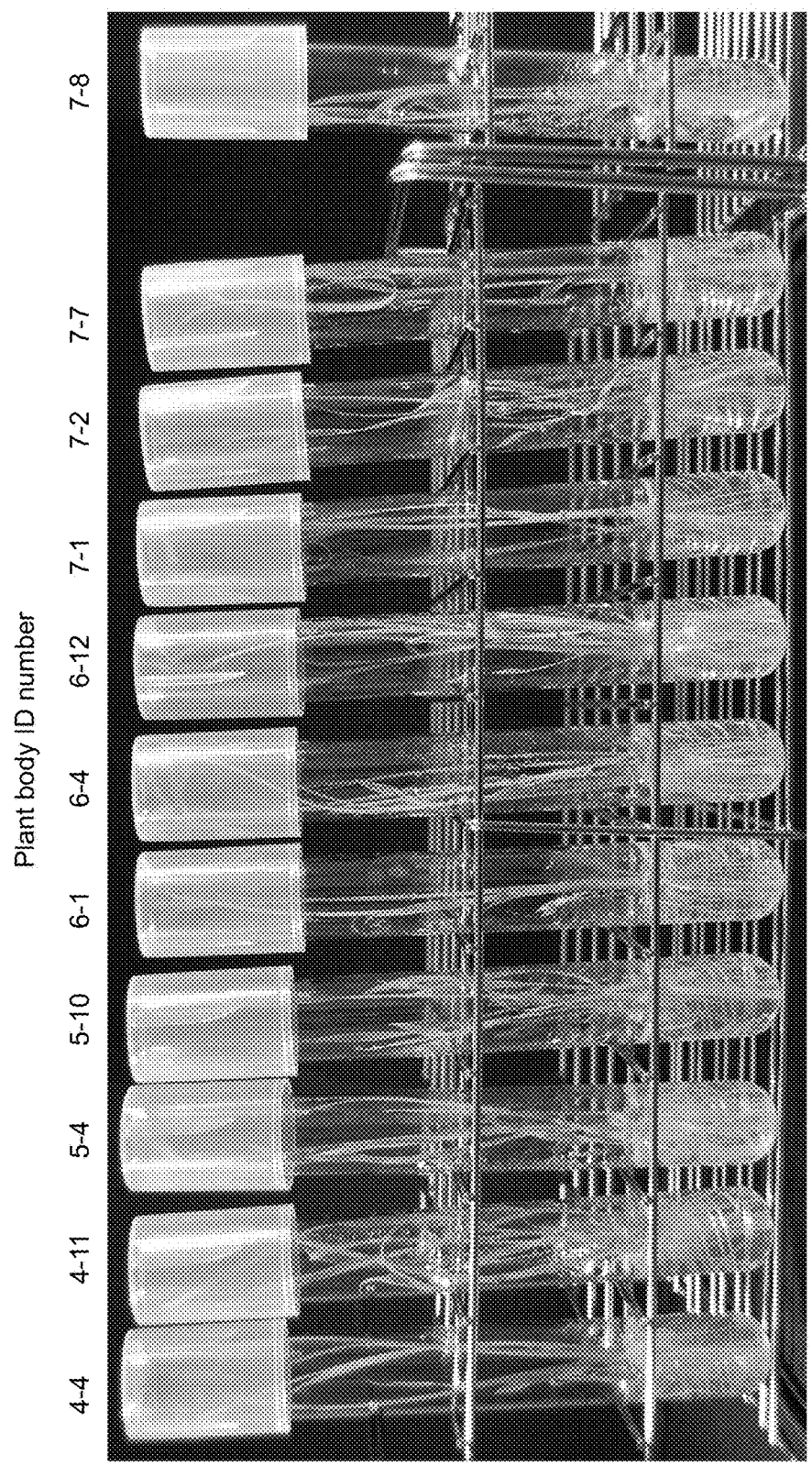
FIG. 14 is a photograph taken at the time when the redifferentiation plant bodies shown in FIG. 13 have been grown in a BS-containing hormone-free medium.

Test for Redifferentiation on BS-Containing Redifferentiation Medium by Using Rice Callus Transformed with Kasalath-Derived CYP72A31 Gene According to Example 5, an HptII::35Spro::Kasalath CYP72A31::Tnos vector plasmid (pCAMBIA1390-KasCYP72A31, a kasCYP72A31 overexpression construct) or, as controls, an HptII::35Spro::sGFP::Tnos vector plasmid (pCAMBIA1302-sGFP, an sGFP overexpression construct) or an OsALS (W548L/S627I)::OsAct-1pro::sGFP:: Tnos vector plasmid (pSTARA-sGFP, a BS-resistant construct) was introduced into a rice variety (a cultivar: Nipponbare) by using an *Agrobacterium* method. According to a schedule designated in FIG. 12A), transformed calluses were selected with 50 ppm hygromycin. The pCAMBIA1390-KasCYP72A31 construct had a transformation efficiency of 85% (83/98 calluses). Of all the calluses, 43 calluses were transplanted onto a redifferentiation medium containing 0.25 μM BS. As a result, shoots and roots were differentiated from the callus at a redifferentiation efficiency of 91% (39/43 calluses (FIG. 13). Following that, the calluses were transplanted onto a hormone-free medium containing 0.25 μM BS. As a result, the calluses with extending roots accounted for 73% (16/22 redifferentiation calluses) of all the redifferentiation calluses (FIG. 14). In contrast, calluses transformed with pCAMBIA1302-sGFP without a BS-resistant marker were found not to include those redifferentiated on a redifferentiation medium containing 0.25 μM BS. In a callus KLB-279 (transformed with pSTARA vector), shoots and roots were differentiated from the callus, so that a redifferentiated callus was successfully observed (FIG. 13).

Example 9

Figure 15:
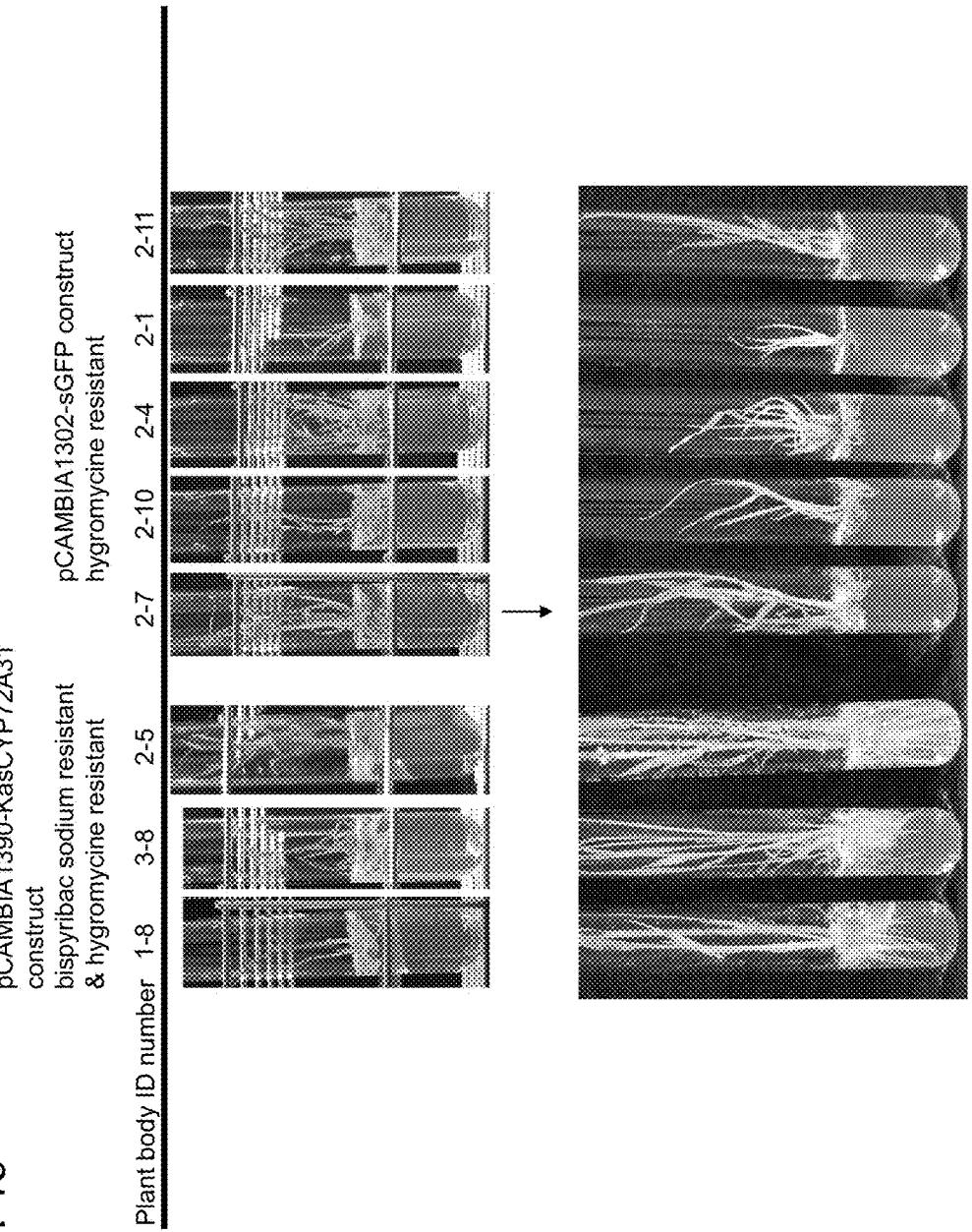
FIG. 15 is photographs illustrating the results of observing root growth of the redifferentiation plant bodies as produced in Example 9 while culturing them in a BS-containing hormone-free medium.

Test for Rooting in BS-Containing Hormone-Free Medium by Using Rice Redifferentiation Plant Body Transformed with Kasalath-Derived CYP72A31 Gene Rice (Nipponbare) calluses transformed with a pCAMBIA1390-KasCYP72A31 construct in Example 8 were obtained by 50 ppm hygromycin selection. When these calluses were transplanted onto a redifferentiation medium containing 50 ppm hygromycin, shoots and roots were differentiated from the callus at a redifferentiation efficiency of 95% (38/40 calluses). Subsequently, 25 redifferentiation calluses transformed with a pCAMBIA1390-KasCYP72A31 construct were transplanted onto a hormone-free medium containing 1 μM BS. As a result, 7 calluses had extending roots (a root extension rate of 28%. FIG. 15). In contrast, redifferentiation calluses transformed with a pCAMBIA1302-sGFP construct as a control had no rooting observed in a hormone-free medium containing 1 µM BS, which killed the plant bodies.

According to Examples 8 and 9, the Kasalath CYP72A31 gene was used to successfully select redifferentiated plant bodies in a redifferentiation medium containing 0.25 µM BS in a manner similar to those with a rice ALS gene having two mutations (W548L/S627I). The plant bodies were found to have extending roots in a hormone-free medium containing 0.25 or 1 µM BS. Furthermore, it was found that use of a hormone-free medium containing 1 µM BS was able to prevent the escape of an introduced gene.

Example 10

Production of Transformed *Arabidopsis thaliana*

Figure 16A:
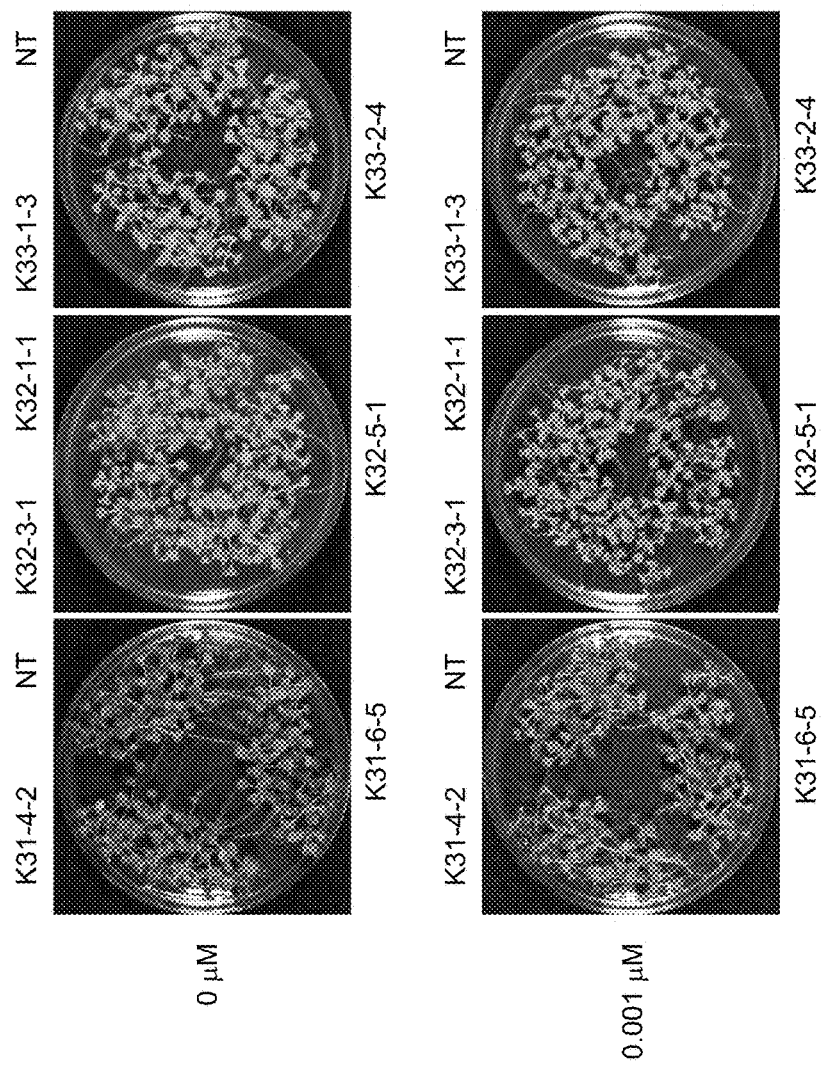
FIG. 16A is a photograph showing the results of a growth test in a BS-containing medium on *Arabidopsis thaliana* (Col-0) transformed with a Kasalath-derived CYP72A31 gene, a Kasalath-derived CYP72A32 gene, or a Kasalath-derived CYP72A33 gene.
Figure 16B:
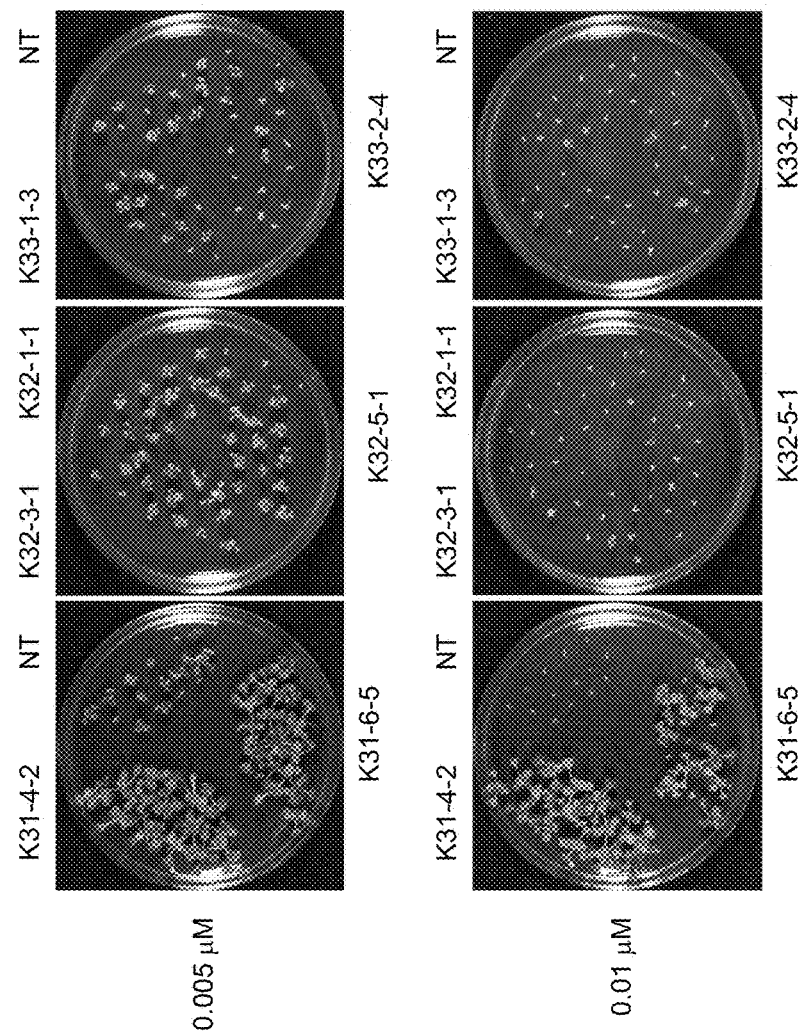
FIG. 16B is a photograph showing the results of a growth test in a BS-containing medium on *Arabidopsis thaliana* (Col-0) transformed with a Kasalath-derived CYP72A31 gene, a Kasalath-derived CYP72A32 gene, or a Kasalath-derived CYP72A33 gene.

In this Example, *Agrobacterium* as prepared in Example 4 was used to introduce HptII::35Spro::Kasalath CYP72A31::Tnos vector plasmid (pCAMBIA1390-KasCYP72A31), HptII::35Spro::Kasalath CYP72A32::Tnos vector plasmid (pCAMBIA1390-KasCYP72A32), or HptII::35Spro::Kasalath CYP72A33::Tnos vector plasmid (pCAMBIA1390-KasCYP72A33) into *Arabidopsis thaliana* (ecotype: Col-0) by using a floral-dip method. The floral-dip method followed a standard method. The resulting T2 seeds were cultivated on a medium containing 20 ppm hygromycin, and examined for the proportion of plant bodies that exhibited sensitivity to hygromycin. Varieties whose seeded plant bodies all exhibited hygromycin resistance were regarded as fixed lines that seemed homozygous for the T-DNA insertion. K31-4-2 and K31-6-5 were selected as fixed lines derived from pCAMBIA1390-KasCYP72A31; K32-1-1, K32-3-1, and K32-5-1 were selected as fixed lines derived from pCAMBIA1390-KasCYP72A32; and K33-1-3 and K33-2-4 were selected as fixed lines derived from pCAMBIA1390-KasCYP72A33. Their seeds were seeded in a medium containing each concentration of BS, and cultivated for 10 days. FIGS. 16A and 16B illustrate the results.

FIGS. 16A and 16B demonstrated that the transformed *Arabidopsis thaliana* varieties with overexpressed Kasalath-derived CYP72A31 were grown under BS-untreated conditions as well as even under high-concentration BS conditions in which non-transformed *Arabidopsis thaliana* (NT) was abnormally grown. In contrast, the transformed *Arabidopsis thaliana* varieties with overexpressed Kasalath-derived CYP72A32 or CYP72A33 did not show such reduced BS sensitivity.

Figure 17A:
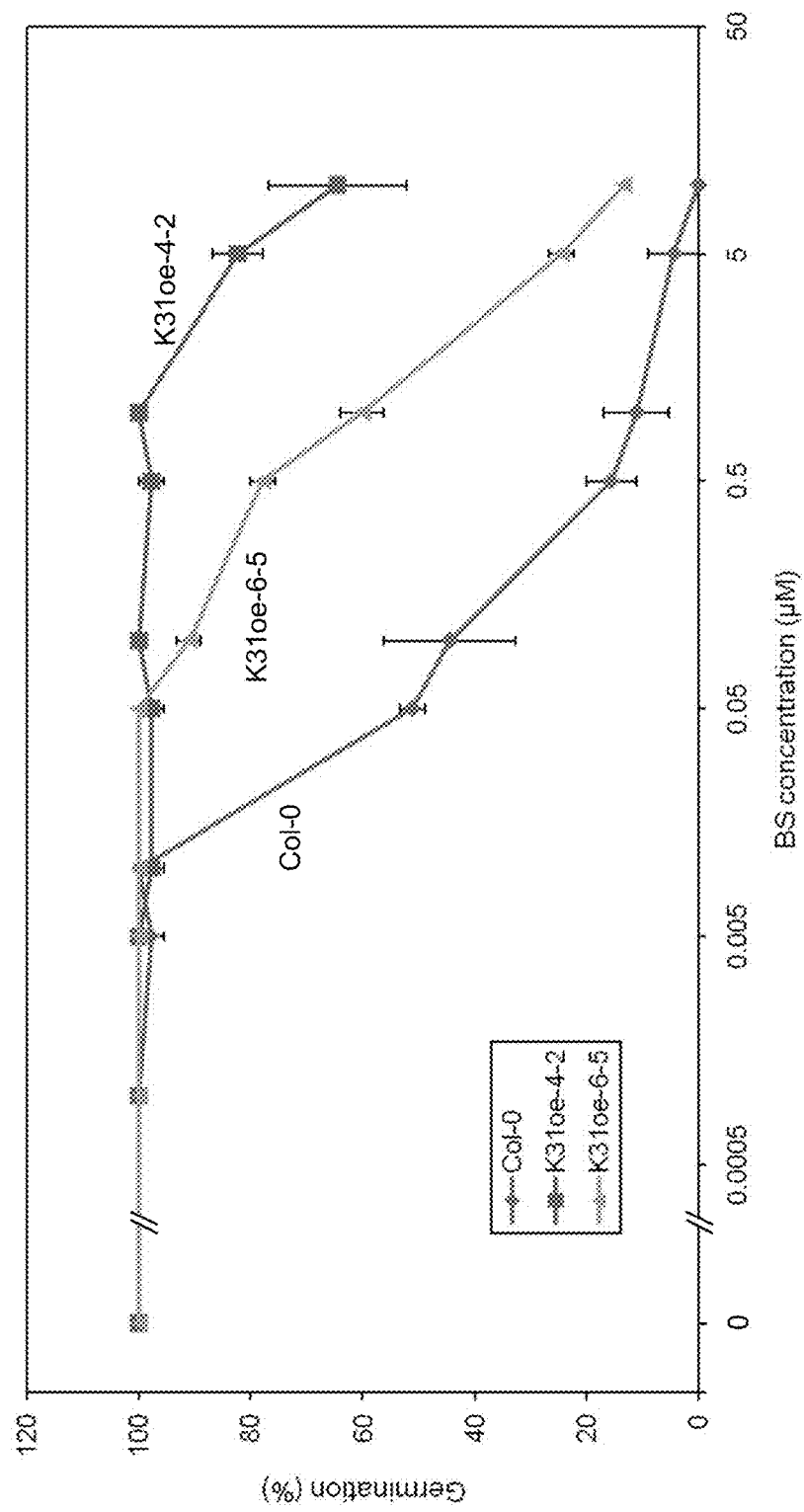
FIG. 17A is a diagram showing the results of a growth test (proportions of germinated seeds) in a BS-containing medium on *Arabidopsis thaliana* (Col-0) transformed with a Kasalath-derived CYP72A31 gene.
Figure 17B:
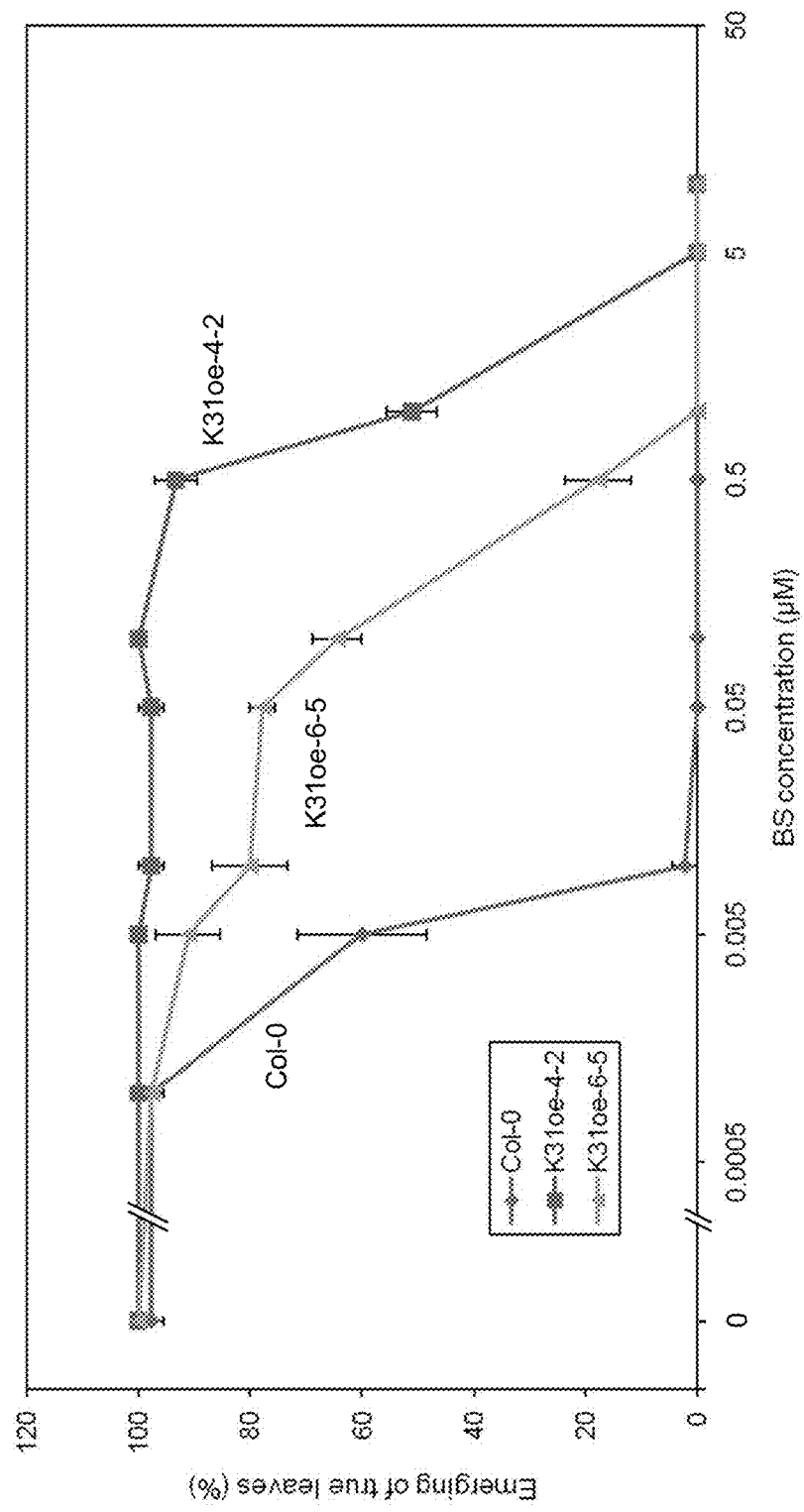
FIG. 17B is a diagram showing the results of a growth test (proportions of plant bodies with an emerging of true leaves) in a BS-containing medium on *Arabidopsis thaliana* (Col-0) transformed with a Kasalath-derived CYP72A31 gene.
Figure 17C:
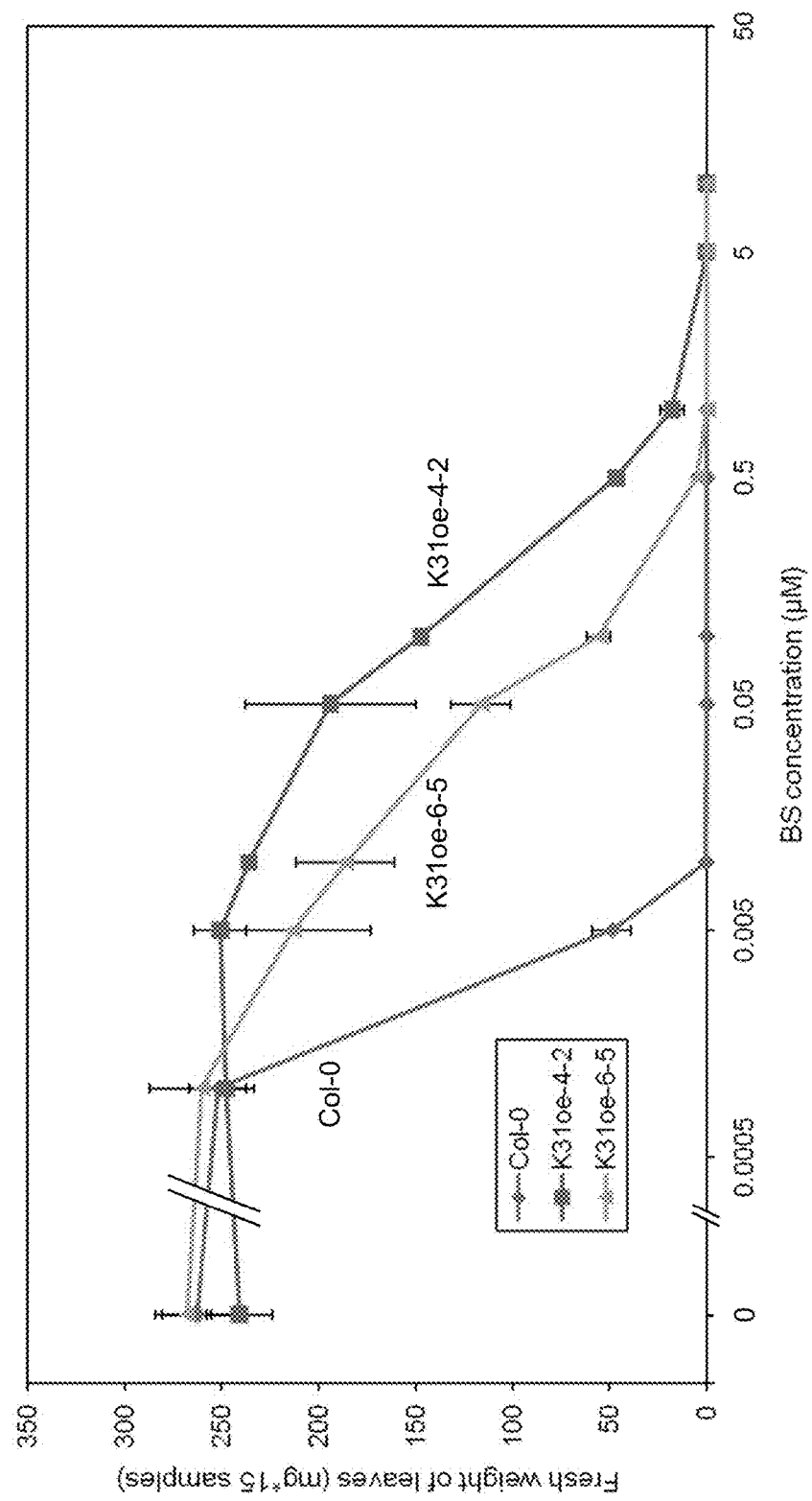
FIG. 17C is a diagram showing the results of a growth test (fresh weight of the above-ground part) in a BS-containing medium on *Arabidopsis thaliana* (Col-0) transformed with a Kasalath-derived CYP72A31 gene.

Next, 15 seeds for each of non-transformed *Arabidopsis thaliana* (NT, which is denoted by "Col-0" in FIGS. 17A-17C) and transformed plant bodies (K31-4-2 which is denoted by "K31oe-4-2" in FIGS. 17A-17C and K31-6-5 which is denoted by "K31oe-6-5" in FIGS. 17A-17C) were cultivated on a medium containing each concentration of BS. (a) The proportion of germinated seeds (seeds found to have rooting), (b) the proportion of plant bodies with an emerging of true leaves, and (c) the fresh weight of the above-ground part (as the total sum of 15 plant bodies) were examined at day 10 from onset of cultivation. FIGS. 17A to 17C illustrate the results of these (a) to (c) measurements, respectively. Note that the graphs shown in FIGS. 17A to 17C show mean±SE (n=3) of three iterations. FIGS. 17A to 17C demonstrated that K31-4-2 and K31-6-5 had significantly lower BS sensitivity compared to NT in terms of all of the indicators (a) to (c).

Figure 18A:
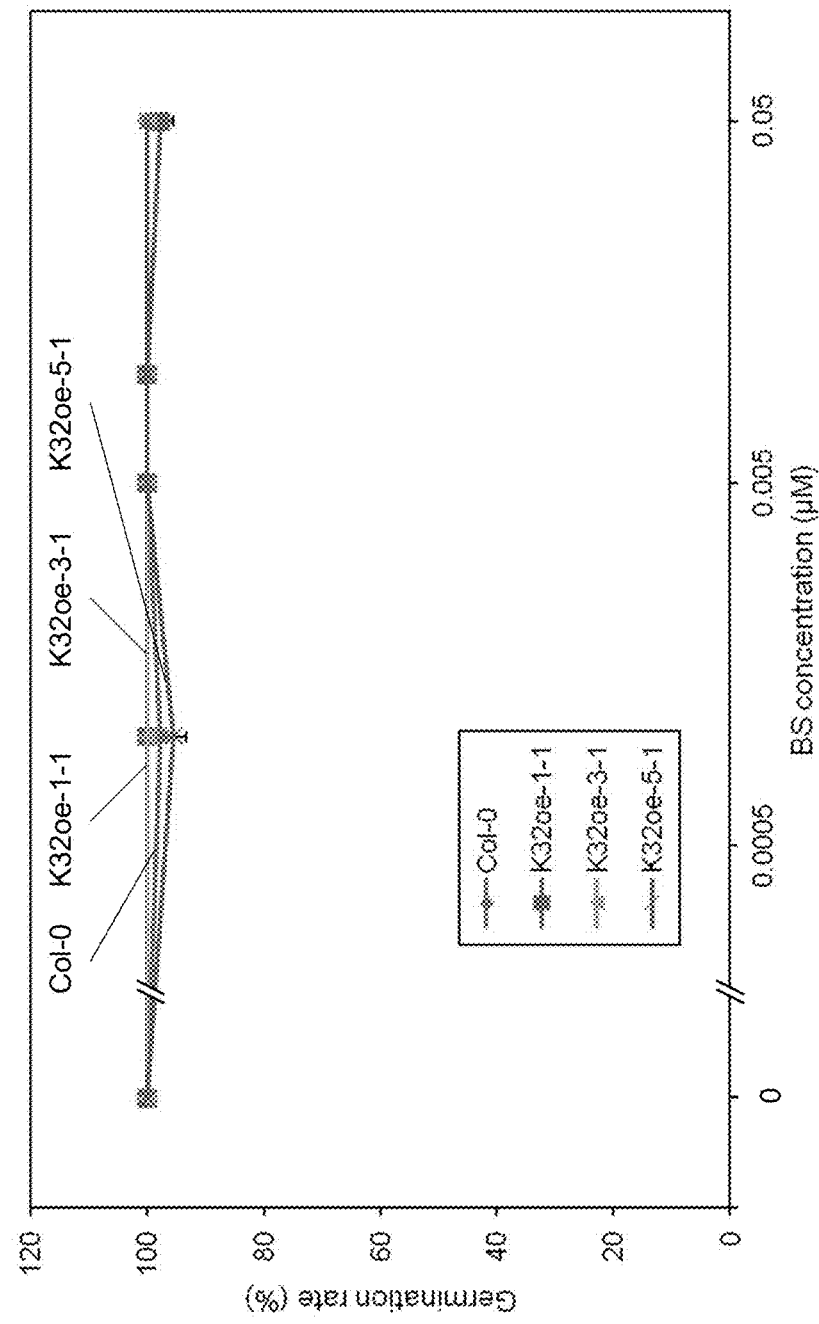
FIG. 18A is a diagram showing the results of a growth test (proportions of germinated seeds) in a BS-containing medium on *Arabidopsis thaliana* (Col-0) transformed with a Kasalath-derived CYP72A32 gene.
Figure 18B:
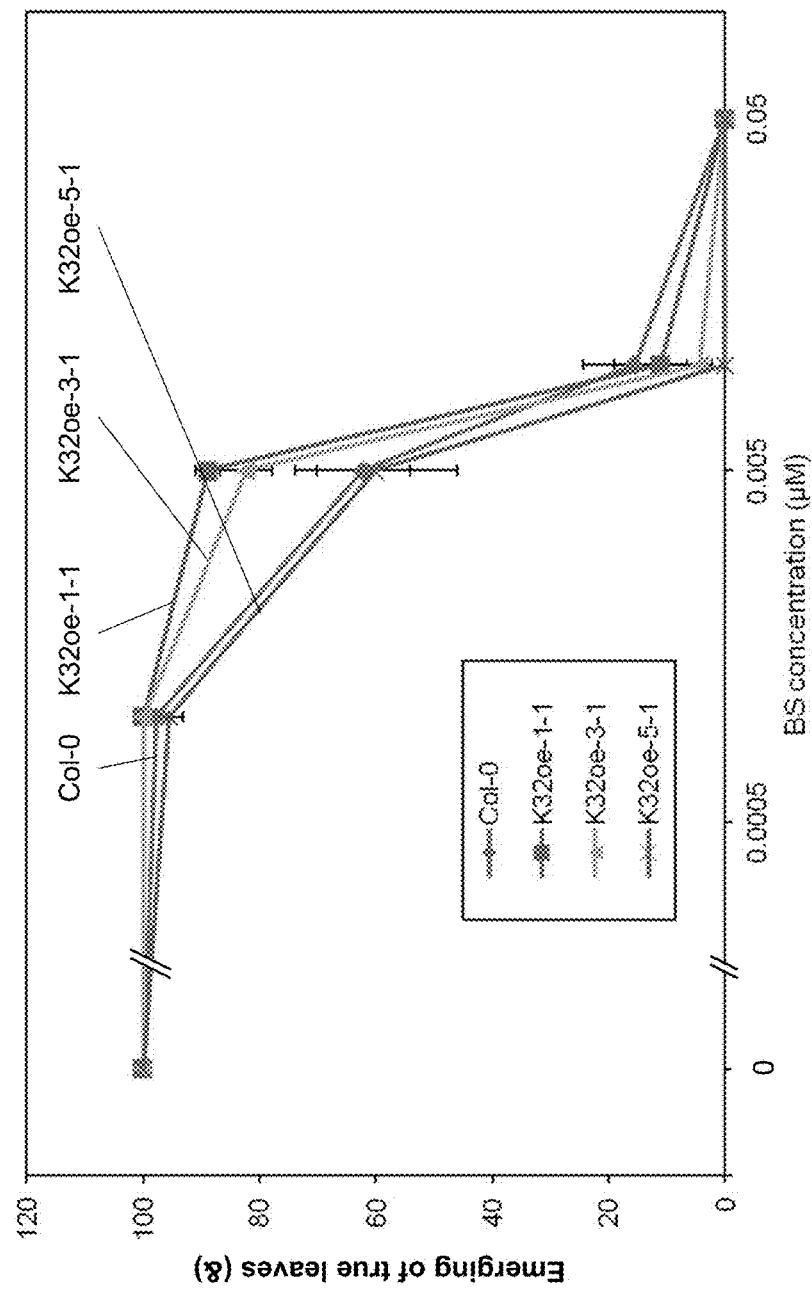
FIG. 18B is a diagram showing the results of a growth test (proportions of plant bodies with an emerging of true leaves) in a BS-containing medium on *Arabidopsis thaliana* (Col-0) transformed with a Kasalath-derived CYP72A32 gene.
Figure 18C:
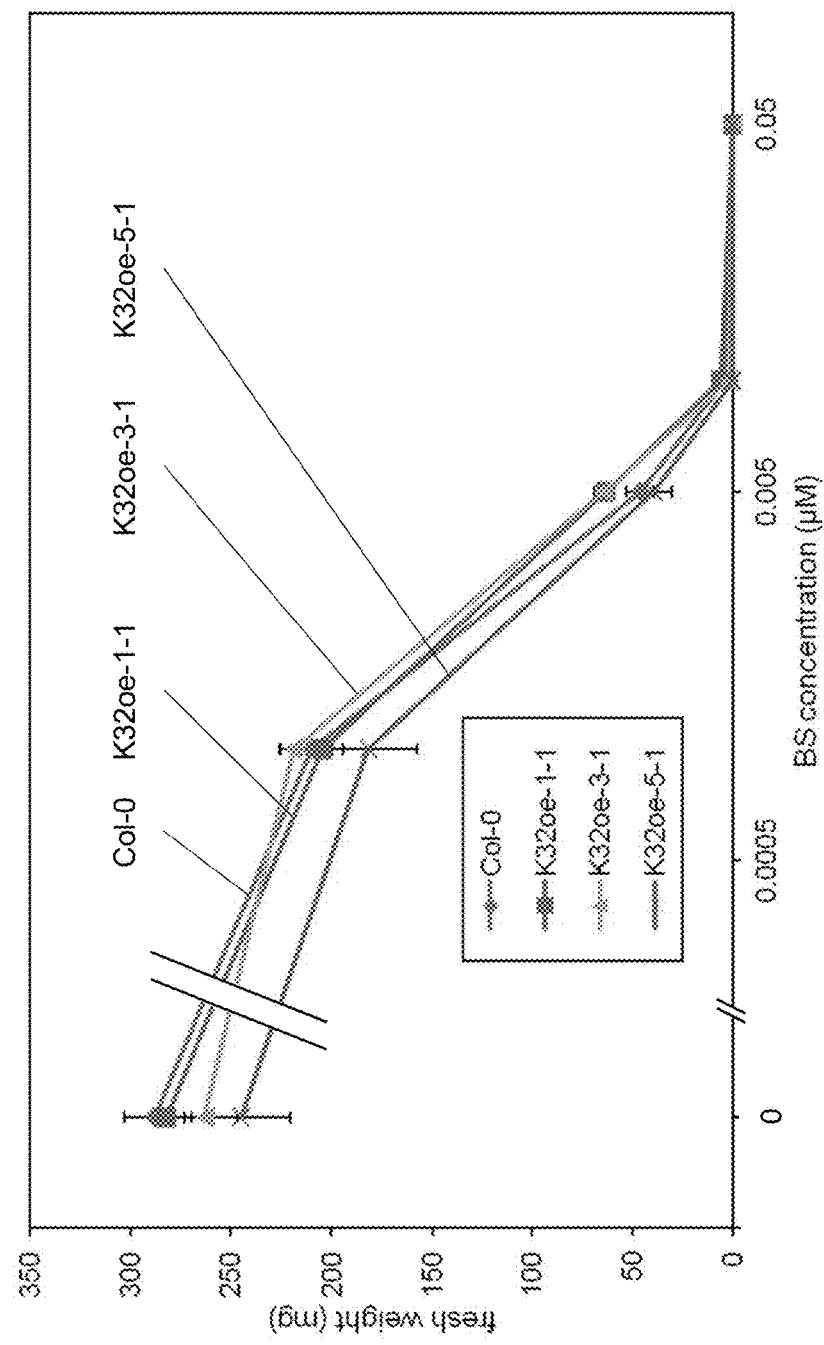
FIG. 18C is a diagram showing the results of a growth test (fresh weight of the above-ground part) in a BS-containing medium on *Arabidopsis thaliana* (Col-0) transformed with a Kasalath-derived CYP72A32 gene.

Next, 15 seeds for each of non-transformed *Arabidopsis thaliana* (NT which is denoted by "Col-0" in FIGS. 18A-18C) and transformed plant bodies (K32-1-1 which is denoted by "K32oe-1-1" in FIGS. 18A-18C, K32-3-1 which is denoted by "K32oe-3-1" in FIGS. 18A-18C, and K32-5-1 which is denoted by "K32oe-5-" in FIGS. 18A-18C) were cultivated on a medium containing each concentration of BS. (a) The proportion of germinated seeds (seeds found to have rooting), (b) the proportion of plant bodies with a developed true leaves, and (c) the fresh weight of the above-ground part (as the total sum of 15 plant bodies) were examined at day 10 from onset of cultivation. FIGS. 18A to 18C illustrate the results of these (a) to (c) measurements, respectively. Note that the graphs shown in FIGS. 18A to 18C show mean±SE (n=3) of three iterations. FIGS. 18A to 18C demonstrated that K32-1-1, K32-3-1, and K32-5-1 exhibited BS sensitivity equivalent to NT in terms of all of the indicators.

Figure 19A:
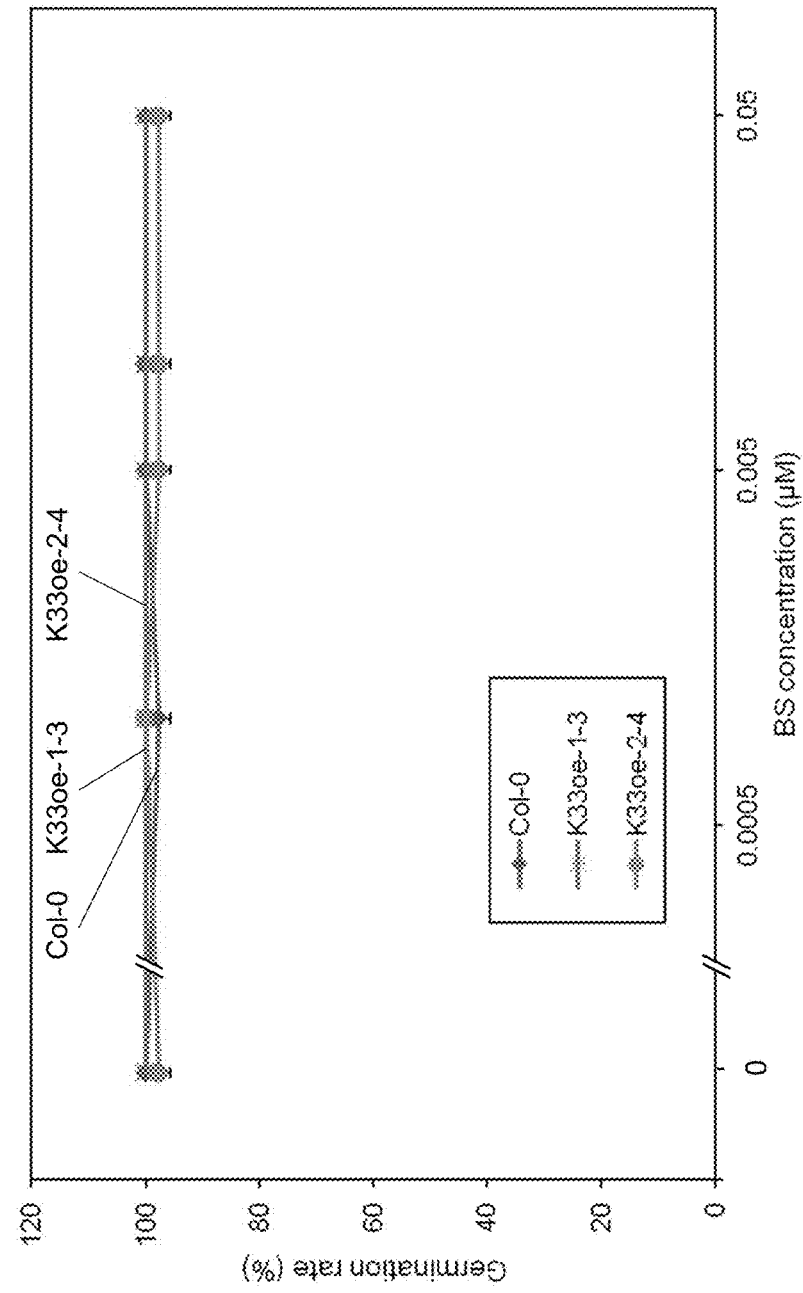
FIG. 19A is a diagram showing the results of a growth test (proportions of germinated seeds) in a BS-containing medium on *Arabidopsis thaliana* (Col-0) transformed with a Kasalath-derived CYP72A33 gene.
Figure 19B:
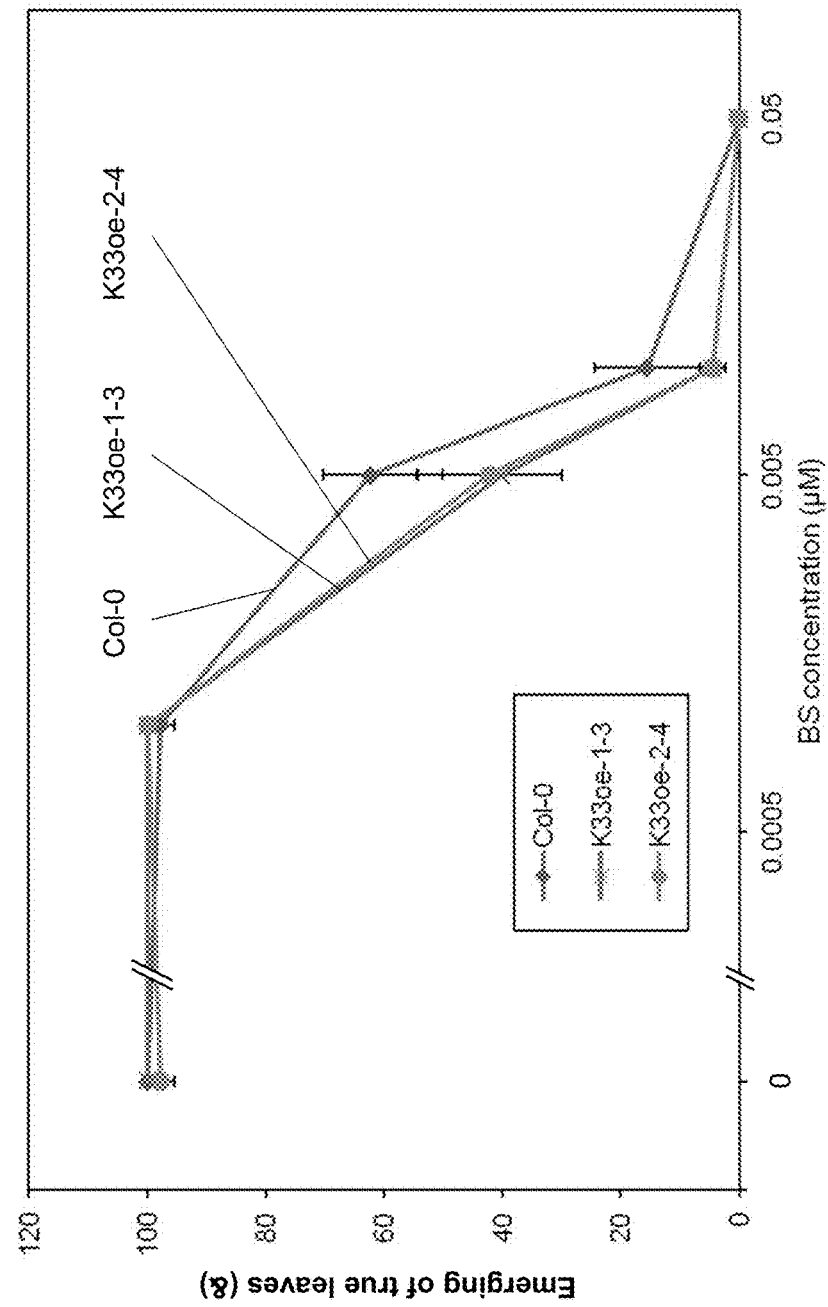
FIG. 19B is a diagram showing the results of a growth test (proportions of plant bodies with an emerging of true leaves) in a BS-containing medium on *Arabidopsis thaliana* (Col-0) transformed with a Kasalath-derived CYP72A33 gene.
Figure 19C:
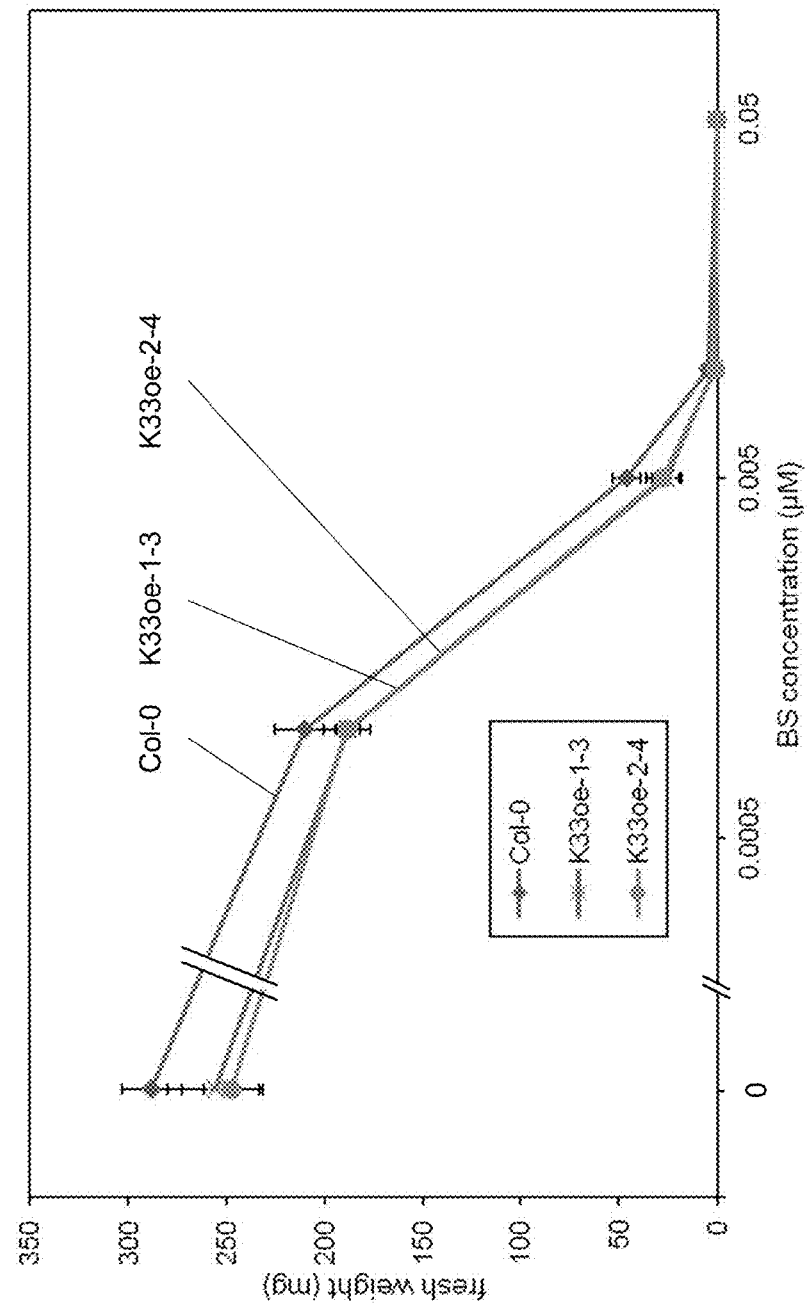
FIG. 19C is a diagram showing the results of a growth test (fresh weight of the above-ground part) in a BS-containing medium on *Arabidopsis thaliana* (Col-0) transformed with a Kasalath-derived CYP72A33 gene.

Next, 15 seeds for each of non-transformed *Arabidopsis thaliana* (NT which is denoted by "Col-0" in FIGS. 19A-19C) and transformed plant bodies (K33-1-3 which is denoted by "K33oe-1-3" in FIGS. 19A-19C and K33-2-4 which is denoted by "K33oe-2-4" in FIGS. 19A-19C) were cultivated on a medium containing each concentration of BS. (a) The proportion of germinated seeds (seeds found to have rooting), (b) the proportion of plant bodies with a developed true leaves, and (c) the fresh weight of the above-ground part (as the total sum of 15 plant bodies) were examined at day 10 from onset of cultivation. FIGS. 19A to 19C illustrate the results of these (a) to (c) measurements, respectively. Note that the graphs shown in FIGS. 19A to 19C show mean±SE (n=3) of three iterations. FIGS. 19A to 19C demonstrated that K33-1-3 and K33-2-4 exhibited BS sensitivity equivalent to NT in terms of all of the indicators.

Example 11

Drug Sensitivity Test Using *Arabidopsis thaliana* or Rice with Introduced Kasalath-Derived CYP72A31 Gene Overexpression Construct In order to examine whether a Kasalath-derived CYP72A31 gene also exhibited resistance to a drug other than BS, the homozygous variety (K31-4-2) of *Arabidopsis thaliana* transformed with HptII::35Spro::Kasalath CYP72A31::Tnos vector plasmid (pCAMBIA1390-KasCYP72A31) as prepared according to Example 10 or the homozygous progeny variety (T3) (K31-4-6-2) of rice as prepared in Example 5 was used to test drug sensitivity.

<Drug Sensitivity Test Using Transformed *Arabidopsis thaliana*>

A bag of mixed salts for Murashige-Skoog (MS) medium (manufactured by Wako Pure Chemical Industries, Ltd.) 20 g of sucrose, 3 mg of thiamin hydrochloride, 5 mg of nicotinic acid, and 0.5 mg of pyridoxine hydrochloride were dissolved in distilled water, and filled up to 1 L with distilled water. After pH adjustment to 5.8 to 6.3 with 1 M KOH, 3 g of Gelrite was added to the solution, and dissolved using a microwave. After that, the mixture was autoclaved to prepare a sterile MS medium. A test drug was added to this sterile MS medium so as to make a final concentration of 1.3, 4.1, 12, 37, 110, or 330 nM. *Arabidopsis thaliana* from a sterilized seed was seeded in the drug-containing MS medium, and cultivated at 22° C. for 12 to 14 days in a continuous light period.

Note that the drugs used in this Example were bispyribac-sodium, pyrithiobac-sodium, pyriminobac, bensulfuron-methyl, penoxsulam, pyrazosulfuron-ethyl, amidosulfuron, imazosulfuron, nicosulfuron, and propyrisulfuron.

Figure 20:
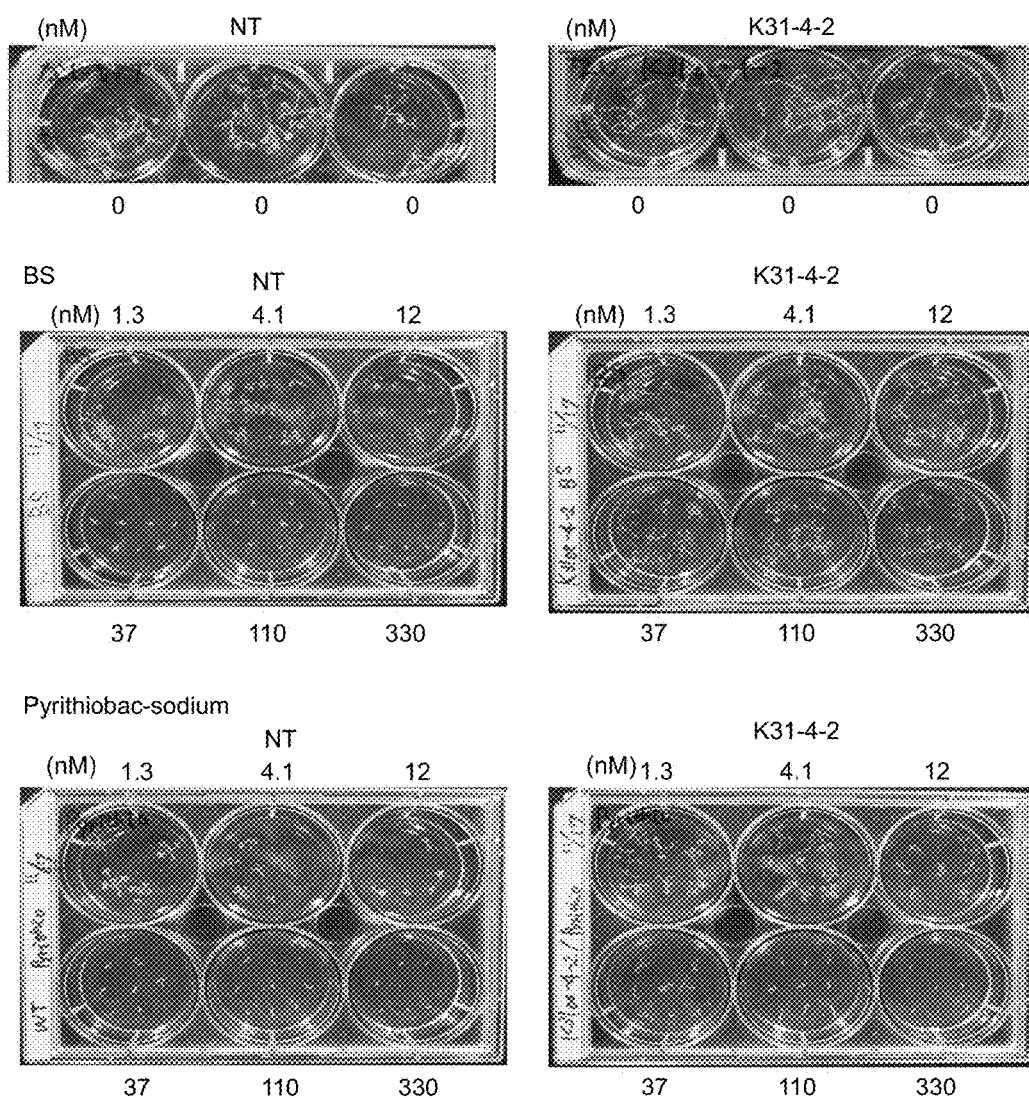
FIG. 20 is a photograph showing the results of a growth test using a drug-free medium, a BS-containing medium, or a pyrithiobac-sodium-containing medium on *Arabidopsis thaliana* (K31-4-2) transformed with a Kasalath-derived CYP72A31 gene and non-transformed *Arabidopsis thaliana* (NT).
Figure 21:
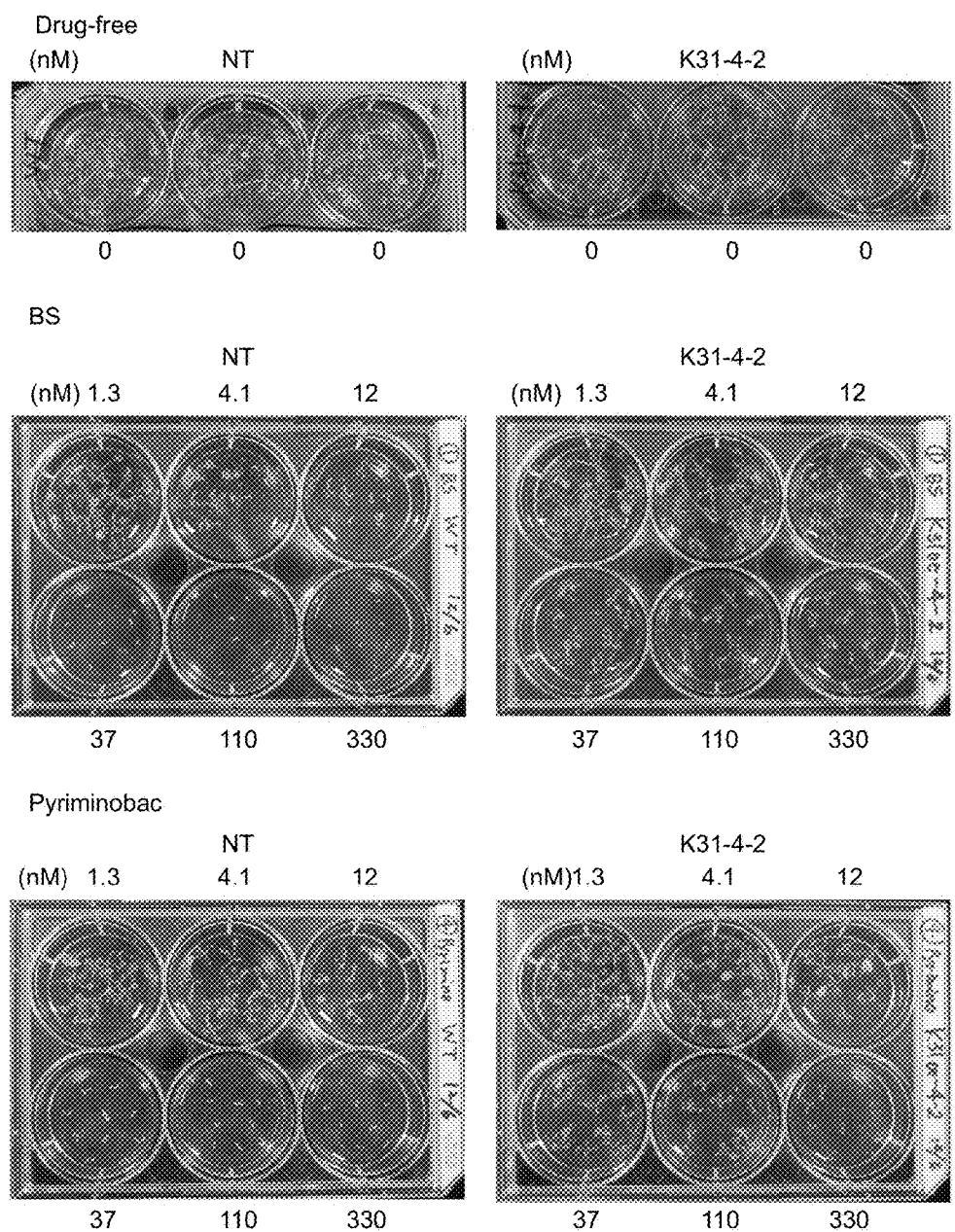
FIG. 21 is a photograph showing the results of a growth test using a drug-free medium, a BS-containing medium, or a pyriminobac-containing medium on *Arabidopsis thaliana* (K31-4-2) transformed with a Kasalath-derived CYP72A31 gene and non-transformed *Arabidopsis thaliana* (NT).
Figure 22:
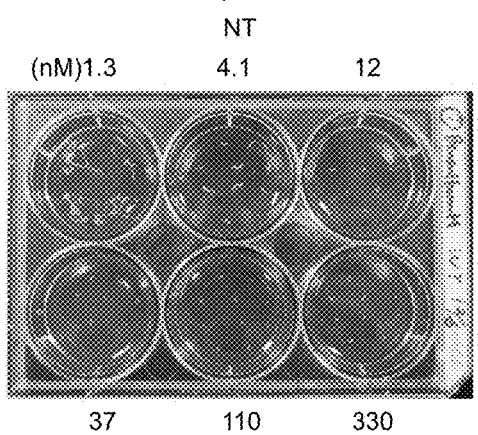
FIG. 22 is a photograph showing the results of a growth test using a bensulfuron-methyl-containing medium or a penoxsulam-containing medium on *Arabidopsis thaliana*
Figure 22:
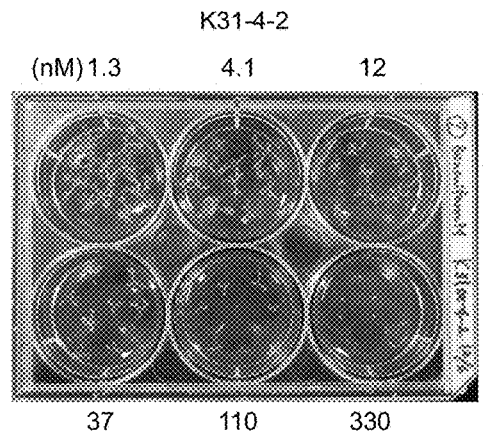
Figure 22:
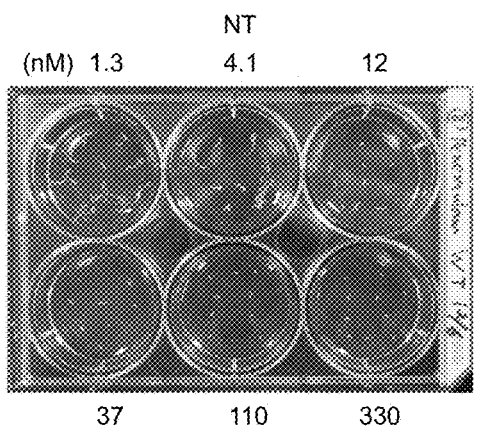
Figure 22:
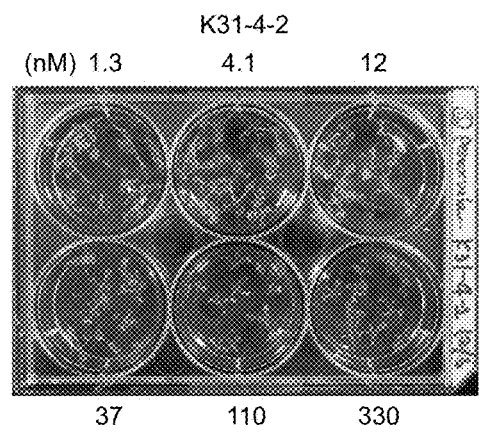

Table 2 and FIG. 20 show the results of cultivation for 12 days with bispyribac-sodium or pyrithiobac-sodium as a drug.

TABLE 2

| Drug | Drug concentration (nM) | Rate of emerging of true leaf (%) NT | Rate of emerging of true leaf (%) K31-4-2 | Ratio of sensitivity |
|---|---|---|---|---|
| BS | 0 | 80 | 97 | |
| | 1.3 | 44 | 89 | >28 |
| | 4.1 | 67 | 100 | |
| | 12 | 56 | 89 | |
| | 37 | 0 | 100 | |
| | 110 | 0 | 100 | |
| | 330 | 0 | 78 | |
| Pyrithiobac-sodium | 1.3 | 44 | 78 | 3 |
| | 4.1 | 44 | 100 | |
| | 12 | 0 | 78 | |
| | 37 | 0 | 22 | |
| | 110 | 0 | 0 | |
| | 330 | 0 | 0 | |

Day 12 after seeding

The item "Ratio of sensitivity" represents a value calculated by means of [Maximum drag concentration for ratio of emerging of true leaves of 40% or more in K31-4-2]/ [Maximum drag concentration for ratio of emerging of true leaves of 40% or more in NT].

Also, Table 3 and FIGS. 21 to 24 show the results of cultivation for 14 days with bispyribac-sodium, pyriminobac, bensulfuron-methyl, penoxsulam, pyrazosulfuron-ethyl, amidosulfuron, imazosulfuron, nicosulfuron, or propyrisulfuron as a drug.

TABLE 3

| Drug | Drug concentration (nM) | Rate of emerging of true leaf (%) NT | Rate of emerging of true leaf (%) K31-4-2 | Ratio of sensitivity |
|---|---|---|---|---|
| BS | 0 | 100 | 100 | |
| | 1.3 | 100 | 100 | >80 |
| | 4.1 | 100 | 100 | |
| | 12 | 50 | 100 | |
| | 37 | 0 | 100 | |
| | 110 | 0 | 100 | |
| | 330 | 0 | 80 | |
| Pyriminobac | 1.3 | 100 | 100 | 27 |
| | 4.1 | 90 | 100 | |
| | 12 | 10 | 100 | |
| | 37 | 0 | 100 | |
| | 110 | 0 | 100 | |
| | 330 | 0 | 50 | |
| Bensulfuron-methyl | 1.3 | 30 | 100 | >28 |
| | 4.1 | 0 | 100 | |
| | 12 | 0 | 100 | |
| | 37 | 0 | 90 | |
| | 110 | 0 | 10 | |
| | 330 | 0 | 0 | |
| Penoxsulam | 1.3 | 50 | 100 | >254 |
| | 4.1 | 10 | 100 | |
| | 12 | 0 | 100 | |
| | 37 | 0 | 100 | |
| | 110 | 0 | 100 | |
| | 330 | 0 | 100 | |
| Pyrazosulfuron-ethyl | 1.3 | 0 | 100 | >9 |
| | 4.1 | 0 | 100 | |
| | 12 | 0 | 90 | |
| | 37 | 0 | 0 | |
| | 110 | 0 | 0 | |
| | 330 | 0 | 0 | |
| Amidosulfuron | 1.3 | 100 | 100 | 3 |
| | 4.1 | 100 | 100 | |
| | 12 | 0 | 100 | |
| | 37 | 0 | 0 | |
| | 110 | 0 | 0 | |
| | 330 | 0 | 0 | |
| Imazosulfuron | 1.3 | 40 | 100 | >85 |
| | 4.1 | 10 | 100 | |
| | 12 | 0 | 100 | |
| | 37 | 0 | 100 | |
| | 110 | 0 | 90 | |
| | 330 | 0 | 0 | |
| Nicosulfuron | 1.3 | 100 | 100 | 27 |
| | 4.1 | 100 | 100 | |
| | 12 | 0 | 100 | |
| | 37 | 0 | 100 | |
| | 110 | 0 | 100 | |
| | 330 | 0 | 10 | |
| Propyrisulfuron | 1.3 | 10 | 100 | >9 |
| | 4.1 | 0 | 100 | |
| | 12 | 0 | 100 | |
| | 37 | 0 | 70 | |
| | 110 | 0 | 0 | |
| | 330 | 0 | 0 | |

Day 14 after seeding

The item "Ratio of sensitivity" represents a value calculated by means of [Maximum drag concentration for ratio of emerging of true leaves of 80% or more in K31-4-2]/ [Maximum drag concentration for ratio of emerging of true leaves of 80% or more in NT].

Tables 2 and 3 and FIGS. 20 to 24 demonstrated that the homozygous variety (K31-4-2) of *Arabidopsis thaliana* having a Kasalath-derived CYP72A31 gene introduced so as to be overexpressed exhibited resistance to bispyribac-sodium, pyrithiobac-sodium, pyriminobac, bensulfuron-methyl, penoxsulam, pyrazosulfuron-ethyl, amidosulfuron, imazosulfuron, nicosulfuron, and propyrisulfuron.

<Drug Sensitivity Test Using Transformed Rice>

According to the method of Example 1, a gellan gum medium containing a test drug at a concentration of 0.01, 0.1, 1, or 10 µM was prepared. Rice seeds were sterilized, germinated, seeded in the medium, and cultivated. Table 4 and FIG. 25 show the results.

TABLE 4

| Drug | Drug concentration (µM) | CK ratio (%)* Wild-type rice (Nipponbare) | CK ratio (%)* CYP72A31-overexpressing rice (K31-4-6-2) | Ratio of sensitivity |
|---|---|---|---|---|
| BS | 0.01 | 82 | 106 | >100 |
| | 0.1 | 64 | 97 | |
| | 1 | 22 | 103 | |
| | 10 | 3 | 74 | |
| Pinoxaden | 0.01 | 59 | 95 | 10 |
| | 0.1 | 3 | 48 | |
| | 1 | 3 | 9 | |
| | 10 | 3 | 3 | |

*CK ratio: Compared with plant height in drug-free medium

The item "Ratio of sensitivity" represents a value calculated by means of [Maximum drag concentration for CK ratio of 40% or more in K31-4-6-2]/[Maximum drag concentration for CK ratio of 40% or more in Wild-type rice].

Table 4 and FIG. 25 demonstrated that the transformed rice overexpressing a Kasalath-derived CYP72A31 gene exhibited resistance to bispyribac-sodium and pinoxaden.

From the above results, the CYP72A31 gene was found to exhibit resistance even to a growth inhibitor other than BS.

Example 12

Selection of Rice Callus Transformant with Introduced pCAMBIA1390-KasCYP72A31 by Using BS Rice transformed with pCAMBIA1390-KasCYP72A31 was used to examine whether a Kasalath-derived CYP72A31 gene was able to be used as a selection marker for transformation with BS as a selection reagent. According to Example 5, rice (Nipponbare) was transformed with pCAMBIA1390-KasCYP72A31 or pSTARA-sGFP by using an *Agrobacterium* method.
<Selection of Drug-Resistant Callus in N6D Medium>

Rice (Nipponbare) calluses transformed with pCAMBIA1390-KasCYP72A31 were cultured for 4 weeks in an N6D medium containing 0.1 or 0.25 µM BS or an N6D medium containing 50 ppm hygromycin to select drug-resistant calluses. Also, rice calluses transformed with pSTARA-sGFP were selected in a similar manner in an N6D medium containing 0.25 µM BS.

FIG. 26 illustrates the results. These results demonstrated that when rice calluses transformed with pCAMBIA1390-KasCYP72A31 were cultured in an N6D medium containing 0.1 or 0.25 µM BS, selection efficiency (ratio of the resulting transformed calluses/all calluses) was 71% and 61%, respectively. When the same transformed calluses were cultured in an N6D) medium containing 50 ppm hygromycin, selection efficiency was 79%, which was substantially equivalent to the selection efficiency obtained with BS as a selection reagent. Note that the selection efficiency was 82% in the BS selection of rice calluses transformed with pSTARA-sGFP.
<Redifferentiation of Transformant>

Next, the calluses transformed with pCAMBIA1390-KasCYP72A31 and selected in an N6D medium containing 0.1 µM BS were cultured for 13 days in a rice redifferentiation medium RE-III containing 0.25 µM BS. After that, the calluses were cultured for 14 days in a drug-free redifferentiation medium RE-III.

As a result, redifferentiated plant bodies were obtained as shown in FIG. 27.

From the above results, the CYP72A31 gene was found to be able to be used as a marker for transformation with BS as a selection reagent.

All publications, patents, and patent applications cited herein are incorporated herein by reference in their entirety.

The invention claimed is:

1. An expression vector comprising a polynucleotide and a heterologous promoter operationally linked to the polynucleotide, wherein the polynucleotide is any of the following (a) to (c):

(a) a polynucleotide encoding a polypeptide comprising the amino acid sequence of SEQ ID NO: 2;

(b) a polynucleotide encoding a polypeptide having 95% or higher sequence identity with SEQ ID NO: 2, wherein the polypeptide imparts resistance to an acetolactate synthase inhibitor or pinoxaden; and (c) a polynucleotide strand complementary to the full length nucleotide sequence of SEQ ID NO: 1.

2. The expression vector of claim 1, further comprising a second polynucleotide.

3. A transformant comprising the expression vector of claim 1 or 2.

4. A transgenic plant comprising a polynucleotide and a heterologous promoter operationally linked to the polynucleotide, wherein the polynucleotide is any of the following (a) to (c):
(a) a polynucleotide encoding a polypeptide comprising the amino acid sequence of SEQ ID NO: 2;
(b) a polynucleotide encoding a polypeptide having 95% or higher sequence identity with SEQ ID NO: 2, wherein the polypeptide imparts resistance to an acetolactate synthase inhibitor or pinoxaden; and
(c) a polynucleotide strand complementary to the full length nucleotide sequence of SEQ ID NO: 1.

5. A plant body, a plant organ, a plant tissue, or a cultured plant cell of the transgenic plant of claim 4.

6. A method for producing a plant having resistance to an acetolactate synthase inhibitor or pinoxaden, comprising a step of: introducing a polynucleotide encoding a cytochrome P450 wherein the polynucleotide is operably linked to a heterologous promoter and is any of the following (a) to (b) into a plant:
(a) a polynucleotide encoding a polypeptide comprising the amino acid sequence of SEQ ID NO: 2; and
(b) a polynucleotide encoding a polypeptide having 95% or higher sequence identity with SEQ ID NO: 2, wherein the polypeptide imparts resistance to an acetolactate synthase inhibitor or pinoxaden.

7. A method for controlling weeds harmful to the transgenic plant of claim 4, comprising: cultivating the transgenic plant of claim 5 in a field; and performing an acetolactate synthase inhibitor or pinoxaden treatment in the field where the transgenic plant is cultivated.

8. A method for transformation, comprising the steps of: introducing the expression vector of claim 2 into a host sensitive to an acetolactate synthase inhibitor or pinoxaden; and screening for a cell growing under the presence of the acetolactate synthase inhibitor or pinoxaden as a transformant.

9. The expression vector of claim 1, wherein the heterologous promoter is at least one selected from the group consisting of *Agrobacterium tumefaciens*-derived Nos promoter, a cauliflower mosaic virus 35S promoter (CaMV35S), actin gene promoters, ubiquitin gene promoters, a nopaline synthase gene promoter, a tobacco PR1a gene promoter, a tomato ribulose-1,5-diphosphate carboxylase-oxidase small subunit gene promoter, a napin gene promoter, and an oleosin gene promoter.

10. A plant having resistance to an acetolactate synthase inhibitor or pinoxaden, which is produced by the method of claim 6.

11. A method for controlling weeds harmful to the plant of claim 10, comprising: cultivating the plant of claim 10 in a field; and performing an acetolactate synthase inhibitor or pinoxaden treatment in the field where the plant is cultivated.

* * * * *

SEQUENCE LISTING

```
<160> NUMBER OF SEQ ID NOS: 10

<210> SEQ ID NO 1
<211> LENGTH: 1599
<212> TYPE: DNA
<213> ORGANISM: Oryza sativa
<220> FEATURE:
<221> NAME/KEY: CDS
<222> LOCATION: (1)..(1599)

<400> SEQUENCE: 1 atg gtt ttc aga ggg tgg ttg atg tgg gct ccg gcc tca gcg cca gtc       48
Met Val Phe Arg Gly Trp Leu Met Trp Ala Pro Ala Ser Ala Pro Val
1               5                   10                  15 ctc gtg gtg ttc ggt ctc ctc ttc ggc ctc gcc ctc gtg tgg cag gcc       96
Leu Val Val Phe Gly Leu Leu Phe Gly Leu Ala Leu Val Trp Gln Ala
                20                  25                  30 ggc cgc ctg ctt cac cgg ctg tgg tgg cgg ccg cgg cgg ctg gag aag      144
Gly Arg Leu Leu His Arg Leu Trp Trp Arg Pro Arg Arg Leu Glu Lys
            35                  40                  45 gcg ctg cgc gcg cgg ggc ctc cgc ggc tcg tcc tac cgc ttc ctc acc      192
Ala Leu Arg Ala Arg Gly Leu Arg Gly Ser Ser Tyr Arg Phe Leu Thr
        50                  55                  60 ggc gac ctc gcg gag gag agc cgg cgg agg aag gag gcc tgg gcg agg      240
Gly Asp Leu Ala Glu Glu Ser Arg Arg Arg Lys Glu Ala Trp Ala Arg
65                  70                  75                  80 ccg ctg ccg ctg cgg tgc cac gac atc gcg ccg cgc atc aag ccg ttc      288
Pro Leu Pro Leu Arg Cys His Asp Ile Ala Pro Arg Ile Lys Pro Phe
                85                  90                  95 ctc cac gac acc ctc ggg gag cac ggc aag cag cgg cag ccg tgc atc      336
Leu His Asp Thr Leu Gly Glu His Gly Lys Gln Arg Gln Pro Cys Ile
                100                 105                 110 acc tgg ttc ggc ccg acg ccg gag gtg aac atc acc gat ccc gag ctg      384
Thr Trp Phe Gly Pro Thr Pro Glu Val Asn Ile Thr Asp Pro Glu Leu
            115                 120                 125 gcc aag gtc gtc ctg tcc aac aag ttc ggc cac ttg gag agg gtc agg      432
Ala Lys Val Val Leu Ser Asn Lys Phe Gly His Leu Glu Arg Val Arg
```

-continued

| | | |
|---|---|---|
| 130 | 135 | 140 |

```
ttc aag gag gtg tcg aag ctg cta tcc caa ggc ctc acc tac cac gag    480
Phe Lys Glu Val Ser Lys Leu Leu Ser Gln Gly Leu Thr Tyr His Glu
145                 150                 155                 160 ggc gag aag tgg gtc aag cac agg agg atc atc aac ccg gct ttc cag    528
Gly Glu Lys Trp Val Lys His Arg Arg Ile Ile Asn Pro Ala Phe Gln
                165                 170                 175 ctc gag aag ctc aag ctc atg ctg cca gcg ttt tct gca tgc tgc gag    576
Leu Glu Lys Leu Lys Leu Met Leu Pro Ala Phe Ser Ala Cys Cys Glu
            180                 185                 190 gaa ctg ata agc agg tgg ata ggg tcc att ggc tgt gat ggc tcg tac    624
Glu Leu Ile Ser Arg Trp Ile Gly Ser Ile Gly Cys Asp Gly Ser Tyr
        195                 200                 205 gag gtg gat tgc tgg ccg gag ctc aag agc ctc acc gga gat gtc atc    672
Glu Val Asp Cys Trp Pro Glu Leu Lys Ser Leu Thr Gly Asp Val Ile
    210                 215                 220 tcg cgc acc gcg ttc gga agc agc tat ctt gaa gga aga agg gtc ttc    720
Ser Arg Thr Ala Phe Gly Ser Ser Tyr Leu Glu Gly Arg Arg Val Phe
225                 230                 235                 240 gag ctg cag gcc gag caa ttt gag cgc gca atg aaa tgc atg cag aag    768
Glu Leu Gln Ala Glu Gln Phe Glu Arg Ala Met Lys Cys Met Gln Lys
                245                 250                 255 att tcc atc ccg ggt tac atg tct ttg cct att gag aac aac cgg aag    816
Ile Ser Ile Pro Gly Tyr Met Ser Leu Pro Ile Glu Asn Asn Arg Lys
            260                 265                 270 atg cat caa ata aat aaa gag atc gaa tcg att cta aga ggt ata att    864
Met His Gln Ile Asn Lys Glu Ile Glu Ser Ile Leu Arg Gly Ile Ile
        275                 280                 285 ggg aaa aaa atg caa gct atg aaa gaa ggt gaa agc aca aaa gat gat    912
Gly Lys Lys Met Gln Ala Met Lys Glu Gly Glu Ser Thr Lys Asp Asp
    290                 295                 300 tta ctt ggc ata ttg ctt gag tca aac aca aag cac atg gaa gag aat    960
Leu Leu Gly Ile Leu Leu Glu Ser Asn Thr Lys His Met Glu Glu Asn
305                 310                 315                 320 ggt caa tca agc cag ggg ttg aca atg aag gat atc gtg gag gag tgc    1008
Gly Gln Ser Ser Gln Gly Leu Thr Met Lys Asp Ile Val Glu Glu Cys
                325                 330                 335 aag ctg ttc tac ttt gca gga gcg gag aca aca tca gtg ctt ctc aca    1056
Lys Leu Phe Tyr Phe Ala Gly Ala Glu Thr Thr Ser Val Leu Leu Thr
            340                 345                 350 tgg gcc atg ctg cta tta agc atg cac ccg gag tgg cag gac cgt gca    1104
Trp Ala Met Leu Leu Leu Ser Met His Pro Glu Trp Gln Asp Arg Ala
        355                 360                 365 agg gaa gag atc ctg gga tta ttt agg aag aac aaa cct gac tac gaa    1152
Arg Glu Glu Ile Leu Gly Leu Phe Arg Lys Asn Lys Pro Asp Tyr Glu
    370                 375                 380 ggc ttg agc cgc ctc aaa att gtg acg atg atc ctc tac gag gtt ctt    1200
Gly Leu Ser Arg Leu Lys Ile Val Thr Met Ile Leu Tyr Glu Val Leu
385                 390                 395                 400 cgg ttg tac cca ccg ttc atc gag att ggt cgg aaa aca tac aaa gag    1248
Arg Leu Tyr Pro Pro Phe Ile Glu Ile Gly Arg Lys Thr Tyr Lys Glu
                405                 410                 415 atg gag ata gga gga gtc act tac cca gct ggt gtc agc att aaa atc    1296
Met Glu Ile Gly Gly Val Thr Tyr Pro Ala Gly Val Ser Ile Lys Ile
            420                 425                 430 ccc gtg ttg ttc atc cac cat gat ccg gac acc tgg gga agt gat gtg    1344
Pro Val Leu Phe Ile His His Asp Pro Asp Thr Trp Gly Ser Asp Val
        435                 440                 445 cat gag ttc aaa cct gag agg ttc tct gag ggg atc tct aag gcg tct    1392
```

```
                His Glu Phe Lys Pro Glu Arg Phe Ser Glu Gly Ile Ser Lys Ala Ser
                    450                 455                 460 aag gat ccg ggt gca ttc ctc ccg ttc ggt tgg ggg cca cga atc tgc         1440
Lys Asp Pro Gly Ala Phe Leu Pro Phe Gly Trp Gly Pro Arg Ile Cys
465                 470                 475                 480 atc ggc caa aac ttc gcg ctg ctt gag gcc aag atg gca ttg tgc ctg         1488
Ile Gly Gln Asn Phe Ala Leu Leu Glu Ala Lys Met Ala Leu Cys Leu
                485                 490                 495 att ctt caa cgc ttg gag ttt gag ctt gcg cca tcg tat act cat gcg         1536
Ile Leu Gln Arg Leu Glu Phe Glu Leu Ala Pro Ser Tyr Thr His Ala
                500                 505                 510 ccg cat act atg gta act ctg cat cca atg cac ggt gca cag att aaa         1584
Pro His Thr Met Val Thr Leu His Pro Met His Gly Ala Gln Ile Lys
            515                 520                 525 gtt aga gct ata tga                                                     1599
Val Arg Ala Ile
    530

<210> SEQ ID NO 2
<211> LENGTH: 532
<212> TYPE: PRT
<213> ORGANISM: Oryza sativa

<400> SEQUENCE: 2

Met Val Phe Arg Gly Trp Leu Met Trp Ala Pro Ala Ser Ala Pro Val
1               5                   10                  15

Leu Val Val Phe Gly Leu Leu Phe Gly Leu Ala Leu Val Trp Gln Ala
            20                  25                  30

Gly Arg Leu Leu His Arg Leu Trp Trp Arg Pro Arg Leu Glu Lys
        35                  40                  45

Ala Leu Arg Ala Arg Gly Leu Arg Gly Ser Ser Tyr Arg Phe Leu Thr
    50                  55                  60

Gly Asp Leu Ala Glu Glu Ser Arg Arg Lys Glu Ala Trp Ala Arg
65                  70                  75                  80

Pro Leu Pro Leu Arg Cys His Asp Ile Ala Pro Arg Ile Lys Pro Phe
                85                  90                  95

Leu His Asp Thr Leu Gly Glu His Gly Lys Gln Arg Gln Pro Cys Ile
            100                 105                 110

Thr Trp Phe Gly Pro Thr Pro Glu Val Asn Ile Thr Asp Pro Glu Leu
        115                 120                 125

Ala Lys Val Val Leu Ser Asn Lys Phe Gly His Leu Glu Arg Val Arg
    130                 135                 140

Phe Lys Glu Val Ser Lys Leu Leu Ser Gln Gly Leu Thr Tyr His Glu
145                 150                 155                 160

Gly Glu Lys Trp Val Lys His Arg Arg Ile Ile Asn Pro Ala Phe Gln
                165                 170                 175

Leu Glu Lys Leu Lys Leu Met Leu Pro Ala Phe Ser Ala Cys Cys Glu
            180                 185                 190

Glu Leu Ile Ser Arg Trp Ile Gly Ser Ile Gly Cys Asp Gly Ser Tyr
        195                 200                 205

Glu Val Asp Cys Trp Pro Glu Leu Lys Ser Leu Thr Gly Asp Val Ile
    210                 215                 220

Ser Arg Thr Ala Phe Gly Ser Ser Tyr Leu Glu Gly Arg Arg Val Phe
225                 230                 235                 240

Glu Leu Gln Ala Glu Gln Phe Glu Arg Ala Met Lys Cys Met Gln Lys
                245                 250                 255
```

```
Ile Ser Ile Pro Gly Tyr Met Ser Leu Pro Ile Glu Asn Asn Arg Lys
            260                 265                 270

Met His Gln Ile Asn Lys Glu Ile Ser Ile Leu Arg Gly Ile Ile
            275                 280                 285

Gly Lys Lys Met Gln Ala Met Lys Glu Gly Glu Ser Thr Lys Asp Asp
            290                 295                 300

Leu Leu Gly Ile Leu Leu Glu Ser Asn Thr Lys His Met Glu Glu Asn
305                 310                 315                 320

Gly Gln Ser Ser Gln Gly Leu Thr Met Lys Asp Ile Val Glu Glu Cys
            325                 330                 335

Lys Leu Phe Tyr Phe Ala Gly Ala Glu Thr Thr Ser Val Leu Leu Thr
            340                 345                 350

Trp Ala Met Leu Leu Leu Ser Met His Pro Glu Trp Gln Asp Arg Ala
            355                 360                 365

Arg Glu Glu Ile Leu Gly Leu Phe Arg Lys Asn Lys Pro Asp Tyr Glu
            370                 375                 380

Gly Leu Ser Arg Leu Lys Ile Val Thr Met Ile Leu Tyr Glu Val Leu
385                 390                 395                 400

Arg Leu Tyr Pro Pro Phe Ile Glu Ile Gly Arg Lys Thr Tyr Lys Glu
            405                 410                 415

Met Glu Ile Gly Gly Val Thr Tyr Pro Ala Gly Val Ser Ile Lys Ile
            420                 425                 430

Pro Val Leu Phe Ile His His Asp Pro Asp Thr Trp Gly Ser Asp Val
            435                 440                 445

His Glu Phe Lys Pro Glu Arg Phe Ser Glu Gly Ile Ser Lys Ala Ser
            450                 455                 460

Lys Asp Pro Gly Ala Phe Leu Pro Phe Gly Trp Gly Pro Arg Ile Cys
465                 470                 475                 480

Ile Gly Gln Asn Phe Ala Leu Leu Glu Ala Lys Met Ala Leu Cys Leu
            485                 490                 495

Ile Leu Gln Arg Leu Glu Phe Glu Leu Ala Pro Ser Tyr Thr His Ala
            500                 505                 510

Pro His Thr Met Val Thr Leu His Pro Met His Gly Ala Gln Ile Lys
            515                 520                 525

Val Arg Ala Ile
        530

<210> SEQ ID NO 3
<211> LENGTH: 26
<212> TYPE: DNA
<213> ORGANISM: Artificial
<220> FEATURE:
<223> OTHER INFORMATION: Synthetic DNA

<400> SEQUENCE: 3
gaagaacaaa cctgactacg aaggct                                        26

<210> SEQ ID NO 4
<211> LENGTH: 30
<212> TYPE: DNA
<213> ORGANISM: Artificial
<220> FEATURE:
<223> OTHER INFORMATION: Synthetic DNA

<400> SEQUENCE: 4
ctccatctct ttgtatgttt tccgaccaat                                    30
```

```
<210> SEQ ID NO 5
<211> LENGTH: 28
<212> TYPE: DNA
<213> ORGANISM: Artificial
<220> FEATURE:
<223> OTHER INFORMATION: Synthetic DNA

<400> SEQUENCE: 5
aggactattt gggaagaaca aacctgag                                        28

<210> SEQ ID NO 6
<211> LENGTH: 29
<212> TYPE: DNA
<213> ORGANISM: Artificial
<220> FEATURE:
<223> OTHER INFORMATION: Synthetic DNA

<400> SEQUENCE: 6
ttcatctcct tgtatgttct ccgcttaag                                       29

<210> SEQ ID NO 7
<211> LENGTH: 27
<212> TYPE: DNA
<213> ORGANISM: Artificial
<220> FEATURE:
<223> OTHER INFORMATION: Synthetic DNA

<400> SEQUENCE: 7
ggaagaataa accagactat gatggcc                                         27

<210> SEQ ID NO 8
<211> LENGTH: 30
<212> TYPE: DNA
<213> ORGANISM: Artificial
<220> FEATURE:
<223> OTHER INFORMATION: Synthetic DNA

<400> SEQUENCE: 8
ctccatctcc ttgtatgttt ttcgagtaag                                      30

<210> SEQ ID NO 9
<211> LENGTH: 25
<212> TYPE: DNA
<213> ORGANISM: Artificial
<220> FEATURE:
<223> OTHER INFORMATION: Synthetic DNA

<400> SEQUENCE: 9
aggccaatcg tgagaagatg accca                                           25

<210> SEQ ID NO 10
<211> LENGTH: 24
<212> TYPE: DNA
<213> ORGANISM: Artificial
<220> FEATURE:
<223> OTHER INFORMATION: Synthetic DNA

<400> SEQUENCE: 10
gtgtggctga caccatcacc agag                                            24
```